United States Patent [19]

Numata et al.

[11] 4,200,575
[45] Apr. 29, 1980

[54] 7[(2-THIAZOLYL)-2-(OX-OIMINO)ACETAMIDO]CEPHALOSPORIN DERIVATIVES

[75] Inventors: Mitsuo Numata, Takatsuki; Tatsuo Nishimura, Ashiya, both of Japan

[73] Assignee: Takeda Chemical Industries, Ltd., Osaka, Japan

[21] Appl. No.: 930,041

[22] Filed: Aug. 1, 1978

[30] Foreign Application Priority Data

Aug. 6, 1977 [JP] Japan .................................. 52-94469

[51] Int. Cl.² .................. A61K 31/545; C07D 501/34; C07D 501/36; C07D 501/46
[52] U.S. Cl. ...................................... 424/246; 544/22; 544/25; 544/27; 544/28
[58] Field of Search .................. 544/22, 25, 27, 28; 424/246

[56] References Cited

U.S. PATENT DOCUMENTS

| 4,024,134 | 5/1977 | Gregson et al. ............... 544/25 |
| 4,024,137 | 5/1977 | Cook et al. ................... 424/246 |
| 4,098,888 | 7/1978 | Ochiai et al. ................. 424/246 |

*Primary Examiner*—David Wheeler

*Attorney, Agent, or Firm*—Wenderoth, Lind & Ponack

[57] ABSTRACT

Novel [2-(syn)-carbamoyloximinoacetamido]cephalosporins of the formula:

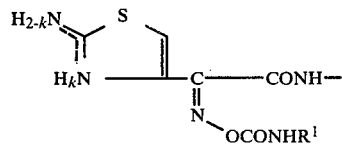

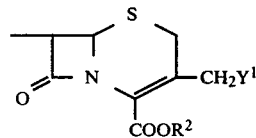

[wherein, $Y^1$ is hydrogen, hydroxyl, carbamoyloxy, acyloxy, quaternary ammonium or nitrogen-containing heterocyclic thio; $R^1$ is alkyl, aralkyl or aryl; $R^2$ is hydrogen or an ester residue; k is 0 or 1] and a salt thereof show strong antibacterial activities particularly against Gram-negative bacteria and they are useful as antibacterial agents.

25 Claims, No Drawings

7[(2-THIAZOLYL)-2-(OXOIMINO)ACETAMIDO]-CEPHALOSPORIN DERIVATIVES

DETAILED EXPLANATION OF INVENTION

This invention relates to cephalosporin derivatives. More particularly, the invention relates to [2-(syn)-carbamoyloximinoacetamido]cephalosporins of the formula:

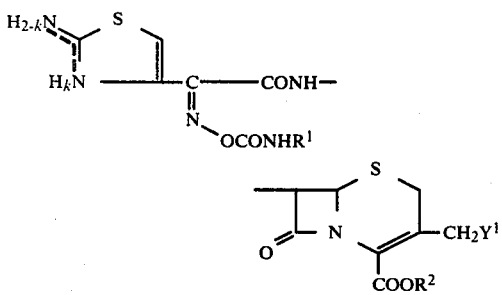

[wherein $Y^1$ is hydrogen, hydroxyl, carbamoyloxy, acyloxy, quaternary ammonium or nitrogen-containing heterocyclic thio; $R^1$ is alkyl, aralkyl or aryl; $R^2$ is hydrogen or an ester residue; k is 0 or 1] and salts thereof, processes for the production of said cephalosporins or salts, and pharmaceutical compositions containing said cephalosporins or salts.

The [2-(syn)-carbamoyloximinoacetamido]cephalosporins of formula [I] and salts thereof (hereinafter sometimes referred to generally as the cephalosporin derivatives of the invention) are novel and useful antimicrobial agents which are of value as therapeutic agents for the treatment of diseases in animals including domestic fowls and humans, particularly the infectious diseases caused by gram-positive or gram-negative bacteria.

Today several semi-synthetic cephalosporin drugs having broad antimicrobial spectra are available on the market and have accomplished excellent clinical results in the therapy of various infectious diseases. However, with the amazing development of chemotherapeutic agents, certain pathogenic species of organisms which were formerly not considered to be of importance have acquired resistance to those commercial cephalosporin drugs, said pathogenic organisms including certain organisms belonging to the genera of Escherichia and Citrobacter, a large majority of organisms belonging to the genera of Proteus, Enterobacter and Serratia and those belonging to the genus Pseudomonas. [cf. Warren E. Wick, Cephalosporins and Penicillins: Chemistry and Biology, chapter 11, ed. E. H. Flynn, 1972, Academic Press]

It is, therefore, desirable to provide a new cephalosporin drug which would also have clinically useful activity against those pathogenic bacteria, i.e. with a broadened antimicrobial spectrum over the cephalosporin drugs in use today.

Under the circumstances, we have synthesized a large number of new cephalosporin derivatives and examined their pharmaceutical properties. Now we have succeeded in synthesizing new cephalosporin derivatives, their salts and esters and have found that those compounds are inhibitory to a large variety of bacterial strains including gram-positive bacteria and gram-negative bacteria.

Some salient characterics of these new cephalosporin derivatives are as follows.

Thus, a preferred group of cephalosporin derivatives of this invention not only display clinically or practically useful activity against gram-positive bacteria such as Staphylococcus aureus but also inhibitory to a broad spectrum of gram-negative bacteria such as Escherichia coli, Klebsiella pneumoniae, Proteus vulgaris, Proteus mirabilis, Proteus morganii, Proteus rettgeri, Citrobacter freundii, Enterobacter cloacae and Serratia marcescens. This advantageous feature is particularly evident when those new derivatives are used against those mutant strains of the above-mentioned species which possess $\beta$-lactamase (cephalosporinase) and are resistant to the commercial cephalosporins.

In the cephalosporin derivatives of this invention, $Y^1$ is hydrogen, hydroxyl, acyloxy, carbamoyloxy, quaternary ammonium or nitrogen-containing heterocyclic thio, or a nucleophilic compound residue equivalent thereto. The acyloxy group is preferably a group of the formula —OT wherein T may for example be an aliphatic carbonyl or aromatic carbonyl group containing 2 to 10 carbon atoms, such as acetyl, propionyl, butyuyl, benzoyl, etc. T may stand for one of the reactive acyl groups disclosed in German Laid-Open Patent Applications (OLS) P 2607064 and P 2619243, such as 3-oxobutyryl, 3-carboxypropionyl, 2-carboxybenzoyl, 2-(N-carboethoxycarbamoyl)benzoyl, 2-(N-carboethoxysulfamoyl)benzoyl, 2-carboxy-2(or 6)-nitrobenzoyl, etc. In so far as antimicrobial activity is concerned, acetyl is the most desirable species of the substituent group T and none of the above-mentioned reactive acyl groups contributes as much to the activity of derivatives [I] as does acetyl. However, as will be described hereinafter, compounds of the formula [I] having such reactive acyl groups are more beneficial than compounds [I] having acetyl in the reaction with a tertiary amine corresponding to the quaternary ammonium group or a nitrogen-containing heterocyclic thiol, or a salt thereof.

The quaternary ammonium group may be a substituted or unsubstituted pyridinium group of the formula:

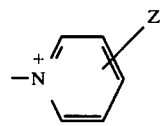

[wherein Z may for example be hydrogen, an alkyl of 1 to 4 carbon atoms (e.g. methyl, etc.), carbamoyl, carboxyl, sulfo or an alkoxy of 1 to 4 carbon atoms (e.g. methoxy etc.)]. Thus, there may be mentioned pyridinium, carbamoyl-substituted pyridinium (e.g. 3-carbamoylpyridinium, 4-carbamoylpyridinium, etc.), sulfo-substituted pyridinium (e.g. 4-sulfopyridinium etc.), alkyl-substituted pyridinium (e.g. 3-methylpyridinium, 4-methylpyridinium, etc.), carboxy-substituted pyridinium (e.g. 3-carboxypyridinium, 4-carboxypyridinium, etc.) and so on. The quaternary ammonium group may also be quinolinium, picolinium, lutidinium or the like. The preferred quaternary ammonium group is pyridinium which is either unsubstituted or substituted by carbamoyl in the 4-position of the pyridinium ring.

Where the cephalosporin derivative of this invention has a quaternary ammonium group, it may assume a betaine structure which may for example be represented by the following formula:

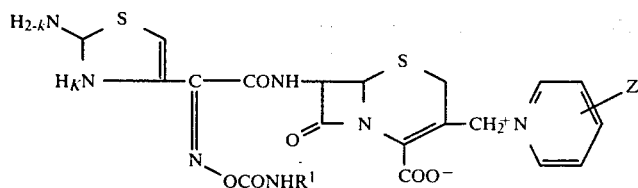

[wherein k, $R^1$ and Z have the same meanings as respectively defined hereinbefore].

The nitrogen-containing heterocyclic thio group may also be represented by the formula —S-Het wherein Het means a 5-membered or 6-membered heterocyclic ring containing one to 4 nitrogen atoms, which ring may further include oxygen or sulfur atoms, said nitrogen atom or atoms or atoms may be in the oxide form and said heterocyclic group (hetero-ring) may optionally be substituted.

As examples of said nitrogen-containing heterocyclic group there may be mentioned six-membered heterocyclic groups such as those including one nitrogen atom, e.g. pyridyl or N-oxopyridyl and those including two nitrogen atoms, e.g. pyrimidyl, pyridazinyl, N-oxopyridazinyl, etc.; and five-membered heterocyclic groups containing two nitrogen atoms such as pyrazolyl, diazolyl etc., those including one nitrogen atom and one sulfur atom, e.g. thiazolyl, etc., those including two nitrogen atoms and one sulfur atom, e.g. 1,2,3-thiadiazolyl, 1,2,4-thiadiazolyl, 1,3,4-thiadiazolyl, 1,2,5-thiadiazolyl, etc., those including two nitrogen atoms and one oxygen atom, e.g. 1,2,3-oxadiazolyl, 1,2,4-oxadiazolyl, 1,3,4-oxadiazolyl, 1,2,5-oxadiazolyl, etc., those including 3 nitrogen atoms, e.g. 1,2,3-triazolyl, 1,2,4-triazolyl, etc. and those including 4 nitrogen atoms, e.g. 1H-tetrazolyl, 2H-tetrazolyl, etc.

Such nitrogen-containing heterocyclic groups may have substituents, the number of which is preferably one or two substituents per each nitrogen-containing heterocyclic group, said substituents being exemplified by alkyl($C_{1-4}$) groups such as methyl, ethyl, propyl, isopropyl, butyl, isobutyl, etc.; haloalkyls ($C_{1-4}$) such as trifluoromethyl. etc.; aryl($C_{6-10}$) group such as phenyl, naphthyl, etc.; alkenyl($C_{2-5}$) groups such as vinyl, allyl, etc. lower alkoxy($C_{1-4}$) groups such as methoxy, ethoxy, propoxy, isopropoxy, butoxy, etc.; halogens such as chlorine, bromine, etc.; hydroxyl; mercapto; amino; carboxyl; carbamoyl; groups of the formula —X-$Z^1$ [where X is an alkylene($C_{2-5}$) group; $Z^1$ is a substituent such as hydroxyl, mercapto, amino, mono- or di-alkyl($C_{1-4}$) amino groups (e.g. dimethylamino, monoethylamino, etc.), guanyl, carboxyl, sulfo, carbamoyl, alkoxy($C_{1-4}$) carbonyl groups (e.g. methoxycarbonyl, ethoxycarbonyl, etc.), mono- or di-alkyl($C_{1-4}$)carbamoyl groups (e.g. N,N-dimethylcarbamoyl, etc.), alkoxy($C_{1-4}$) groups (e.g. methoxy, ethoxy, n-propoxy, etc.), alkyl($C_{1-4}$)thio groups (e.g. methylthio, etc.), alkyl($C_{1-4}$)sulfonyl groups (e.g. methylsulfonyl, etc.), alkyl($C_{1-4}$)carbonyl groups (e.g. acetyl, n-propionyl, etc.), etc.]; groups of the formula —S-$Z^2$ [where $Z^2$ is, for example, an alkyl($C_{1-4}$) group or a group of the above-mentioned formula —X-$Z^1$] and groups of the formula

[where $Z^3$ and $Z^4$, respectively, mean an alkyl($C_{1-4}$) group, a group of the above formula —X-$Z^1$, alkoxy($C_{1-4}$) carbonyl groups (e.g. methoxycarbonyl, etc.), alkyl($C_{1-4}$) carbonyl groups (e.g., acetyl, etc.), carbamoyl, mono- or di-alkyl($C_{1-4}$)carbamoyl groups (e.g. N,N-dimethylcarbamoyl, etc.) and so forth].

As exemplary species of the group —X-$Z^1$, there may be mentioned carboxymethyl, carbamoylmethyl, mono- or di-alkyl($C_{1-4}$) carbamoylmethyl(e.g. N,N-dimethylcarbamoylmethyl, etc.), hydroxyalkyl($C_{1-4}$) groups (e.g. hydroxymethyl, 2-hydroxyethyl, etc.), alkyl($C_{1-4}$)carbonyloxyalkyl($C_{1-4}$) groups (e.g. acetoxymethyl, 2-acetoxyethyl, etc.), alkoxy($C_{1-4}$)carbonylmethyl (e.g. methoxycarbonylmethyl, etc.), methylthiomethyl, methylsulfonylmethyl, aminomethyl, mono- or di-alkyl($C_{1-4}$) aminoalkyl($C_{1-4}$) groups (e.g. N,N-dimethylaminomethyl, N-methylaminoethyl, N,N-dimethylaminoethyl, etc.), sulfomethyl, sulfoethyl and so on.

As exemplary substituents of the formula —S-$Z^2$ which may be present on the hetero-rings, there may be mentioned methylthio, 2-hydroxyethylthio, 2-acetoxyethylthio, carboxymethylthio, alkoxy ($C_{1-4}$)carbonylmethylthio (e.g. methoxycarbonylmethylthio, etc.), carbamoylmethylthio, N,N-dimethylcarbamoylthio, acetylmethylthio, 2-sulfoethylthio and so on.

As exemplary substituents of the formula

which may be present on the aforementioned hetero-rings, there may be mentioned mono- or di-alkyl($C_{1-4}$)amino group (e.g. methylamino, etc.), sulfoalkyl($C_{1-4}$)amino groups (e.g. 2-sulfoethylamino, etc.), hydroxyalkyl($C_{1-4}$)amino groups (e.g. 2-hydroxyethylamino, etc.), mono- or di-alkyl($C_{1-4}$)aminoalkyl($C_{1-4}$)amino groups (e.g. 2-dimethylaminoethylamino, etc.), alkyl($C_{1-4}$)carbonylamino groups (e.g. acetylamino, etc.), 2-dimethylaminoacetylamino, alkoxy($C_{1-4}$)carbonylamino groups (e.g. methoxycarbonylamino, etc.) and so on.

Some of the important classes of said nitrogen-containing heterocyclic thio group $Y^1$ are as follows.

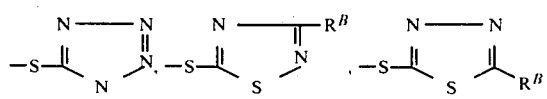

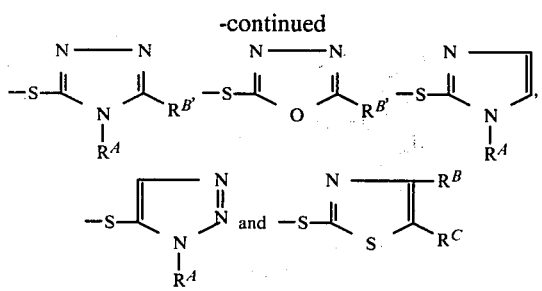

In the above formulas, $R^A$ is hydrogen or a group of the formula $-(CH_2)_nP$ [n is an integer of 1 to 3; P is hydrogen, hydroxyl, alkoxy($C_{1-4}$), alkyl($C_{1-4}$)thio, a group of the formula $-COOR^4$ (where $R^4$ is hydrogen or alkyl($C_{1-4}$)), a group of the formula

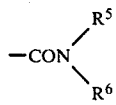

(where each of $R^5$ and $R^6$ is hydrogen or alkyl ($C_{1-4}$)) or a group of the formula

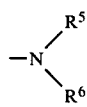

(where $R^5$ and $R^6$ are as defined above)]; and $R^B$ and $R^C$ may be the same or different and each represents hydrogen, amino, carbamoyl, a group of the formula $-NHCOOR^7$ ($R^7$ is an alkyl($C_{1-4}$)), a group of the formula $-S-(CH_2)_nQ$ (wherein n is an integer of 1 to 3; and Q is carboxyl, hydroxyl, hydrogen or sulfo) or a group of the formula $-(CH_2)_nP$ (n and P have the same meanings as hereinbefore defined).

In the above description, the term alkyl($C_{1-4}$), alkoxy ($C_{1-4}$), aryl($C_{6-10}$), alkenyl($C_{2-5}$) mean alkyl groups of 1 to 4 carbon atoms, alkoxy groups of 1 to 4 carbon atoms, aryl groups of 6 to 10 carbon atoms and alkenyl groups of 2 to 5 carbon atoms, respectively.

An interesting class of substituents $Y^1$ includes acetoxy, carbamoyloxy and groups belonging to the above-mentioned important classes of nitrogen-containing heterocyclic thio groups.

The most interesting species and classes of substituents $Y^1$ include acetoxy, carbamoyloxy, 1,2,3-triazol-4-ylthio, 3-substituted-1,2,4-thiadiazol-5-ylthio, 2-substituted-1,3,4-oxadiazol-5-ylthio, 1-substituted-imidazol-2-ylthio, 1-substituted-1H-tetrazol-5-ylthio, 2-substituted-1,3,4-thiadiazol-5-ylthio, 3,4-di-substituted-1,2,4-triazol-5-ylthio and 4-substituted-thiazol-2-ylthio. The substituent group designated by the term "substituted" in the immediately preceding description mean hydrogen, methyl, carboxymethyl, hydroxymethyl, hydroxyethyl, carbamoylmethyl, 2-N,N-dimethylaminoethyl, methoxymethyl or ethoxycarbonylmethyl, and the two substituents in 3,4-disubstituted-1,2,4-triazol-5-ylthio may be the same or different.

Referring to general formula [I], $R^2$ in $-COOR^2$ is hydrogen or an ester residue. Recently it is an important consideration to make penicillins and cephalosporins available in oral dosage forms or in the form of suppositories, and many reports are available on procedures which generally comprise transforming the free carboxyl groups of penicillins or cephalosporins into esters so as to reduce the acidity and enhance the lipid solubility of such carboxylic acids, thereby increasing the absorption thereof from the intestinal tract, and let the antibiotic agents display their antibiotic activity in vivo as those ester residues are cleaved off by the hydrolytic attack of endogenous esterase [cf. Binderup et al, J. Antibiotics 24, 767(1971).]. The ester residue $R^2$ in this invention may be any of such esters as will be useful for the above purpose.

Thus, ester residues which are conducive to increase concentrations in the blood upon administration by the oral or rectal route are desirably selected for $R^2$ in accordance with this invention. As examples of ester residue $R^2$, there may be mentioned alkoxy($C_{1-4}$) alkyl($C_{1-4}$) groups such as methoxyethyl, ethoxymethyl, isopropoxymethyl, α-methoxyethyl, α-ethoxyethyl, α-alkoxyethyl, etc.; alkyl($C_{1-4}$) thiomethyl groups such as methylthiomethyl, isopropylthiomethyl, etc.; acyl($C_{1-6}$) oxyalkyl ($C_{1-4}$)groups such as pivaloyloxymethyl, etc.; alkoxy($C_{1-4}$) carbonyloxymethyl groups such as 1-(ethoxycarbonyloxy)ethyl, etc.; acyl($C_{1-4}$) oxyethoxymethyl groups such as 2-n-propionyloxyethoxymethyl; and acyl($C_{1-6}$) oxyaralkyl ($C_{7-10}$) groups such as α-n-butyryloxybenzyl, 3-methoxy-4-acetyloxybenzyl, etc.

Among those ester residues, pivaloyloxymethyl and 1-(ethoxycarbonyloxy)ethyl are particularly desirable. The acyl group as referred to above is desirably an alkylcarbonyl group. The terms acyl($C_{1-6}$), acyl($C_{1-4}$) and aralkyl($C_{7-10}$) as used in the above description mean acyl groups of 1 to 6 carbon atoms acyl groups of 1 to 4 carbon atoms and aralkyl groups of 7 to 10 carbon atoms. (The same applies hereinafter).

In the above-mentioned cephalosporin derivatives [I], $R^1$ is preferably an alkyl($C_{1-6}$), aralkyl($C_{7-10}$) or aryl($C_{6-12}$) group. As examples of said alkyl group, there may be mentioned straight-chain alkyl groups such as methyl, ethyl, n-propyl, n-butyl, n-pentyl, n-hexyl, etc.; branched alkyl groups such as isopropyl, isobutyl, sec.-butyl, tert.-butyl, isopentyl, neopentyl, tert.-pentyl, etc.; and cyclic alkyl groups such as cyclopentyl, cyclohexyl, etc. The aralkyl group may for example be benzyl, phenethyl, phenylpropyl or phenylbutyl. The aryl group includes phenyl.

The especially preferred species of $R^1$ are methyl, ethyl, n-propyl, isopropyl, butyl, isopropyl and cyclohexyl.

Among the compounds represented by the general formula [I] and pharmaceutically acceptable salts thereof, the compounds of which $R^1$ is methyl and pharmaceutically acceptable salts thereof are the most valuable in view of the strong antibacterial activities and low production cost.

In the preceding paragraph, the terms alkyl ($C_{1-6}$) and aryl($C_{6-12}$) mean alkyl groups of 1 to 6 carbon atoms and aryl groups of 6 to 12 carbon atoms, respectively. (The same definitions apply hereinafter). It should also be understood that, throughout this specification, all alkyls, alkyl moieties of alkoxy groups, and alkylene moieties of aralkyl groups may be straight-chain, branched or cyclic, although straight-chain and branched species are preferred.

The most desirable class of the cephalosporin derivatives of this invention are the derivatives in which $Y^1$ is a group belonging to the aforementioned "most interesting class", $R^1$ is methyl, ethyl or propyl and $R^2$ is hydrogen, pivaloyloxymethyl or 1-(ethoxycarbonyloxy)ethyl and pharmacologically acceptable salts of said derivatives.

The compounds [I] according to this invention can be employed in antibacterial applications, as the free compounds, free zwitterion compounds or other forms, e.g. salts. For medicinal purposes, the salts are desirably pharmacologically acceptable salts. As examples of such salts there may be mentioned salts with non-toxic cations such as sodium, potassium, etc.; basic amino acids such as arginine, ornithine, lysine, histidine, etc.; salts with polyhydroxyalkylamines such as N-methylglucucamine, diethylamine, triethanolamine, tris-hydroxylmethylaminomethane, etc.; salts with inorganic acids such as hydrochloric acid, sulfuric acid, nitric acid, phosphoric acid, etc.; salts with organic acids such as oxalic acid, fumaric acid, maleic acid, tartaric acid, etc.; and salts which are commonly used in the field of penicillins and cephalosporins.

The compounds [I] according to this invention may assume the two tautomeric forms by the tautomerization shown by the following formulas.

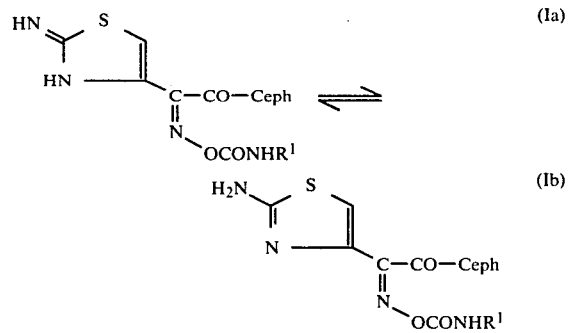

(wherein Ceph means

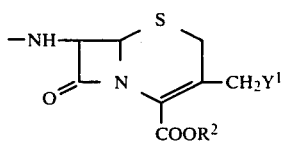

$R^1$ has the meaning defined hereinbefore.)

Thus, the formula [Ia] corresponds to the case in which $k=1$ in formula [I] and the formula [Ib] corresponds to the case in which $k=0$ in formula [I].

Much study has been done on the modes of existence of compounds of this type and the literature refers to thiazoline forms in certain instances (G. J. Kruger and G. Gafner, Acta Cryst. B 27, 326(1971); J. M. Vandenbelt and L. Doub. J. Am. Chem. Soc. 66, 1633(1944) but refers to thiazole forms in other instances (L. M. Werbel, Chem. & Ind., 1966, 1634). However, because the cephalosporin derivatives of this invention are stabilized in the thiazoline form by the contribution of a hydrogen bond as shown by the formula given below, thiazoline forms appear to be invariably predominant.

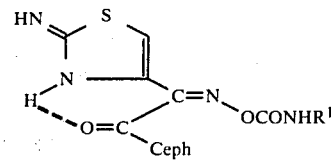

[wherein the symbols have the same meanings as respectively defined hereinbefore).

As it is often true with this kind of equilibrial relationship, however, the above equilibrium is subject to transient changes due to the conditions under which the cephalosporin derivatives of this invention are present, such as the pH of the solution, the polarity of the solvent, temperature, type of substituent and others. Therefore, notwithstanding the appropriateness of designating them by any of the names of thiazoline and thiazole, the cephalosporin derivatives of this invention are all designated herein by the names of thiazoline forms. This invention encompasses all of the above-mentioned tautomeric forms.

The cephalosporin derivatives of this invention are distinguished from the isomers with a different orientation of their oximino groups. The orientations of such oximino group are differently named in its relation with the intramolecular amide linkage. Thus, "syn" refers to the partial structure represented by:

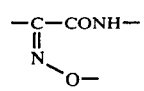

and "anti" refers to the partial structure represented by:

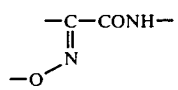

While the cephalosporin derivatives of this invention are syn-isomers, this invention encompasses mixtures containing any of such syn-isomers, for example any optional mixtures of the above-described syn and anti-isomers.

The cephalosporin derivatives of this invention are broadspectrum cephalosporins, that is to say cephalosporins which are not only active against gram-positive bacteria but also highly inhibitory to a broad range of clinically important gram-negative bacteria. The cephalosporin derivatives according to this invention are low in toxicity and can be safely administered or applied. Just as the commercial cephalosporin antibiotics, these derivatives are administered by routine procedures, either as they are or in admixture with pharmacologically acceptable carriers or vehicles, in such dosage forms as powders, solutions, suspensions, tablets, capsules, suppositories and so forth. Those cephalosporin derivatives of this invention wherein $R^2$ is an ester residue are desirably administered by the oral route, while injections (intramuscular or intravenous) are generally preferred dosage forms for the derivatives wherein $R^2$ is not an ester residue. The pharmacologically acceptable carriers and vehicles may be the known materials such as excipients for injections (e.g. water, physiological saline, etc.) and excipients for oral preparations (e.g.

lactose, sucrose, starch, cellulose, calcium sulfate, gelatin, etc.). The preparation of the abovementioned dosage forms may be carried out by procedures known per se.

The cephalosporin derivatives according to this invention can be used as disinfectants or as prophylactic or therapeutic agents in the management of bacterial infections in man and other animals (rat, mouse, dog, rabbit, horse, monkey, etc.), either as they are or as formulated into the above-mentioned dosage forms. The bacterial infections mentioned above mean the infectious diseases caused by the bacteria mentioned hereinbefore and include, among others, purulent or supurative diseases, respiratory organ infections, bile duct infections, intestinal tract infections, urinary tract infections and gyneco-obsteric infections.

The dosage cannot be stated in general terms because it depends upon the kind of disease, condition and other factors, with individual differences among hosts being another influencing factor. By way of example, for the prevention or treatment of urinary tract infections, cephalosporin derivatives of this invention are intramusculary or intravenously administered to adult human at the daily dose level of about 20 to 50 mg/kg, in 3 to 4 divided doses daily.

By taking advantage of their antibacterial activity, the cephalosporin derivatives of this invention can be used as disinfectants for the purpose of removing both the above-mentioned and the under-mentioned bacteria from surgical instruments, hospital wards, drinking water and other quarters, article, or materials. The object can be accomplished, for example by allowing surgical instruments to stand in an aqueous solution of the present cephalosporin derivative (concentration: 1000 μg/ml) at room temperature for a couple of days.

The cephalosporin derivatives of this invention can be produced by procedures known per se.

By way of example, such a derivative can be produced by reacting a 2-(syn)carbamoyloximinoacetamide compound of the formula:

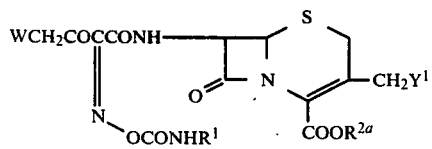

[wherein W is halogen (e.g. chlorine or bromine); $Y^1$ and $R^1$ have the same meanings as respectively defined hereinbefore; $R^{2a}$ is hydrogen, an ester residue or an anion] or a salt thereof with thiourea and, if desired, esterifying the reaction product to a [2-(syn)-carbamoyloximinoacetamido]-cephalosporin of the formula:

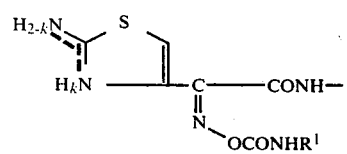

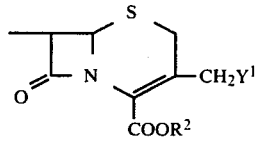

[wherein $R^2$, k, $R^1$ and $Y^1$ have the meanings respectively defined hereinbefore] or a salt thereof. In the above formulas, the ester residue represented by $R^{2a}$ may be any of the residues mentioned by way of example in connection with $R^2$.

The amount of thiourea cannot be stated in geneal terms because it depends on the reaction conditions employed, for instance, but normally, thiourea is used in a proportion of 1.0 to 5.0 moles per mole of starting compound [II] or a salt thereof. This reaction can be effected by admixing starting compound [II] or a salt thereof with thiourea at a temperature within the range of about 0° to about 80° C. The reaction is preferably carried out in a solvent. The solvent may be any solvent that will not intefere with the contemplated reaction, although the so-called polar aprotic solvents such as dimethylformamide, dimethylacetamide, dimethylsulfoxide, acetonitrile, hexamethylphosphoramide, etc. as well as mixtures thereof are particularly advantageous. The salts of compounds [II] include the salts of their basic groups with acids and the salts of their strongly acidic groups with alkali metals or organic bases. Thus, they may be salts with the acids or bases which have hereinbefore been mentioned in connection with the salts of compounds [I].

When the reaction of thiourea with compound [II] or a salt thereof yields a compound of the formula:

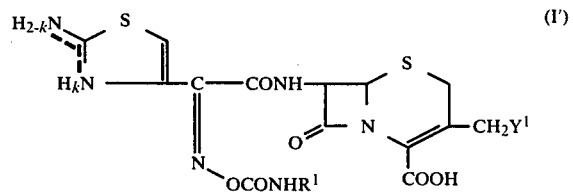

[wherein $Y^1$, k and $R^1$ have the same meanings as previously defined] or a salt thereof, the 4-carboxyl group of [I'] may optionally be esterified to produce the corresponding ester. The ester residues useful for this purpose have already been described hereinbefore in connection with formula [I]. The esterification may be carried out by procedures known per se. Various methods for esterification have been well established in the field of cephalosporins, and they can be adopted for the purposes of this invention. For example, it is a desirable practice to esterify the compound [I'] or a salt thereof [which may be one of the salts with the acids of bases mentioned in connection with formula [I]] with a compound of the formula:

[wherein $R^{2c}$ is an ester residue as defined hereinbefore in connection with formula [I]] a salt thereof or a reactive derivative thereof. The reactive derivative mentioned just above is preferably a halide of the formula:

[wherein R[2c] is defined hereinbefore; Hal means a halogen atom which is preferably iodine, bromine or chlorine].

Where the 4-carboxyl group of compound [I'] is free or where compound [I'] is an acid addition salt, the reaction between compound [I'] and Hal-R[2c] is desirably conducted in the presence of a suitable acid acceptor (for example, inorganic bases such as sodium hydrogen carbonate, potassium hydrogen carbonate, etc.; and organic amines such as dicyclohexylamine, N-ethylaniline, N,N-diethylaniline, N-methylmorpholine, pyridine, triethylamine, etc.). The amount of said base may be equimolar or more with respect to compound [I'] or acid addition salt thereof.

The esterification reaction is conducted normally in a solvent inert to the reaction. As examples of the solvent, there may be mentioned amide solvents, halogenated hydrocarbon solvents, sulfoxide solvents, ketone solvents, nitrile solvents and liquefied sulfur dioxide. Thus, for example, acetonitrile, N,N-dimethylformamide (DMF), N,N-dimethylacetamide (DMA), dichloromethane, chloroform, dimethylsulfoxide (DMSO), dioxane, tetrahydrofuran (THF), acetone, methyl ethyl ketone, etc. may be mentioned. Among these solvents, DMF, acetone, acetonitrile and liquefied sulfur dioxide are particularly desirable.

The esterification reaction is generally conducted at a temperature between 20° C. and −20° C. When liquefied sulfur dioxide has been chosen as the solvent, the reaction is carried out in the neighborhood of its boiling point, i.e. −10° C. to −20° C. The reaction time varies considerably with the activity of the alkyl halide employed, physicochemical properties, particularly the bulkiness, of $Y^1$ in compound [I'] or salt thereof and the polarity of the solvent employed, although the reaction generally goes to completion in 10 minutes to 120 hours. The product compound can be isolated and purified by procedures known per se, such as extraction with a solvent, change of pH, phasic transfer, crystallization, recrystallization, chromatography and so on.

By the above esterification, the carboxyl group at the 4 position is converted to an esterified carboxyl group. While the esterification reaction is involved in the method described hereafter, too, it may be carried out in the above manner.

The cephalosporin derivatives of this invention may also be produced by way of nucleophilic substitution reaction. The cephalosporin derivative of formula [I] wherein $Y^1$ is hydroxyl, quaternary ammonium or nitrogen-containing heterocyclic thio can be produced in the following manner. Thus, a [2-(syn)-carbamoyloximinoacetamido]cephalosporin of the formula:

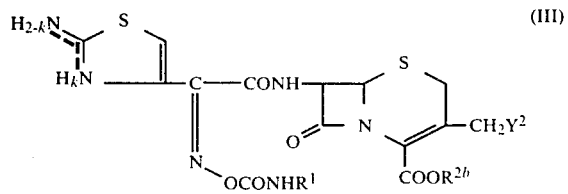

(III)

[wherein k and $R^1$ have the same meanings as respectively defined hereinbefore; $Y^2$ is an acyloxy group; $R^{2b}$ is hydrogen atom] or a salt thereof is reacted with water, a tertiary amine (or a salt thereof) or a nitrogen-containing heterocyclic thiol (or a salt thereof) and, if desired, the reaction product is further esterified to obtain a [2-(syn)-carbamoyloximinoacetamido]-cephalosporin of the formula:

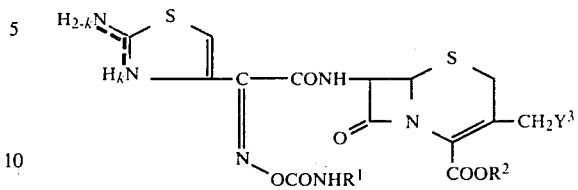

[wherein k, $R^1$ and $R^2$ have the same meanings as respectively defined hereinbefore; $Y^3$ is hydroxyl, quaternary ammonium or nitrogen-containing heterocyclic thio] or a salt thereof.

The acyloxy group $Y^2$ may be one of the reactive acyls mentioned hereinbefore. Thus, for example, acetyloxy, 3-oxobutryloxy, 3-carboxypropionyloxy, 2-carboxybenzoyloxy, 2-(N-carboethoxycarbamoyl)benzoyloxy, 2-(N-carboethoxysulfamoyl)-benzoyloxy, 2-carboxy-3(or 6)-nitrobenzoyloxy, etc. may be mentioned. The starting material compound [III] may be used either in its free form or in the form of a salt. The salt may be one of the salts with the acid or base material in connection with the compound [I].

This nucleophilic substitution reaction, when one limits himself to the 3-position of the cephem ring which is the site of transformation, may be regarded as a reaction essentially the same as the nucleophilic substitution reaction of a 3-acyloxy group described in the prior art patent and other literature (e.g. E. H. Flynn (ed.), Cephalosporins and Penicillins, Chapter 4, Section 5, p. 151, 1972, Academic Press; Japanese Patent Publication No. 17936/1964, Japanese Patent Publication No. 26972/1964; Japanese Patent Publication No. 11283/1968) and, therefore, may be carried out by those known procedures or by procedures analogous thereto.

The reaction of compound [III] or a salt thereof with water proceeds as a hydrolytic reaction which is known per se. This hydrolysis reaction is normally conducted at a temperature between −20° C. and 50° C., preferably in the presence of a base such as sodium hydroxide or potassium hydroxide. In the presence of a base, the reaction normally goes to completion within 48 hours.

The tertiary amine which is reacted with compound [III] or a salt thereof is an amine corresponding to the aforementioned quaternary ammonium group. Therefore, the tertiary amine encompasses pyridines of the formula:

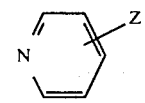

[wherein Z is as defined hereinbefore], quinoline, picoline, lutidine, etc. The tertiary amine is normally used in a proportion of 1.0 to 20.0 moles per mole of compound [III] or a salt thereof. Normally the reaction temperature is about 0° to 100° C. The reaction is desirably carried out in a solvent. Preferred solvents are water and mixtures of water with organic solvents such as dimethylformamide, dioxane, dimethylacetamide, acetone, methanol, ethanol, dimethylsulfoxide, acetonitrile, tetrahydrofuran, etc. The reaction normally goes to completion within 48 hours.

Referring to the reaction of compound [III] or a salt thereof with said nitrogen-containing heterocyclic thiol or a salt thereof, this nitrogen-containing heterocyclic thiol is represented by the formula:

HS—Het

[wherein Het is as defined hereinbefore].

The nitrogen-containing heterocyclic thiol, which is among the employable nucleophilic compounds, may be used in the free form but more advantageously in the form of a salt, e.g. an alkali metal (sodium, potassium or the like) salt. This reaction is desirably conducted in a solvent. For example, water and organic solvents which are readily miscible with water and will not react with the starting material compounds, such as dimethylformamide, dimethylacetamide, dioxane, acetone, alcohol, acetonitrile, dimethylsulfoxide, tetrahydrofuran, etc. may be mentioned.

While the reaction temperature and time are dependent on the starting materials used, the solvent, etc., the reaction is conducted at 0° L to 100° C. for a few fractions of an hour to several days. The reaction is conducted usually at a pH value between 2 to 8 and, preferably, in the neighborhood of neutrality, at pH 4 to 7. In certain cases, addition of a surface-active quaternary ammonium salt such as trimethylbenzylammonium bromide, triethylbenzylammonium bromide or triethylbenzylammonium hydroxide to the reaction system may allow the reaction to proceed more smoothly. Advantageous results are also obtained when the reaction is conducted in an inert atmosphere, such as nitrogen gas, to prevent atmospheric oxidation. The nitrogen-containing heterocyclic thiol or a salt thereof is desirably used in a proportion of about 1 to 5 moles per mole of compound [III] or a salt thereof.

The nitrogen-containing heterocyclic thiol may be produced by procedures known per se or procedures analogous thereto, the known procedures including those described in Heterocyclic Chemistry (A. R. Katritzky and J. M. Lagowsky, John Willey and Sons, 1960), Chapter 5; Heterocyclic Compounds Vol. 8 (R. C. Enterfield (ed.), John Willey and Sons, 1967) Chapter I; Advances in Heterocyclic Chemistry, Vol. 9 (A. R. Katritzky and A. J. Boulton (ed.), Academic Press, 1968) pp. 165–209; and Dai Yuki Kagaku (Munio Kotake (ed.), Asakura Shoten), Vol. 15, for instance. Furthermore, the functional group or groups other than thiol in the heterocyclic thiol produced by the procedure known per se or by one of the above-mentioned procedures may be transformed according to reaction(s) known per se.

The esterificaton reaction included in the above-mentioned method as an optional step may be conducted in the same manner as described above.

The cephalosporin derivative of this invention may also be produced by reacting a compound of the formula [IV]:

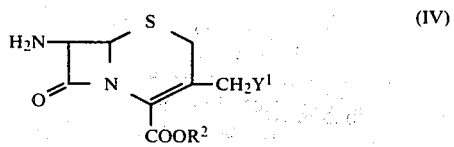

(IV)

[wherein $R^2$ and $Y^1$ have the same meanings as respectively defined hereinbefore] or a salt thereof with a carboxylic acid of formula [V]:

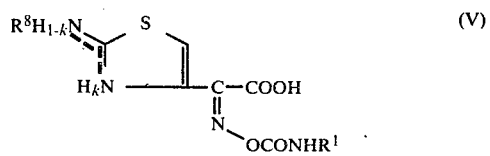

(V)

[wherein $R^8$ is hydrogen or a protective group; k and $R^1$ have the same meanings as respectively defined hereinbefore] or a reactive derivative thereof and, if desired, esterifying the reaction product.

The protective group $R^8$ may expediently be one of the known amino- or imino-protecting groups. Thus, for example, trytyl, formyl, alkyl($C_{1-4}$) carbonyl (e.g. acetyl, propionyl, etc.), alkoxy($C_{1-4}$) carbonyl (e.g. t-butoxycarbonyl, etc.), substituted alkyl($C_{1-4}$) carbonyl (e.g. chloroacetyl, etc.), alkoxy($C_{1-4}$) alkyl($C_{1-4}$) carbonyl (e.g. methoxyacetyl, methoxypropionyl, etc.), substituted alkoxy($C_{1-4}$) carbonyl (e.g. trichloroethoxycarbonyl, etc.), aralkyl($C_{7-10}$) oxycarbonyl (e.g. benzyloxycarbonyl, etc.), substituted aralkyl($C_{7-10}$) oxycarbonyl (e.g. p-nitrobenzyloxycarbonyl, etc.) and proton may be mentioned.

The compound of formula [V] is used in the reaction, either in the form of a free carboxylic acid or in the form of a salt or as a reactive derivative thereof. The salt may be one of alkali metal salts (sodium, potassium, calcium and other salts) and organic amine salts (trimethylamine, pyridine and other salts). As examples of said reactive derivative, there may be mentioned the corresponding acid halides (e.g. acid chloride, acid bromide, etc.), acid anhydride, mixed acid anhydrides (e.g. acid anhydrides with aliphatic($C_{1-5}$) carboxylic acids such as mixed acid anhydrides with carbonic acid monoesters e.g. monomethyl carbonate, monoisobutyl carbonate, etc.), active esters (e.g. the corresponding p-nitrophenyl ester, 2,4-dinitrophenyl ester, N-hydroxysuccinimide ester, etc.) and so on.

The reaction using the compound [V] or a salt thereof is carried out in the presence of a dehydrating agent. As examples of the dehydrating agent there may be mentioned N,N'-di-substituted carbodiimides (e.g. N,N'-dicyclohexylcarbodiimide, etc.), azolides (e.g. N,N'-carbonylimidazole, etc.), N,N'-thionyldiimidazole, 2-chloropyridiniummethyl iodide, phosphorous oxychloride, etc.

The reaction is normally conducted in a suitable solvent. As examples of such solvent there may be mentioned organic and inorganic solvents, including halogenated hydrocarbons such as chloroform, methylene chloride, etc.; ethers such as tetrahydrofuran, dioxane, etc.; dimethylformamide; acetone; water; etc, as well as mixtures of such solvents.

While the amount of compound [V], a salt thereof or a reactive derivative thereof cannot be stated in general terms, it is normally used in a proportion of 1 to 5 moles, preferably from 1 to 2 moles per mole of compound [IV]. The reaction temperature is normally in the range of about −50° C. to 40° C. The reaction time may normally be about 1 to 10 hours. When the compound [V] is used in the form of an acid halide, the reaction is preferably conducted in the presence of a suitable acid acceptor (e.g. sodium hydroxide, sodium hydrogen carbonate, etc.). The esterification reaction which is an optional step in this method may be carried out in the same manner as the esterification reaction described hereinbefore. After the reaction has been completed, the protective group is removed, if desired. The removal of the protective group may be carried out by procedures known per se [Japanese Patent Application Laid-open No. 52083/1975; Pure and Applied Chemistry 7, 335 (1963)]. For example, t-butoxycarbonyl can be removed with dilute hydrochloric acid, and monochloroacetyl can be removed with thiourea.

When the cephalosporin derivative of this invention has been obtained in the form of a free compound, it can be converted to a salt in the per se conventional manner. When it has been obtained in the form of a salt, it can be transformed to the free compound or a different salt according to the per se conventional manner.

From the reaction mixture, the cephalosporin derivative of this invention can be isolated or purified by procedures known per se (e.g. phasic transfer, concentration, chromatography, crystallization, recrystallization, etc.).

The compound of formula [II] or a salt thereof can be produced by procedures known per se, inclusive of those disclosed in Japanese Patent Application Laid-Open No. 95293/1975, No. 11093/1975 and No. 56487/1976 and Japanese Patent Application No. 108101/1976, or by procedures analogous thereto.

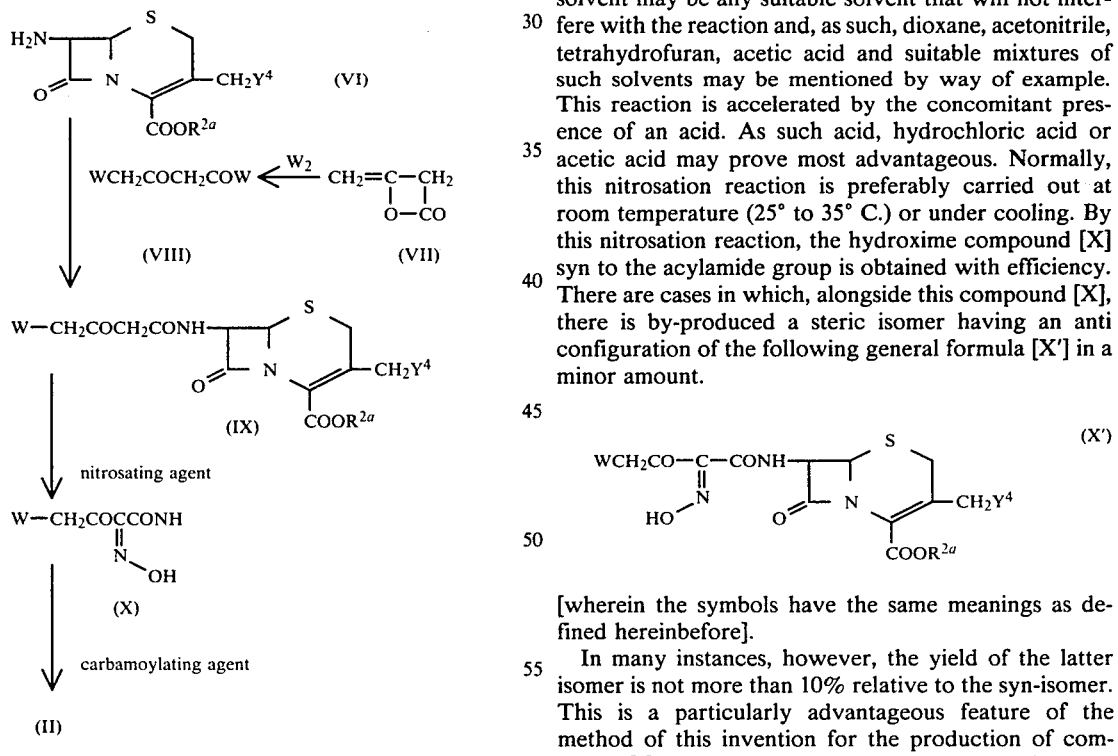

[In the above formulas, W and $R^{2a}$ have the same meanings as respectively defined hereinbefore; $Y^4$ is hydrogen, hydroxyl, carbamoyloxy, acyloxy, quaternary ammonium or nitrogen-containing heterocyclic thio].

First, the halogen $W_2$, preferably chlorine or bromine, is reacted with a diketene illustrated by the formula [VII]. The proportions of halogen and diketene may be equimolar. The resultant compound [VIII] is further reacted with compound [VI] or a salt thereof. The compound [VI] or a salt thereof may be produced by a known procedure or a procedure analogous thereto [cf. Japanese Patent Application Laid-open No. 11782/1976, German Patent Application Laid-Open (OLS) No. P 2607064 and No. 2619243). Thus, an 7-acylamino-3-acetoxymethyl-3-cephem-4-carboxylic acid or 7-acylamino-3-hydroxymethyl-3-cephem-4-carboxylic acid or a salt thereof is subjected to a transformation reaction to convert the substituent in 3-position thereof to —$CH_2Y^4$($Y^4$ has the same meaning as defined hereinbefore) and, then, the acyl group in 7-position is removed. Alternatively, an 7-amino-3-reactive acyloxymethyl-3-cephem-4-carboxylic acid (the reactive acyl as defined hereinbefore for T) or a salt thereof is reacted with a tertiary amine (corresponding to the quaternary ammonium group) or a nitrogen-containing heterocyclic thiol. The resultant compound [IX] or a salt thereof (which may be the salt of an acid or base which has been described in connection with compound [I]) is reacted with a nitrosating agent. As examples of the nitrosating agent, there may be mentioned acid, nitrous acid esters (e.g. methyl nitrite, ethyl nitrite, amyl nitrite, etc.), nitrosyl chloride, etc. Among those agents, nitrous acid is produced in the reaction system as an alkali metal nitrite reacts with an acid such as hydrochloric acid, phosphoric acid or acetic acid, and the thus produced nitrous acid is used as the nitrosating agent. This nitrosation reaction is preferably carried out in a solvent. This solvent may be any suitable solvent that will not interfere with the reaction and, as such, dioxane, acetonitrile, tetrahydrofuran, acetic acid and suitable mixtures of such solvents may be mentioned by way of example. This reaction is accelerated by the concomitant presence of an acid. As such acid, hydrochloric acid or acetic acid may prove most advantageous. Normally, this nitrosation reaction is preferably carried out at room temperature (25° to 35° C.) or under cooling. By this nitrosation reaction, the hydroxime compound [X] syn to the acylamide group is obtained with efficiency. There are cases in which, alongside this compound [X], there is by-produced a steric isomer having an anti configuration of the following general formula [X'] in a minor amount.

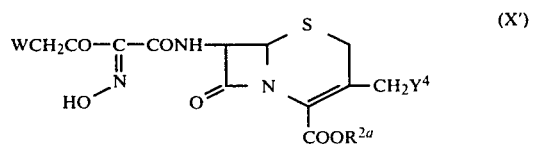

[wherein the symbols have the same meanings as defined hereinbefore].

In many instances, however, the yield of the latter isomer is not more than 10% relative to the syn-isomer. This is a particularly advantageous feature of the method of this invention for the production of compound [I] having the same syn-orientation as the compound [X]. The compound [X] thus obtained may be isolated and purified by conventional procedures such as solvent extraction, pH change, phasic transfer, crystallization, chromatography, etc. The resultant compound [X] or a salt thereof is then reacted with a carbamoylating agent to produce a compound of formula [II] or a salt thereof. The salt of compound [X] and of [II] may each be the salt with one of the acids and bases described in connection with compounds of formula [I].

The carbamoylating agent may be a known agent. For example, isocyanate compounds of the formula:

$$R^1NCO$$

[wherein $R^1$ has the same meaning as defined hereinbefore] may be employed. Thus, there may be mentioned straight-chain alkyl($C_{1-6}$) isocyanates such as methyl isocyanate, ethyl isocyanate, propyl isocyanate, butyl isocyanate, pentyl isocyanate, hexyl isocyanate, etc.; branched alkyl($C_{1-5}$) isocyanates such as isopropyl isocyanate, isobutyl isocyanate, sec.-butyl isocyanate, tert.-butyl isocyanate, isopentyl isocyanate, neopentyl isocyanate, tert.-pentyl isocyanate, etc.; cyclic alkyl($C_{3-6}$) isocyanates such as cyclopentyl isocyanate, cyclohexyl isocyanate, etc.; and aralkyl($C_{7-10}$) isocyanates such as phenylmethyl isocyanate, phenylethyl isocyanate, phenylpropyl isocyanate, etc.

This reaction is carried out in the presence or absence of a solvent and in the presence or absence of a catalyst, normally at a temperature within the range of $-30°$ to $100°$ C.

The solvent useful for the purposes of this process may be any organic solvent that will not interfere with the reaction. As examples of such solvents there may be mentioned ketones, e.g. diethyl ketone, methyl ethyl ketone, acetone, etc.; nitriles, e.g. propionitrile, acetonitrile, etc.; ethers, e.g. tetrahydrofuran, dioxane, etc.; amides such as dimethylformamide, dimethylacetamide, etc.; esters, e.g. ethyl acetate, propyl acetate, etc.; halogenated hydrocarbons, e.g. methylene chloride, chloroform, etc.; hexamethylphosphorotriamide; and other inert organic solvents.

In the practice of this invention, such an isocyanate may be employed in a proportion ranging from an equivalent relative to starting material to the solvent amount, although it is preferably used in a proportion of 1.1 moles to 10 moles per mole of the starting material.

In the method according to this invention, the reaction time may be reduced by adding a catalyst. As examples of the catalyst which can thus be employed, there may be mentioned tertiary amines such as N-methylmorpholine, N-ethylmorpholine, N-(3-dimethylaminopropyl)morpholine, triethylamine, N-methylpiperidine, N,N,N',N'-tetramethyl-1,3-propanediamine, N,N,N',N',N''-pentamethyldiethylenediamine, bis-(2-diethylaminoethyl)adipate, bis-(2-dimethylaminoethyl)adipate, N,N-dimethylcyclohexylamine, N,N-diethylcyclohexylamine, N-methyl-N-octylcyclohexylamine, N-methyl-N-dodecylcyclohexylamine, N-methyl-N-(2-ethylhexyl)cyclohexylamine, N-methyldicyclohexylamine, 1,4-diazabicyclo(2,2,2)octane, quinine, pyridine, N,N,N',N'-tetramethyl-1,3-butanediamine, etc.; inorganic tin compounds such as stannic chloride, stannous chloride, etc.; and organometal compounds, particularly organotin compounds such as tetrabutyltin, tetraphenyltin, tributyltin acetate, dimethyltin dichloride, dibutyltin diacetate, dibutyltin dichloride, dibutyltin dilaurate, dibutyltin dilaurylmercaptide, bis(2-ethylhexyl)tin oxide, dibutyltin sulfide, dibutyltin dioctanoate, ferric acetylacetonate, etc.

The reaction temperature for this reaction process may be varied over a broad range according to the solvent, the amount of said isocyanate compound, the type and amount of catalyst, the type of starting compound, etc. Generally, however, the reaction is conducted at a temperature between $-30°$ C. and $100°$ C., preferably within the range of $10°$ to $50°$ C.

The above-mentioned isocyanate compounds may be either known compounds or those produced by the known methods of synthesis (for example, Organic Functional Group Preparations I, 305(1971), S. R. Sandler, W. Karo et al, Academic Press.).

In the above production method, where $Y^4$ in compound [X] includes any of the functional groups mentioned below, the functional group reacts with the isocyanate compound to give a compound [II] having a group $Y^1$ which is different from $Y^4$.

Where $Y^4$ has a —OH group, it reacts with the isocyanate $R^1$—NCO to yield a compound [II] having a —OCONHR$^1$ group for $Y^1$; where $Y^4$ has a —SH group, it reacts with the isocyanate $R^1$—NCO to yield a compound [II] having a —SCONHR$^1$ group for $Y^1$, and where $Y^4$ has an —NH$_2$ group, the reaction yields a compound [II] wherein $Y^1$ is —NHCONHR$^1$.

Where $Y^4$ of compound [X] has a structure which will not react the isocyanate compound under the above-mentioned conditions, $Y^4$ is identical with $Y^1$.

The compound of formula [V] may be produced by known procedures, procedures known per se or procedures analogous thereto. For example, [V] can be produced by reacting an ester (e.g. benzhydryl ester) of compound of the formula:

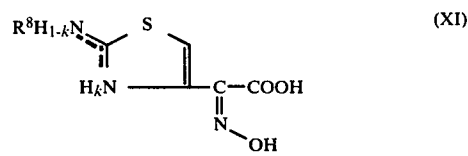

(XI)

[wherein the symbols have the same meanings as defined hereinbefore] with $R^1NCO$ by the procedure described hereinbefore in connection with the reaction of compound [X] with a carbamoylating agent or procedures analogous thereto and, then, removing the ester residue with an acid (e.g. trifluoroacetic acid/anisole). The compound of formula [XI] may be produced by known procedures or procedures analogous thereto.

As examples of the product compounds of this invention having the formula:

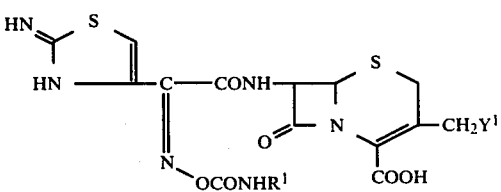

there may be mentioned the compounds represented by the following structures as well as the pharmacologically acceptable salts (particularly the sodium salts and hydrochlorides) thereof.

| $R^1$ | $Y^1$ |
|---|---|
| —CH$_3$ | —OCOCH$_3$ |
| —CH$_3$ | —OCONH$_2$ |
| —CH$_3$ | —H |
| —CH$_3$ | 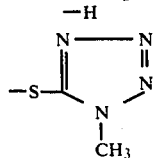 |

-continued

| $R^1$ | $Y^1$ |
|---|---|
| —CH₃ | —S-(tetrazole)-N-C₂H₅ |
| —CH₃ | —S-(tetrazole)-N-CH₂OCH₃ |
| —CH₃ | —S-(tetrazole)-N-CH₂SCH₃ |
| —CH₃ | —S-(tetrazole)-N-CH₂CH₂OH |
| —CH₃ | —S-(tetrazole)-N-CH₂COONa |
| —CH₃ | —S-(tetrazole)-N-CH₂CH₂COONa |
| —CH₃ | —S-(tetrazole)-N-CH₂CH₂SO₃Na |
| —CH₃ | —S-(tetrazole)-N-CH₂CONH₂ |
| —CH₃ | —S-(tetrazole)-N-CH₂CON(CH₃)₂ |
| —CH₃ | —S-(tetrazole)-N-CH₂CH₂NH₂ |
| —CH₃ | —S-(tetrazole)-N-CH₂CH₂NHCH₃ |
| —CH₃ | —S-(tetrazole)-N-CH₂CH₂N(CH₃)₂ |
| —CH₃ | —S-(tetrazole)-N-CH₂CH₂NHCOCH₃ |
| —CH₃ | —S-(tetrazole)-N-(CH₂)₃N(CH₃)₂ |
| —CH₃ | —S-(tetrazole)-N-CH₂—CH=CH₂ |
| —CH₃ | —S-(tetrazole)-N-CH₂SO₃Na |
| —CH₃ | —S-(tetrazole)-N-H |
| —CH₃ | —S-(thiadiazole)-CH₃ |
| —CH₃ | —S-(thiadiazole)-CF₃ |
| —CH₃ | —S-(thiadiazole)-CH₂OCH₃ |
| —CH₃ | —S-(thiadiazole)-CH₂SCH₃ |
| —CH₃ | —S-(thiadiazole)-CH₂SO₂CH₃ |
| —CH₃ | —S-(thiadiazole)-CH₂N(CH₃)₂ |
| —CH₃ | —S-(thiadiazole)-CH₂CH₂N(CH₃)₂ |
| —CH₃ | —S-(thiadiazole)-CH₂CONH₂ |
| —CH₃ | —S-(thiadiazole)-CH₂CON(CH₃)₂ |

-continued

| R¹ | Y¹ |
|---|---|
| —CH₃ | thiadiazole-S— with —CH₂COONa |
| —CH₃ | thiadiazole-S— with —CH₂COOCH₃ |
| —CH₃ | thiadiazole-S— with —NH₂ |
| —CH₃ | thiadiazole-S— with —NHCOOCH₃ |
| —CH₃ | thiadiazole-S— with —NHCH₂CH₂OH |
| —CH₃ | thiadiazole-S— with —NHCH₂CH₂N(CH₃)₂ |
| —CH₃ | thiadiazole-S— with —CH₂CON(CH₃)₂ |
| —CH₃ | thiadiazole-S— with —NHCH₂CH₂SO₃Na |
| —CH₃ | thiadiazole-S— with —CH₂COCH₃ |
| —CH₃ | thiadiazole-S— with —SCH₂CH₂OH |
| —CH₃ | thiadiazole-S— with —SCH₂CH₂N(CH₃)₂ |
| —CH₃ | thiadiazole-S— with —SCH₂CONH₂ |
| —CH₃ | thiadiazole-S— with —SCH₂CON(CH₃)₂ |
| —CH₃ | thiadiazole-S— with —SCH₂COONa |
| —CH₃ | thiadiazole-S— with —SCH₂CH₂SO₃Na |
| —CH₃ | thiadiazole-S— with —SCH₂COOC₂H₅ |
| —CH₃ | thiadiazole-S— with —SCH₂CH₂SO₂CH₃ |

-continued

| R¹ | Y¹ |
|---|---|
| —CH₃ | thiadiazole-S— with —CH₂OH |
| —CH₃ | thiadiazole-S— with —NHCH₃ |
| —CH₃ | thiazole-S— with =N—C(CH₃)= (ring) |
| —CH₃ | thiazole-S— with —CH₃ |
| —CH₃ | thiazole-S— with —CH₃, —CH₃ |
| —CH₃ | thiazole-S— with —CH₃, —CH₃ |
| —CH₃ | thiazole-S— with —CH₂COONa |
| —CH₃ | oxazole-S— with —CH₃, —CH₃ |
| —CH₃ | N-methyl thiazoline-S— |
| —CH₃ | oxazole-S— with —CH₃ |
| —CH₃ | triazole-S— (NH) |
| —CH₃ | N-methyl triazole-S— |
| —CH₃ | N-methyl imidazole-S— with —CH₃ |
| —CH₃ | N-methyl triazole-S— with —COOH |
| —CH₃ | N-methyl triazole-S— with —CH₂OH |

-continued
| $R^1$ | $Y^1$ |
|---|---|
| —CH₃ | 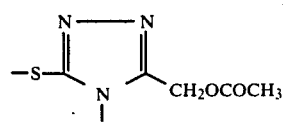 |
| —CH₃ | 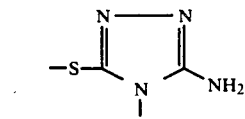 |
| —CH₃ | 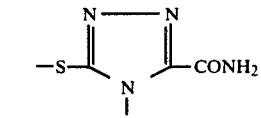 |
| —C₂H₅ | —OCOCH₃ |
| —C₂H₅ | —OCONH₂ |
| —C₂H₅ | —H |
| —C₂H₅ | 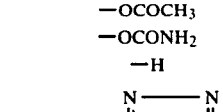 |
| —C₂H₅ | 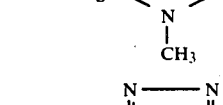 |
| —C₂H₅ | 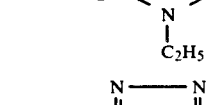 |
| —C₂H₅ | 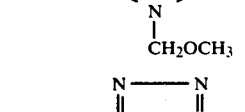 |
| —C₂H₅ | 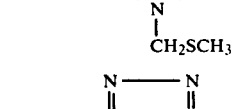 |
| —C₂H₅ | 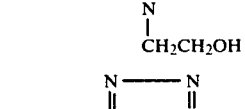 |
| —C₂H₅ | 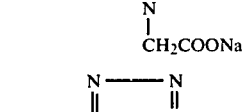 |
| —C₂H₅ | 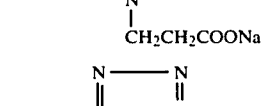 |
-continued
| $R^1$ | $Y^1$ |
|---|---|
| —C₂H₅ | 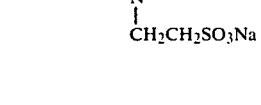 |
| —C₂H₅ |  |
| —C₂H₅ | 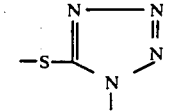 |
| —C₂H₅ | 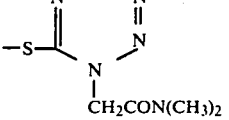 |
| —C₂H₅ | 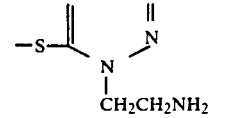 |
| —C₂H₅ | 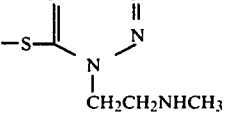 |
| —C₂H₅ | 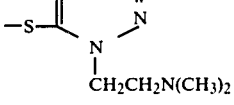 |
| —C₂H₅ | 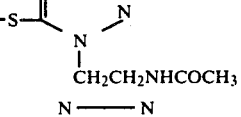 |
| —C₂H₅ | 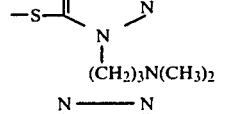 |
| —C₂H₅ | 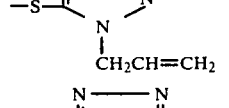 |
| —C₂H₅ | 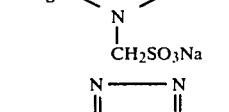 |
| —C₂H₅ | 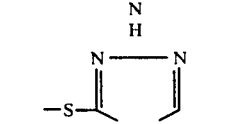 |
| —C₂H₅ | 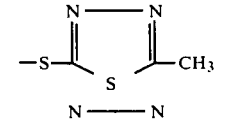 |
| —C₂H₅ | 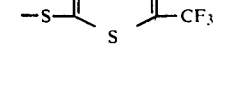 |
| —C₂H₅ |  |

25

-continued

| R¹ | Y¹ |
|---|---|
| —C₂H₅ |  |
| —C₂H₅ |  |
| —C₂H₅ | —S—(N═N / S)—CH₂SO₂CH₃ |
| —C₂H₅ | —S—(N═N / S)—CH₂N(CH₃)₂ |
| —C₂H₅ | —S—(N═N / S)—CH₂CH₂N(CH₃)₂ |
| —C₂H₅ | —S—(N═N / S)—CH₂CONH₂ |
| —C₂H₅ | —S—(N═N / S)—CH₂CON(CH₃)₂ |
| —C₂H₅ | —S—(N═N / S)—NHCH₂CH₂SO₃Na |
| —C₂H₅ | —S—(N═N / S)—CH₂COCH₃ |
| —C₂H₅ | —S—(N═N / S)—SCH₂CH₂OH |
| —C₂H₅ | —S—(N═N / S)—SCH₂CH₂N(CH₃)₂ |
| —C₂H₅ | —S—(N═N / S)—SCH₂CONH₂ |
| —C₂H₅ | —S—(N═N / S)—SCH₂CON(CH₃)₂ |
| —C₂H₅ | —S—(N═N / S)—SCH₂COONa |
| —C₂H₅ | —S—(N═N / S)—SCH₂CH₂SO₃Na |
| —C₂H₅ | —S—(N═N / S)—SCH₂COOC₂H₅ |
| —C₂H₅ | —S—(N═N / S)—SCH₂CH₂SO₂CH₃ |

26

-continued

| R¹ | Y¹ |
|---|---|
| —C₂H₅ | —S—(N═N / S)—CH₂OH |
| —C₂H₅ | —S—(N═N / S)—NHCH₃ |
| —C₂H₅ |  |
| —C₂H₅ |  |
| —C₂H₅ |  |
| —C₂H₅ |  |
| —C₂H₅ |  |
| —C₂H₅ |  |
| —C₂H₅ |  |
| —C₂H₅ |  |
| —C₂H₅ |  |
| —C₂H₅ |  |

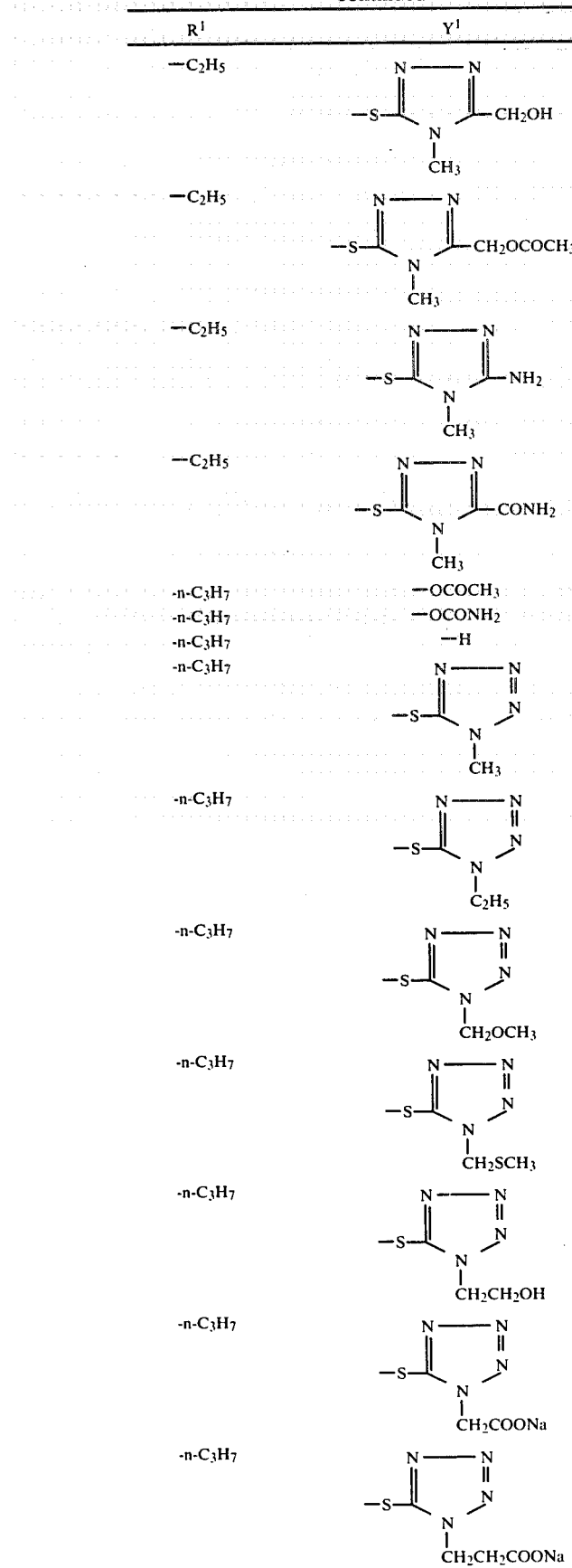
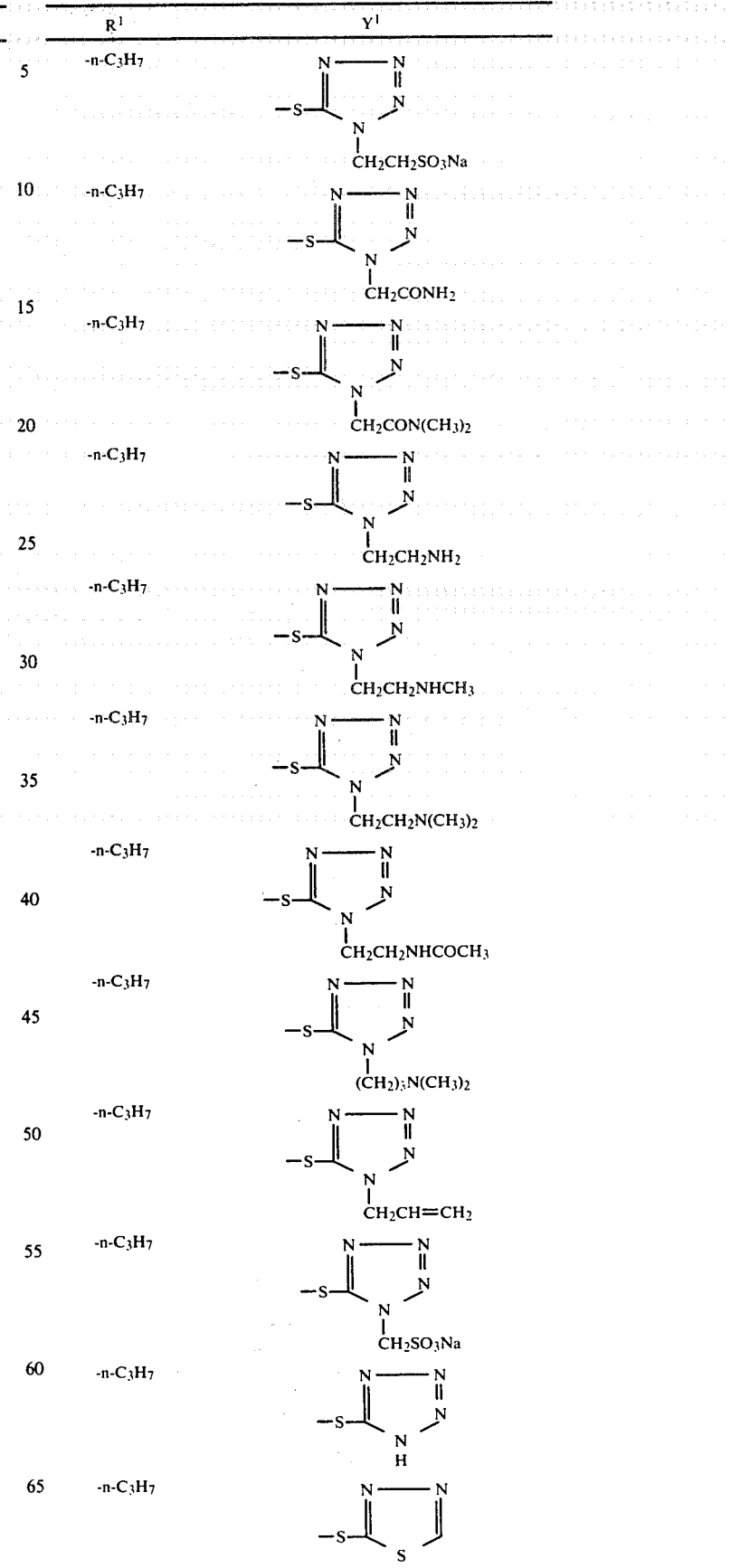

| R¹ | Y¹ |
|---|---|
| -n-C₃H₇ | 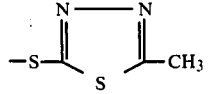 |
| -n-C₃H₇ |  |
| -n-C₃H₇ | 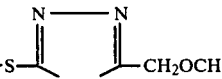 |
| -n-C₃H₇ | 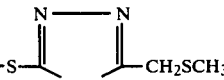 |
| -n-C₃H₇ | 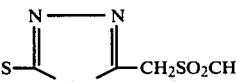 |
| -n-C₃H₇ | 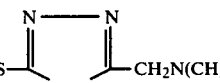 |
| -n-C₃H₇ | 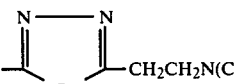 |
| -n-C₃H₇ | 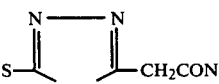 |
| -n-C₃H₇ | 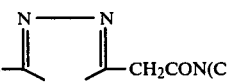 |
| -n-C₃H₇ | 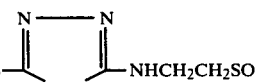 |
| -n-C₃H₇ | 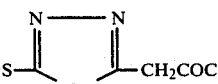 |
| -n-C₃H₇ | 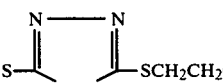 |
| -n-C₃H₇ |  |
| -n-C₃H₇ | 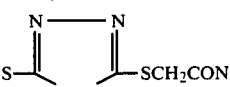 |
| -n-C₃H₇ | 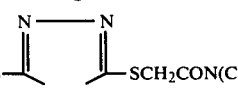 |
| -n-C₃H₇ |  |
| -n-C₃H₇ | 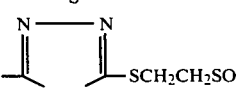 |
| R¹ | Y¹ |
|---|---|
| -n-C₃H₇ |  |
| -n-C₃H₇ | 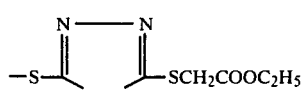 |
| -n-C₃H₇ | 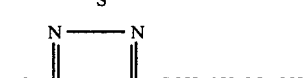 |
| -n-C₃H₇ | 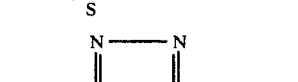 |
| -n-C₃H₇ | 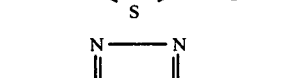 |
| -n-C₃H₇ | 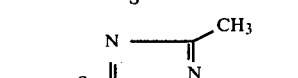 |
| -n-C₃H₇ | 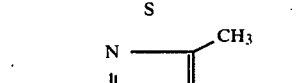 |
| -n-C₃H₇ | 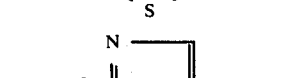 |
| -n-C₃H₇ | 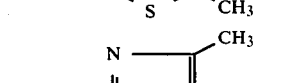 |
| -n-C₃H₇ |  |
| -n-C₃H₇ | 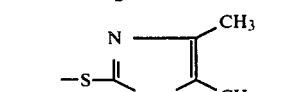 |
| -n-C₃H₇ | 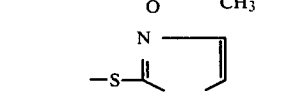 |
| -n-C₃H₇ | 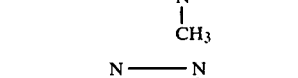 |
| -n-C₃H₇ | 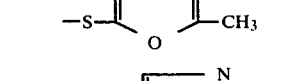 |

4,200,575

-continued

| $R^1$ | $Y^1$ |
|---|---|
| -n-C$_3$H$_7$ | 5-(1-methyl-1,2,4-triazol-3-yl-COOH)thio [triazole with N-CH$_3$, COOH substituent] |
| -n-C$_3$H$_7$ | [1-methyl-1,2,4-triazol-3-ylthio with CH$_2$OH] |
| -n-C$_3$H$_7$ | [1-methyl-1,2,4-triazol-3-ylthio with CH$_2$OCOCH$_3$] |
| -n-C$_3$H$_7$ | [1-methyl-1,2,4-triazol-3-ylthio with NH$_2$] |
| -n-C$_3$H$_7$ | [1-methyl-1,2,4-triazol-3-ylthio with CONH$_2$] |
| -i-C$_3$H$_7$ | —OCOCH$_3$ |
| -i-C$_3$H$_7$ | —OCONH$_2$ |
| -i-C$_3$H$_7$ | —H |
| -i-C$_3$H$_7$ | [1-methyl-tetrazol-5-ylthio, N-CH$_3$] |
| -i-C$_3$H$_7$ | [1-ethyl-tetrazol-5-ylthio, N-C$_2$H$_5$] |
| -i-C$_3$H$_7$ | [tetrazol-5-ylthio, N-CH$_2$OCH$_3$] |
| -i-C$_3$H$_7$ | [tetrazol-5-ylthio, N-CH$_2$SCH$_3$] |
| -i-C$_3$H$_7$ | [tetrazol-5-ylthio, N-CH$_2$CH$_2$OH] |
| -i-C$_3$H$_7$ | [tetrazol-5-ylthio, N-CH$_2$COONa] |
| -i-C$_3$H$_7$ | [tetrazol-5-ylthio, N-CH$_2$CH$_2$COONa] |
| -i-C$_3$H$_7$ | [tetrazol-5-ylthio, N-CH$_2$CH$_2$SO$_3$Na] |
| -i-C$_3$H$_7$ | [tetrazol-5-ylthio, N-CH$_2$CONH$_2$] |
| -i-C$_3$H$_7$ | [tetrazol-5-ylthio, N-CH$_2$CON(CH$_3$)$_2$] |
| -i-C$_3$H$_7$ | [tetrazol-5-ylthio, N-CH$_2$CH$_2$NH$_2$] |
| -i-C$_3$H$_7$ | [tetrazol-5-ylthio, N-CH$_2$CH$_2$NHCH$_3$] |
| -i-C$_3$H$_7$ | [tetrazol-5-ylthio, N-CH$_2$CH$_2$N(CH$_3$)$_2$] |
| -i-C$_3$H$_7$ | [tetrazol-5-ylthio, N-CH$_2$CH$_2$NHCOCH$_3$] |
| -i-C$_3$H$_7$ | [tetrazol-5-ylthio, N-(CH$_2$)$_3$N(CH$_3$)$_2$] |
| -i-C$_3$H$_7$ | [tetrazol-5-ylthio, N-CH$_2$CH=CH$_2$] |
| -i-C$_3$H$_7$ | [tetrazol-5-ylthio, N-CH$_2$SO$_3$Na] |
| -i-C$_3$H$_7$ | [tetrazol-5-ylthio, N-H] |

-continued

| R¹ | Y¹ |
|---|---|
| -i-C₃H₇ | -S-(1,3,4-thiadiazol-2-yl) |
| -i-C₃H₇ | -S-(5-methyl-1,3,4-thiadiazol-2-yl) |
| -i-C₃H₇ | -S-(5-trifluoromethyl-1,3,4-thiadiazol-2-yl) |
| -i-C₃H₇ | -S-(5-methoxymethyl-1,3,4-thiadiazol-2-yl) |
| -i-C₃H₇ | -S-(5-methylthiomethyl-1,3,4-thiadiazol-2-yl) |
| -i-C₃H₇ | -S-(5-methylsulfonylmethyl-1,3,4-thiadiazol-2-yl) |
| -i-C₃H₇ | -S-(5-dimethylaminomethyl-1,3,4-thiadiazol-2-yl) |
| -i-C₃H₇ | -S-(5-(2-dimethylaminoethyl)-1,3,4-thiadiazol-2-yl) |
| -i-C₃H₇ | -S-(5-carbamoylmethyl-1,3,4-thiadiazol-2-yl) |
| -i-C₃H₇ | -S-(5-(N,N-dimethylcarbamoylmethyl)-1,3,4-thiadiazol-2-yl) |
| -i-C₃H₇ | -S-(5-(N-(2-sulfonatoethyl)amino)-1,3,4-thiadiazol-2-yl), Na salt |
| -i-C₃H₇ | -S-(5-acetonyl-1,3,4-thiadiazol-2-yl) (−CH₂COCH₃) |
| -i-C₃H₇ | -S-(5-(2-hydroxyethylthio)-1,3,4-thiadiazol-2-yl) |
| -i-C₃H₇ | -S-(5-(2-dimethylaminoethylthio)-1,3,4-thiadiazol-2-yl) |
| -i-C₃H₇ | -S-(5-(carbamoylmethylthio)-1,3,4-thiadiazol-2-yl) |
| -i-C₃H₇ | -S-(5-(N,N-dimethylcarbamoylmethylthio)-1,3,4-thiadiazol-2-yl) |
| -i-C₃H₇ | -S-(5-(sodium carboxymethylthio)-1,3,4-thiadiazol-2-yl) (−SCH₂COONa) |
| -i-C₃H₇ | -S-(5-(2-sulfonatoethylthio)-1,3,4-thiadiazol-2-yl), Na salt |
| -i-C₃H₇ | -S-(5-(ethoxycarbonylmethylthio)-1,3,4-thiadiazol-2-yl) |
| -i-C₃H₇ | -S-(5-(2-methylsulfonylethylthio)-1,3,4-thiadiazol-2-yl) |
| -i-C₃H₇ | -S-(5-hydroxymethyl-1,3,4-thiadiazol-2-yl) |
| -i-C₃H₇ | -S-(5-methylamino-1,3,4-thiadiazol-2-yl) |
| -i-C₃H₇ | -S-(4-methylthiazol-2-yl) |
| -i-C₃H₇ | -S-(5-methylthiazol-2-yl) |
| -i-C₃H₇ | -S-(4,5-dimethylthiazol-2-yl) |
| -i-C₃H₇ | -S-(4-(sodium carboxymethyl)thiazol-2-yl) |
| -i-C₃H₇ | -S-(4,5-dimethyloxazol-2-yl) |
| -i-C₃H₇ | -S-(1-methylimidazol-2-yl) |
| -i-C₃H₇ | -S-(5-methyl-1,3,4-oxadiazol-2-yl) |
| -i-C₃H₇ | -S-(1H-1,2,3-triazol-... yl) |
| -i-C₃H₇ | -S-(4-methyl-1,2,4-triazol-3-yl) |

-continued

| R¹ | Y¹ |
|---|---|
| -i-C₃H₇ | ![triazole with -S-, N-CH₃, CH₃ substituent] |
| -i-C₃H₇ | ![triazole with -S-, N-CH₃, COOH substituent] |
| -i-C₃H₇ | ![triazole with -S-, N-CH₃, CH₂OH substituent] |
| -i-C₃H₇ | ![triazole with -S-, N-CH₃, CH₂OCOCH₃ substituent] |
| -i-C₃H₇ | ![triazole with -S-, N-CH₃, NH₂ substituent] |
| -i-C₃H₇ | ![triazole with -S-, N-CH₃, CONH₂ substituent] |
| -n-C₄H₉ | —OCOCH₃ |
| -n-C₄H₉ | —OCONH₂ |
| -n-C₄H₉ | —H |
| -n-C₄H₉ | ![tetrazole with -S-, N-CH₃] |
| -n-C₄H₉ | ![tetrazole with -S-, N-C₂H₅] |
| -n-C₄H₉ | ![tetrazole with -S-, N-CH₂OCH₃] |
| -n-C₄H₉ | ![tetrazole with -S-, N-CH₂SCH₃] |
| -n-C₄H₉ | ![tetrazole with -S-, N-CH₂CH₂OH] |

-continued

| R¹ | Y¹ |
|---|---|
| -n-C₄H₉ | ![tetrazole with -S-, N-CH₂COONa] |
| -n-C₄H₉ | ![tetrazole with -S-, N-CH₂CH₂COONa] |
| -n-C₄H₉ | ![tetrazole with -S-, N-CH₂CH₂SO₃Na] |
| -n-C₄H₉ | ![tetrazole with -S-, N-CH₂CONH₂] |
| -n-C₄H₉ | ![tetrazole with -S-, N-CH₂CON(CH₃)₂] |
| -n-C₄H₉ | ![tetrazole with -S-, N-CH₂CH₂NH₂] |
| -n-C₄H₉ | ![tetrazole with -S-, N-CH₂CH₂NHCH₃] |
| -n-C₄H₉ | ![tetrazole with -S-, N-CH₂CH₂N(CH₃)₂] |
| -n-C₄H₉ | ![tetrazole with -S-, N-CH₂CH₂NHCOCH₃] |
| -n-C₄H₉ | ![tetrazole with -S-, N-(CH₂)₃N(CH₃)₂] |
| -n-C₄H₉ | ![tetrazole with -S-, N-CH₂CH=CH₂] |
| -n-C₄H₉ | ![tetrazole with -S-, N-CH₂SO₃Na] |

| $R^1$ | $Y^1$ |
|---|---|
| -n-C$_4$H$_9$ | 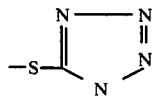 |
| -n-C$_4$H$_9$ | 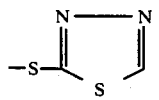 |
| -n-C$_4$H$_9$ | 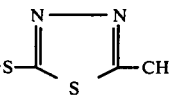 |
| -n-C$_4$H$_9$ | 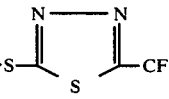 |
| -n-C$_4$H$_9$ | 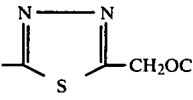 |
| -n-C$_4$H$_9$ | 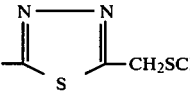 |
| -n-C$_4$H$_9$ | 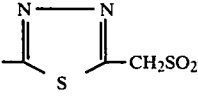 |
| -n-C$_4$H$_9$ | 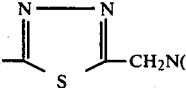 |
| -n-C$_4$H$_9$ | 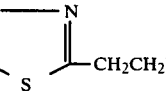 |
| -n-C$_4$H$_9$ | 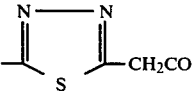 |
| -n-C$_4$H$_9$ | 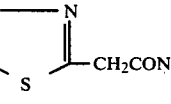 |
| -n-C$_4$H$_9$ | 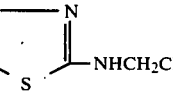 |
| -n-C$_4$H$_9$ | 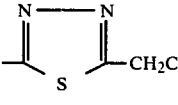 |
| -n-C$_4$H$_9$ | 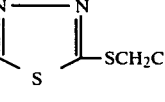 |
| -n-C$_4$H$_9$ | 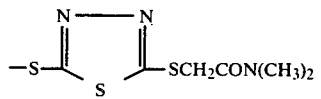 |
| $R^1$ | $Y^1$ |
|---|---|
| -n-C$_4$H$_9$ | 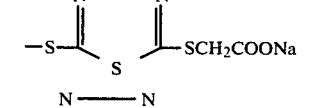 |
| -n-C$_4$H$_9$ | 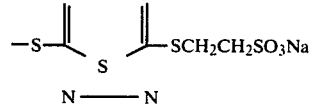 |
| -n-C$_4$H$_9$ | 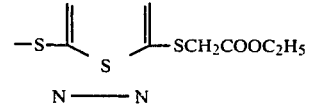 |
| -n-C$_4$H$_9$ | 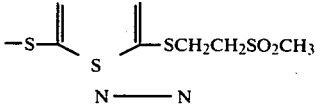 |
| -n-C$_4$H$_9$ | 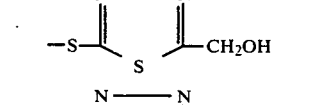 |
| -n-C$_4$H$_9$ | 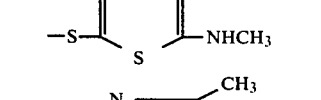 |
| -n-C$_4$H$_9$ | 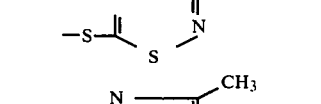 |
| -n-C$_4$H$_9$ | 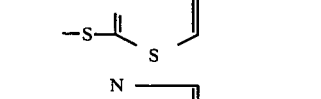 |
| -n-C$_4$H$_9$ | 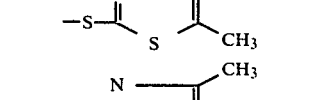 |
| -n-C$_4$H$_9$ | 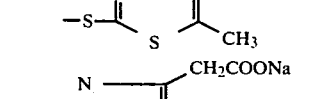 |
| -n-C$_4$H$_9$ | 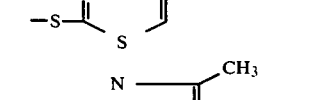 |
| -n-C$_4$H$_9$ | 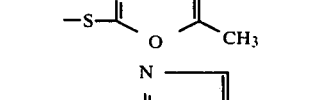 |
| -n-C$_4$H$_9$ | 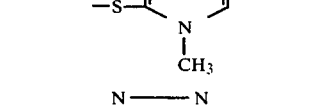 |

-continued
| R¹ | Y¹ |
|---|---|
| -n-C₄H₉ | 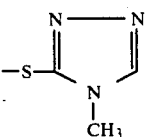 |
| -n-C₄H₉ | 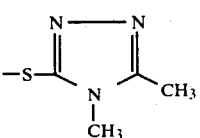 |
| -n-C₄H₉ | 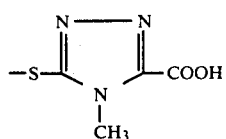 |
| -n-C₄H₉ | 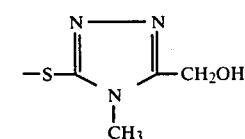 |
| -n-C₄H₉ | 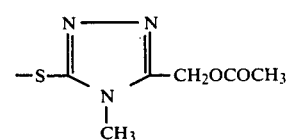 |
| -n-C₄H₉ | 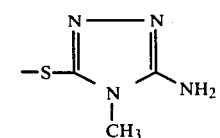 |
| -n-C₄H₉ | 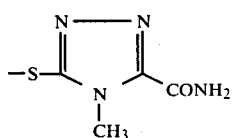 |
| —H | —OCOCH₃ |
| —H | —OCONH₂ |
| —H | —H |
| —H | 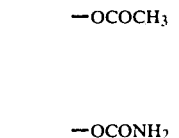 |
| —H | 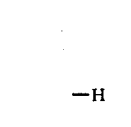 |
| —H |  |
| —H | 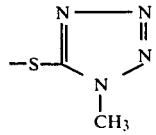 |
| —H | 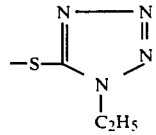 |
| —H | 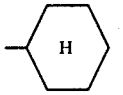 |
| —H | 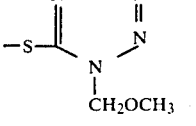 |
| —H | 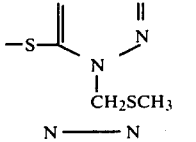 |
| —H | 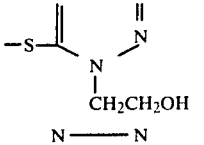 |
| —H | 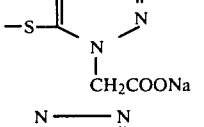 |
| —H | 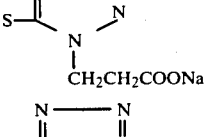 |
| —H | 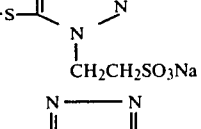 |
| —H | 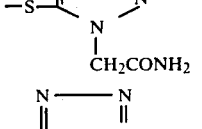 |
| —H | 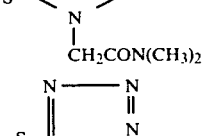 |
| —H | 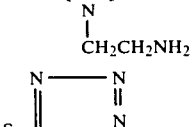 |

4,200,575

41

-continued

| R¹ | Y¹ |
|---|---|
| —H (cyclohexyl) | tetrazolyl-S— with N-(CH$_2$)$_3$N(CH$_3$)$_2$ |
| —H (cyclohexyl) | tetrazolyl-S— with N-CH$_2$CH=CH$_2$ |
| —H (cyclohexyl) | tetrazolyl-S— with N-H |
| —H (cyclohexyl) | tetrazolyl-S— with N-CH$_2$SO$_3$Na |
| —H (cyclohexyl) | thiadiazolyl-S— |
| —H (cyclohexyl) | thiadiazolyl-S—CH$_3$ |
| —H (cyclohexyl) | thiadiazolyl-S—CF$_3$ |
| —H (cyclohexyl) | thiadiazolyl-S—CH$_2$OCH$_3$ |
| —H (cyclohexyl) | thiadiazolyl-S—CH$_2$SCH$_3$ |
| —H (cyclohexyl) | thiadiazolyl-S—CH$_2$SO$_2$CH$_3$ |
| —H (cyclohexyl) | thiadiazolyl-S—CH$_2$N(CH$_3$)$_2$ |
| —H (cyclohexyl) | thiadiazolyl-S—CH$_2$CH$_2$N(CH$_3$)$_2$ |
| —H (cyclohexyl) | thiadiazolyl-S—CH$_2$CONH$_2$ |
| —H (cyclohexyl) | thiadiazolyl-S—CH$_2$CON(CH$_3$)$_2$ |

42

-continued

| R¹ | Y¹ |
|---|---|
| —H (cyclohexyl) | thiadiazolyl-S—NHCH$_2$CH$_2$SO$_3$Na |
| —H (cyclohexyl) | thiadiazolyl-S—CH$_2$COCH$_3$ |
| —H (cyclohexyl) | thiadiazolyl-S—SCH$_2$CH$_2$OH |
| —H (cyclohexyl) | thiadiazolyl-S—SCH$_2$CH$_2$N(CH$_3$)$_2$ |
| —H (cyclohexyl) | thiadiazolyl-S—SCH$_2$CONH$_2$ |
| —H (cyclohexyl) | thiadiazolyl-S—SCH$_2$CON(CH$_3$)$_2$ |
| —H (cyclohexyl) | thiadiazolyl-S—SCH$_2$COONa |
| —H (cyclohexyl) | thiadiazolyl-S—SCH$_2$CH$_2$SO$_3$Na |
| —H (cyclohexyl) | thiadiazolyl-S—SCH$_2$COOC$_2$H$_5$ |
| —H (cyclohexyl) | thiadiazolyl-S—SCH$_2$CH$_2$SO$_2$CH$_3$ |
| —H (cyclohexyl) | thiadiazolyl-S—CH$_2$OH |
| —H (cyclohexyl) | thiadiazolyl-S—NHCH$_3$ |
| —H (cyclohexyl) | thiazolyl-S— with CH$_3$, N-CH$_3$ |
| —H (cyclohexyl) | thiazolyl-S— with CH$_3$ |
| —H (cyclohexyl) | thiazolyl-S— with CH$_3$ |
| —H (cyclohexyl) | thiazolyl-S— with CH$_3$, CH$_3$ |

-continued
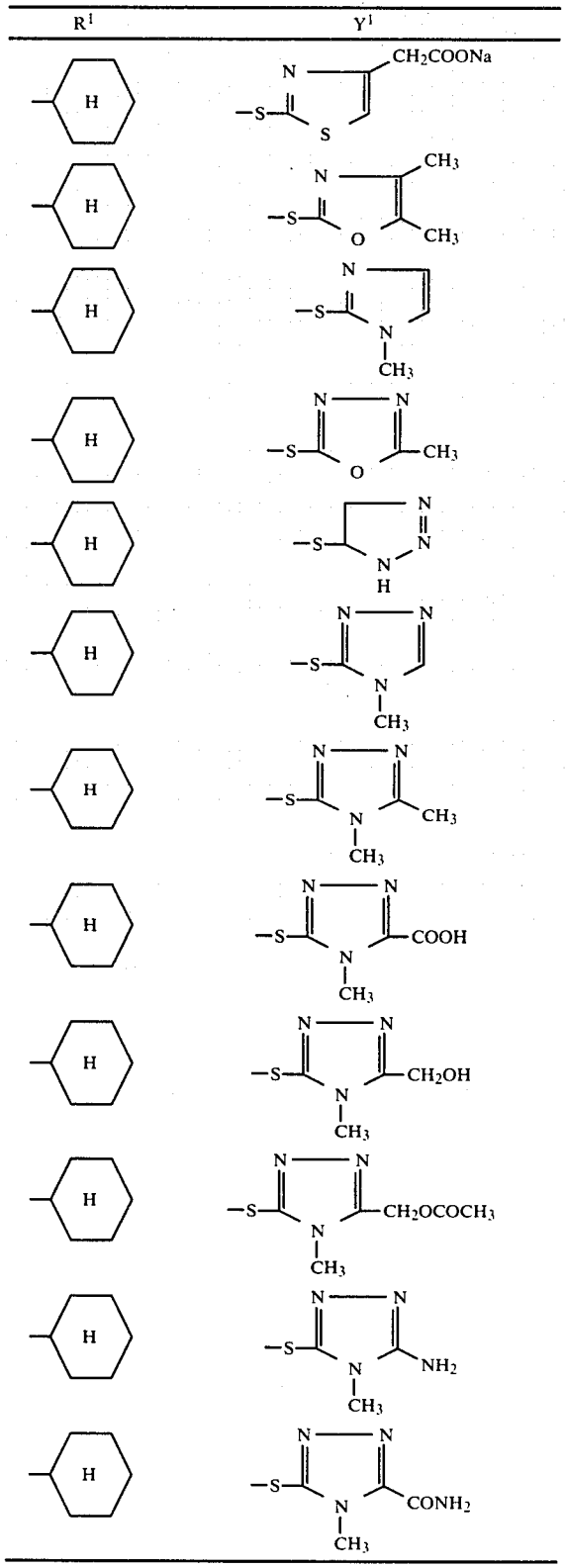
As examples of the compounds according to this invention, there may be mentioned the following compounds of the formula:
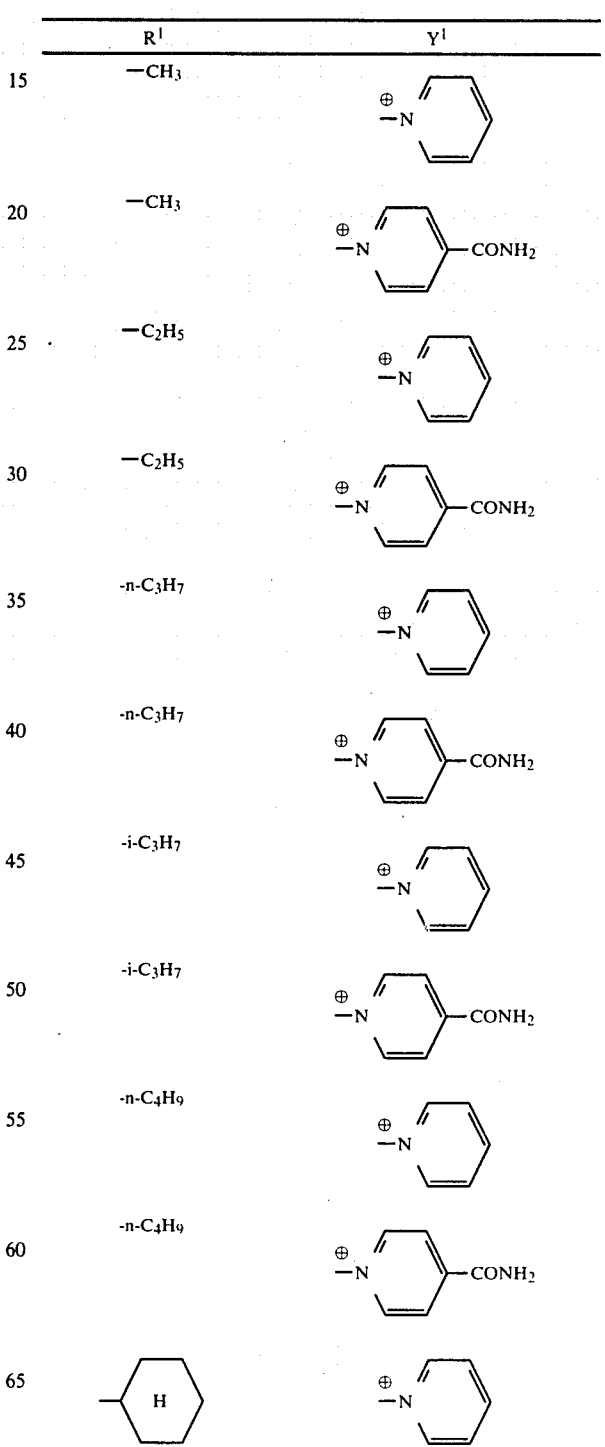
and pharmacologically acceptable salts thereof.

-continued

| R¹ | Y¹ |
|---|---|
| 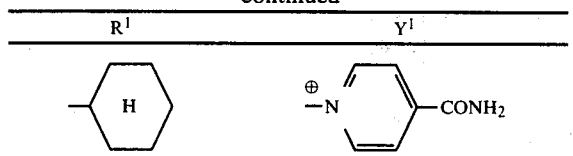 | |

The following examples are further descriptive of the method of this invention. In the examples, NMR spectra were measured with a Varian spectrometer XL-100 (100 MHz), A-60A (60 MHz) or T-60 (60 MHz), with tetramethylsilane as the reference, and the δ values are expressed in ppm.

The minimal inhibitory concentrations (M.I.C.) of some representative cephalosporin derivatives of this invention as produced by the procedures described in those examples and the minimal inhibitory concentrations of cephalothin [sodium 7-(2-thienylacetamido)-3-acetoxymethyl-3-cephem-4-carboxylate], cephaloridine [7-(2-thienylacetamido)-3-(1-pyridyl)methyl-3-cephem-4-carboxylic acid betaine] and cefazolin [sodium 7-(1H-tetrazol-1-yl)acetamido-3-(2-methyl-1,3,4-thiadiazol-5-yl)thiomethyl-3-cephem-4-carboxylate], which are among the clinically established and commercially available cephalosporins (as described, for example, in the New England Journal of Medicine 294, 24, 1976 and Journal of Pharmaceutical Science 64, 1899, 1975), both against various bacteria, as well as the therapeutic effects of some respresentative cephalosporin derivatives of this invention and of cephaloridine in infected mice, are shown in tables.

(a) Determination of minimal inhibitory concentrations (Tables 1 to 8):
Procedure: agar dilution method
Medium: TSA
Inoculum size: $10^7$/ml Table 1

| | Gram-positive bacteria | | Gram-negative bacteria | | | | | | |
|---|---|---|---|---|---|---|---|---|---|
| Test compound | S. aureus 209P | S. aureus 1840 | E. coli NIHJ JC-2 | E. coli 0-111 | E. coli T-7 | K. pneumoniae DT | K. pneumoniae GN 3835 | S. marcescens IFO 12648 | S. marcescens TN 24 |
| Cephalothin | 0.20 | 0.39 | 12.5 | 3.13 | 100 | 1.56 | 12.5 | >100 | >100 |
| Cephaloridine | 0.05 | 0.39 | 3.13 | 1.56 | >100 | 1.56 | 12.5 | >100 | >100 |
| Cefazolin | 0.39 | 1.56 | 1.56 | 1.56 | 50 | 1.56 | 6.25 | >100 | >100 |
| Example II - 1 | 1.56 | 3.13 | 0.1 | ≦0.012 | 0.39 | 0.05 | 0.1 | 3.13 | 6.25 |
| Example II - 7 | 1.56 | 3.13 | 0.39 | 0.024 | 1.56 | 0.05 | 0.39 | 6.25 | 6.25 |
| Example II - 12 | 1.56 | 1.56 | 0.39 | 0.024 | 3.13 | 0.1 | 0.39 | 6.25 | 12.5 |
| Example II - 16 | 1.56 | 3.13 | 0.39 | 0.024 | 3.13 | 0.1 | 0.78 | 6.25 | 25 |
| Example II - 20 | 1.56 | 1.56 | 0.1 | 0.024 | 3.13 | 0.05 | 0.39 | 6.25 | 12.5 |
| Example II - 24 | 0.78 | 1.56 | 0.1 | 0.024 | 1.56 | 0.05 | 0.39 | 6.25 | 12.5 |

Table 2

| | Gram-positive bacteria | | Gram-negative bacteria | | | | | | |
|---|---|---|---|---|---|---|---|---|---|
| Test compound | S. aureus 209P | S. aureus 1840 | E. coli NIHJ JC-2 | E. coli 0-111 | E. coli T-7 | K. pneumoniae DT | K. pneumoniae GN 3835 | S. marcescens IFO 12648 | S. marcescens TN 24 |
| Example II - 3 | 3.13 | 3.13 | 0.1 | 0.024 | 0.39 | 0.024 | 0.1 | 3.13 | 6.25 |
| Example II - 8 | 3.13 | 3.13 | 0.2 | 0.024 | 1.56 | 0.05 | 0.2 | 6.25 | 6.25 |
| Example II - 13 | 1.56 | 3.13 | 0.2 | 0.05 | 1.56 | 0.05 | 0.2 | 6.25 | 25 |
| Example II - 17 | 1.56 | 3.13 | 0.39 | 0.05 | 3.13 | 0.1 | 0.39 | 6.25 | 25 |
| Example II - 21 | 1.56 | 3.13 | 0.39 | 0.05 | 3.13 | 0.1 | 0.39 | 6.25 | 25 |
| Example II - 4 | 1.56 | 1.56 | 0.2 | 0.024 | 1.56 | 0.05 | 0.39 | 1.56 | 0.78 |
| Example II - 9 | 1.56 | 3.13 | 0.39 | 0.05 | 3.13 | 0.1 | 0.78 | 3.13 | 3.13 |
| Example II - 14 | 1.56 | 3.13 | 0.39 | 0.024 | 3.13 | 0.1 | 0.39 | 3.13 | 3.13 |
| Example II - 18 | 1.56 | 3.13 | 0.2 | 0.024 | 3.13 | 0.1 | 1.56 | 3.13 | 3.13 |

Table 3

| | Gram-positive bacteria | | Gram-negative bacteria | | | | | | |
|---|---|---|---|---|---|---|---|---|---|
| Test Compound | S. aureus 209P | S. aureus 1840 | E. coli NIHJ JC-2 | E. coli 0-111 | E. coli T-7 | K. pneumoniae DT | K. pneumoniae GN 3835 | S. marcescens IFO 12648 | S. marcescens TN 24 |
| Example II - 22 | 0.78 | 3.13 | 0.39 | 0.024 | 6.25 | 0.1 | 0.78 | 6.25 | 5.13 |
| Example II - 5 | 3.13 | 3.13 | 0.39 | 0.1 | 3.13 | 0.1 | 0.78 | 3.13 | 0.78 |
| Example II - 10 | 0.78 | 1.56 | 0.78 | 0.2 | 3.13 | 0.2 | 0.78 | 3.13 | 1.56 |
| Example IV - 2 | 3.13 | 3.13 | 0.78 | 0.2 | 6.25 | 0.39 | 1.56 | 3.13 | 3.13 |
| Example II - 6 | 50 | 50 | 3.13 | 0.78 | 6.25 | 0.78 | 1.56 | 50 | 100 |
| Example II - 11 | 25 | 25 | 6.25 | 1.56 | 12.5 | 1.56 | 3.13 | 100 | 100 |
| Example II - 15 | 12.5 | 12.5 | 6.25 | 3.13 | 25 | 3.13 | 6.25 | >100 | >100 |
| Example II - 19 | 25 | 25 | 6.25 | 3.13 | 25 | 3.13 | 6.25 | 100 | >100 |
| Example II - 23 | 12.5 | 12.5 | 12.5 | 6.25 | 25 | 3.13 | 6.25 | 100 | >100 |

Table 4

| | Gram-positive bacteria | | Gram-negative bacteria | | | | | | |
|---|---|---|---|---|---|---|---|---|---|
| Test compound | S. aureus 209P | S. aureus 1840 | E. coli NIHJ JC-2 | E. coli 0-111 | E. coli T-7 | K. pneumoniae DT | K. pneumoniae GN 3835 | S. marcescens IFO 12648 | S. marcescens TN 24 |
| Example IV - 3 | 1.56 | 3.13 | 0.39 | ≦0.2 | 3.13 | ≦0.2 | 0.39 | 6.25 | 6.25 |
| Example IV - 4 | 3.13 | 3.13 | ≦0.2 | ≦0.2 | 3.13 | ≦0.2 | 0.39 | 3.13 | 3.13 |
| Example IV - 5 | 6.25 | 6.25 | ≦0.2 | ≦0.2 | 1.56 | ≦0.2 | 0.39 | 3.13 | 3.13 |
| Example IV - 6 | 1.56 | 3.13 | ≦0.2 | ≦0.2 | 3.13 | ≦0.2 | 0.39 | 3.13 | 3.15 |
| Example IV - 7 | 12.5 | 12.5 | 0.78 | ≦0.2 | 6.25 | ≦0.2 | 0.39 | 3.13 | 6.25 |
| Example IV - 8 | 0.78 | 1.56 | 1.56 | 0.39 | 6.25 | 0.39 | 3.13 | 6.25 | 6.25 |
| Example IV - 9 | 3.13 | 3.13 | 0.78 | ≦0.2 | 3.13 | ≦0.2 | 0.78 | 6.25 | 6.25 |
| Example IV - 10 | 1.56 | 3.13 | 0.39 | ≦0.2 | 6.25 | ≦0.2 | 0.78 | 6.25 | 6.25 |

Table 5

| | Gram-negative bacteria | | | | | | | | |
|---|---|---|---|---|---|---|---|---|---|
| Test compound | P. vulgaris IFO 3988 | P. vulgaris GN 4413 | P. mirabilis GN 4359 | P. morganii IFO 3168 | P. rettgeri TN 338 | P. rettgeri GN4733 | E. cloacae TN 1282 | C. freundii GN 99 | C. freundii GN 1706 |
| Cephalothin | 1.56 | >100 | 3.13 | >100 | 1.56 | >100 | >100 | 25 | >100 |
| Cephaloridine | 6.25 | >100 | 6.25 | >100 | 1.56 | >100 | >100 | 50 | >100 |
| Cefazolin | 3.13 | >100 | 6.25 | 100 | ≦0.2 | 100 | >100 | 12.5 | >100 |
| Example II - 1 | 0.05 | 12.5 | 0.1 | 0.39 | ≦0.012 | 0.05 | 1.56 | 0.1 | 0.39 |
| Example II - 7 | 0.2 | 6.25 | 0.1 | 1.56 | ≦0.012 | 0.1 | 12.5 | 0.39 | 0.78 |
| Example II - 12 | 0.39 | 12.5 | 0.1 | 0.78 | ≦0.012 | 0.2 | 6.25 | 0.39 | 0.78 |
| Example II - 16 | 0.39 | 25 | 0.1 | 0.78 | ≦0.012 | 0.2 | 6.25 | 0.39 | 0.78 |
| Example II - 20 | 0.2 | 12.5 | 0.1 | 0.39 | ≦0.012 | 0.05 | 6.25 | 0.39 | 0.39 |
| Example II - 24 | 0.1 | 25 | 0.1 | 0.39 | ≦0.012 | 0.05 | 3.13 | 0.39 | 0.78 |

Table 6

| | Gram-negative bacteria | | | | | | | | |
|---|---|---|---|---|---|---|---|---|---|
| Test compound | P. vulgaris IFO 3988 | P. vulgaris GN 4413 | P. mirabilis GN 4359 | P. morganii IFO 3168 | P. rettgeri TN 338 | P. rettgeri GN4733 | E. cloacae TN 1282 | C. freundii GN 99 | C. freundii GN 1706 |
| Example II - 3 | 0.05 | 50 | 0.05 | 0.78 | ≦0.012 | 0.1 | 6.25 | 0.1 | 0.2 |
| Example II - 8 | 0.1 | 100 | 0.1 | 3.13 | ≦0.012 | 0.05 | 12.5 | 0.1 | 0.39 |
| Example II - 13 | 0.39 | 50 | 0.1 | 3.13 | ≦0.012 | 0.1 | 6.25 | 0.1 | 0.78 |
| Example II - 17 | 0.39 | 100 | 0.1 | 1.56 | ≦0.012 | 0.1 | 6.25 | 0.39 | 0.78 |
| Example II - 21 | 0.39 | 50 | 0.2 | 1.56 | ≦0.012 | 0.39 | 25 | 0.39 | 0.78 |
| Example II - 4 | 0.1 | 12.5 | 0.1 | 0.1 | ≦0.012 | 0.1 | 1.56 | 0.1 | 0.39 |
| Example II - 9 | 0.2 | 25 | 0.39 | 1.56 | ≦0.012 | 0.2 | 6.25 | 0.2 | 0.78 |
| Example II - 14 | 0.1 | 12.5 | 0.39 | 0.2 | ≦0.012 | 0.2 | 3.13 | 0.2 | 0.39 |
| Example II - 18 | 0.1 | 25 | 0.39 | 0.78 | ≦0.012 | 0.2 | 3.13 | 0.39 | 0.78 |

Table 7

| | Gram-negative bacteria | | | | | | | | |
|---|---|---|---|---|---|---|---|---|---|
| Test compound | P. vulgaris IFO 3988 | P. vulgaris GN 4413 | P. mirabilis GN 4359 | P. morganii IFO 3168 | P. rettgeri TN 338 | P. rettgeri GN4733 | E. cloacae TN 1282 | C. freundii GN 99 | C. freundii GN 1706 |
| Example II - 22 | 0.1 | 12.5 | 0.39 | 0.78 | ≦0.012 | 0.1 | 12.5 | 0.2 | 0.78 |
| Example II - 5 | 0.39 | 12.5 | 0.78 | 0.39 | ≦0.05 | 0.78 | 1.56 | 0.39 | 1.56 |
| Example II - 10 | 0.39 | 12.5 | 0.78 | 0.39 | ≦0.05 | 0.78 | 3.13 | 0.39 | 0.78 |
| Example IV - 2 | 0.78 | 12.5 | 1.56 | 0.78 | 0.1 | 0.78 | 3.13 | 0.78 | 1.56 |
| Example II - 6 | 1.56 | 12.5 | 0.78 | 12.5 | 0.024 | 0.2 | 50 | 6.25 | 12.5 |
| Example II - 11 | 3.13 | 50 | 1.56 | 25 | 0.05 | 0.39 | 25 | 6.25 | 12.5 |
| Example II - 15 | 12.5 | 50 | 3.13 | 50 | 0.1 | 0.39 | >100 | 12.5 | 12.5 |
| Example II - 19 | 12.5 | 50 | 3.13 | 50 | 0.1 | 0.39 | 100 | 12.5 | 12.5 |
| Example II - 23 | 12.5 | 50 | 3.13 | 100 | 0.1 | 0.39 | 100 | 12.5 | 25 |

Table 8

| Test compound | Gram-negative bacteria | | | | | | | | |
|---|---|---|---|---|---|---|---|---|---|
| | P. vulgaris IFO 3988 | P. vulgaris GN 4413 | P. mirabilis GN 4359 | P. morganii IFO 3168 | rettgeri TN 338 | P. rettgeri GN4733 | E. Cloacae TN 1282 | C. freundii GN 99 | C. freundii GN 1706 |
| Example IV - 3 | 0.39 | 100 | 0.39 | 0.39 | ≦0.2 | 0.39 | 1.56 | ≦0.2 | 0.78 |
| Example IV - 4 | ≦0.2 | 12.5 | ≦0.2 | ≦0.2 | ≦0.2 | 0.39 | 3.13 | ≦0.2 | 0.39 |
| Example IV - 5 | 0.39 | 25 | 0.39 | 0.39 | ≦0.2 | 0.78 | 3.13 | 0.39 | 0.78 |
| Example IV - 6 | ≦0.2 | 25 | 0.39 | ≦0.2 | ≦0.2 | 0.39 | 3.13 | ≦0.2 | ≦0.78 |
| Example IV - 7 | ≦0.2 | 50 | ≦0.2 | 0.78 | ≦0.2 | 0.39 | 12.5 | 0.78 | 3.13 |
| Example IV - 8 | 0.39 | 6.25 | 0.78 | 3.13 | ≦0.2 | 0.78 | 6.25 | 0.78 | 3.13 |
| Example IV - 9 | 0.39 | 25 | 0.39 | 0.78 | ≦0.2 | 1.56 | 6.25 | 0.78 | 1.56 |
| Example IV - 10 | 0.39 | 25 | 0.39 | 0.39 | ≦0.2 | 0.78 | 3.13 | 0.39 | 0.78 |

PREPARATION EXAMPLE 1—FOR ORAL ADMINISTRATION

The active compound and lactose were previously admixed according to the following formula and the mixture was kneaded with an aqueous solution of hydroxypropyl-cellulose. The mixture was dried and pulverized to size. This powder was then admixed with magnesium stearate previously diluted with starch and the composition was tableted.

Pivaloyloxymethyl 7-[2-(2-amino-4-thiazolin-4-yl)-2-methylcarbamoyloximinoacetamido]-3-(2-methyl-1,3,4-thiadiazol-5-yl)thiomethyl-3-cephem-4-carboxylate (syn-isomer)

| (Example III - 1) | 65 mg. |
|---|---|
| Lactose | 27 mg |
| Starch | 5 mg |
| Hydroxypropyl-cellulose L | 2.7 mg |
| Pure water | 0.03 mg |
| Magnesium stearate | 0.3 mg |
| | 100 mg/tablet |

PREPARATION EXAMPLE 2—FOR ORAL ADMINISTRATION

According to the formula given below, a portion of starch was mixed with magnesium stearate. The active compound and the balance of starch were then added. The mixture was filled into capsules in the conventional manner.

Pivaloyloxymethyl 7-[2-(2-imino-4-thiazolin-4-yl)-2-methylcarbamoyloximinoacetamido]-3-(1-methyl-1H-tetrazol-5-yl)-thiomethyl-3-cephem-4-carboxylate (syn-isomer)

| (Example III-2) | 68 mg |
|---|---|
| Starch | 30 mg |
| Magnesium stearate | 2 mg |
| | 100 mg/capsule |

PREPARATION EXAMPLE 3—FOR ORAL ADMINISTRATION

According to the formula given below, the active compound, starch and lactose were previously admixed and an aqueous solution of hydroxypropyl-cellulose was then added. The mixture was kneaded, dried and pulverized. The resultant powders were sieved through a screen of 32 to 150 mesh, whereby a fine granular product was obtained.

Pivaloyloxymethyl 7-[2-(2-imino-4-thiazolin-4-yl)-2-ethylcarbamoyloximinoacetamido]-3-(1-methyl-1H-tetrazol-5-yl)thiomethyl-3-cephem-4-carboxylate (syn-isomer)

| (Example III-3) | 65 mg |
|---|---|
| Lactose | 22 mg |
| Pure water | 0.03 mg |
| Starch | 10 mg |
| Hydroxypropyl-cellulose | 3 mg |
| | 100 mg/tablet |

PREPARATION EXAMPLE 1—FOR PARENTERAL INJECTION

In 100 ml of sterilized physiological saline was dissolved 1 mg of sodium 7-[2-(2-imino-4-thiazolin-4-yl)-2-methylcarbamoyloximinoacetamido]-3-carbamoyloxymethyl-3-cephem-4-carboxylate (syn-isomer) (Example II-3), whereby an injectable solution was obtained.

PREPARATION EXAMPLE 2—FOR PARENTERAL INJECTION

In 100 ml of sterilized physiological saline was dissolved 1 mg of sodium 7-[2-(2-imino-4-thiazolin-4-yl)-2-methylcarbamoyloximinoacetamido]-3-(1-methyl-1H-tetrazol-5-yl)thiomethyl-3-cephem-4-carboxylate (syn-isomer) (Example II-4), whereby an injectable solution was obtained.

PREPARATION EXAMPLE 3—FOR PARENTERAL INJECTION

In 100 ml of sterilized physiological saline was dissolved 1 mg of sodium 7-[2-(2-imino-4-thiazolin-4-yl)-2-butylcarbamoyloximinoacetamido]-3-carbamoyloxymethyl-3-cephem-4-carboxylate (syn-isomer)(Example II-21), whereby an injectable solution was obtained.

ADMINISTRATION EXAMPLE (Subcutaneous injection)

The preliminary therapeutic effects of some cephalosporin derivatives of this invention as determined in infected mice were as follows.

Determination of therapeutic effects in infected mice
Test animals: Male mice ICR/SLC
Each compound was administered to a group of 5 animals.
Route of infection: Intraperitoneally infected with *Escherichia coli* O-111
Period of observation: 7 days.
Method of administration:
  One mg of each test compound was dissolved in 100 ml of sterile physiological saline and a dilution series of the same solution was prepared. These solutions were respectively injected subcutaneously into mice immediately after infection, in a single dose of 0.2 ml each.

| Test compound | Route of administration | $ED_{50}$, mg/kg |
|---|---|---|
| Example II-3 | S.C. | 0.016 |
| Example II-4 | S.C. | 0.025 |
| Example II-21 | S.C. | 0.10 |
| Cephaloridine | S.C. | 2.00 |

EXAMPLE I-1

Production of 7-(4-chloro-2-methylcarbamoyloximino-3-oxobutyrylamino)-3-acetoxymethyl-3-cephem-4-carboxylic acid (syn-isomer).

In 5 ml of acetonitrile was suspended 0.840 g (2 m moles) of 7-(4-chloro-2-hydroximino-3-oxobutrylamino)-3-acetoxymethyl-3-cephem-4-carboxylic acid (syn-isomer) and, under ice-cooling, 2 ml of methyl isocyanate was added. The ice bath was removed after 10 minutes and the mixture was stirred at room temperature for 2 hours. Upon concentration to dryness, the above-indicated compound was obtained, Yield 1.04 g.

IR(KBr, cm$^{-1}$): 1780.

NMR(100 MHz, d$_6$-DMSO, δ): 2.03(s, OAc), 2.74(d, J=5 Hz, NCH$_3$), 3.43 & 3.68(ABq, J=18 Hz, 2-H), 4.70 & 5.03(ABq, J=13 Hz, 3-CH$_2$), 5.04(s, ClCH$_2$), 5.16(d, J=5 Hz, 6-H), 5.81(dd, J=5 & 8 Hz, 7-H), 7.77(q, J=5 Hz, CO<u>NH</u>-CH$_3$), 9.56(d, J=8 Hz, CONH).

Elemental Analysis: Calcd. for C$_{16}$H$_{17}$N$_4$O$_9$SCl.0.5-H$_2$O: C, 39.55; H, 3.73; N, 11.53; Found: C, 39.81; H, 4.07; N, 11.29.

EXAMPLE I-2

Production of 7-(4-chloro-2-cyclohexylcarbamoyloximino-3-oxobutrylamino)-3-acetoxymethyl-3-cephem-4-carboxylic acid (syn-isomer).

In 8 ml of acetonitrile, 0.840 g (2 m moles) of 7-(4-chloro-2-hydroximino-3-oxobutyrylamino)-3-acetoxymethyl-3-cephem-4-carboxylic acid (syn-isomer) and 2 ml of cyclohexyl isocyanate were stirred at room temperature for 22 hours, after which time the reaction mixture was treated in the same manner as in above Example I-1. By the above procedure was obtained 1.20 g of the above-indicated compound.

IR(KBr, cm$^{-1}$): 1780.

NMR(100 MHz, d$_6$-DMSO, δ):
1.0 to 2.1(m, cyclohexyl-CH$_2$), 2.05(s, OAc), 3.41 & 3.65 (ABq, J=18 Hz, 2-H), 4.72 & 5.03(ABq, J=13 Hz, 3—CH$_2$), 5.00 (s, ClCH$_2$), 5.14(d, J=5 Hz, 6-H), 5.78(dd, J=5 & 8 Hz, 7-H), 7.64(d, J=8 Hz, CO<u>NH</u>-cyclohexyl), 9.52(d, J=8 Hz, CONH).

EXAMPLE I-3 TO EXAMPLE I-24

In the same manner as Example I-1 and Example I-2, compounds having the formula:

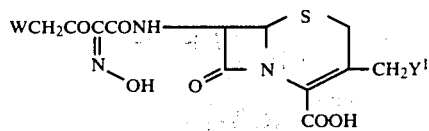

were respectively reacted with an isocyanate compound of the formula R$^1$NCO and the reaction products were similarly treated to obtain the corresponding compounds of the formula:

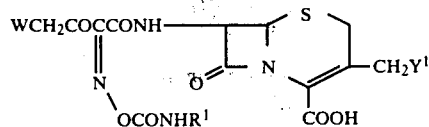

The physical data on the resultant compounds are shown below. [Notes] In the following table:

"Ex. No." denotes "examples number"; "DMSO" denotes "dimethylsulfoxide"; "δ" denotes "δ value"; "Me" denotes "CH$_3$"; "Et" denotes "CH$_2$CH$_3$";

"Pr" denotes "CH$_2$CH$_2$CH$_3$"; "iso-Pr" denotes "CH$\diagdown{\text{CH}_3 \atop \text{CH}_3}$";

"Bu" denotes "CH$_2$CH$_2$CH$_2$CH$_3$".
(The same definitions apply hereinafter)

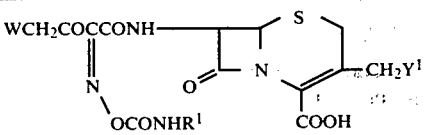

| Ex. No. | W | R$^1$ | Y$^1$ | Physical Data |
|---|---|---|---|---|
| I-3 | Br | CH$_3$— | —OAc | IR(KBr,cm$^{-1}$):1790<br>NMR(100MHz,d$_6$-DMSO,δ):<br>2.03(s,OAc),2.74(d,J=5Hz,<br>NCH$_3$),3.48 & 3.70(ABq,J=<br>18Hz,2-H),4.70 & 5.04(ABq,<br>J=13Hz,3-CH$_2$),4.88(s,Br<br>CH$_2$),5.18(d,J=5Hz,6-H),<br>5.84(dd,J=5 & 8Hz,7-H),<br>7.77(q,J=5Hz,CONHMe),9.57<br>(d,J=8Hz,CONH) |
| I-4 | Cl | —CH$_3$ | —H | IR(KBr,cm$^{-1}$):1780<br>NMR(100MHz,d$_6$-DMSO,δ):<br>2.04(s,3-CH$_3$),2.74(d,J=5<br>Hz,NCH$_3$),3.33 & 3.63(ABq,<br>J=18Hz,2-H),5.04(s,ClCH$_2$),<br>5.11(d,J=5Hz,6-H),5.74(dd,<br>J=5 & 8Hz,7-H),7.76(q,J=<br>5Hz,CONHMe),9.52(d,J=8Hz, |

-continued

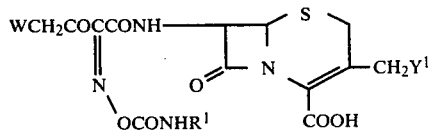

| Ex. No. | W | R¹ | Y¹ | Physical Data |
|---|---|---|---|---|
| I-5 | Cl | —CH₃ | —OCONH₂ | IR(KBr,cm⁻¹): 1770 NMR(100MHz,d₆-DMSO,δ): 2.74(d,J=5Hz,NCH₃),3.40 & 3.63(ABq,J=18Hz,2-H),4.63 & 4.92(ABq,J=13Hz,3-CH₂), 5.03(s,ClCH₂),5.15(d,J=5 Hz,6-H),5.79(dd,J=5 & 8Hz, 7-H),6.51(b-s,OCONH₂), 7.74(q,J=5Hz,CONHMe),9.53 (d,J=8Hz,CONH). |
| I-6 | Cl | —CH₃ | (tetrazole-S-CH₃) | IR(KBr,cm⁻¹): 1780 NMR(100MHz,d₆-DMSO,δ): 2.74(d,J=5Hz,NCH₃),3.61 & 3.83(ABq,J=18Hz,2-H),3.96 (s,tetrazole-CH₃),4.23 & 4.40(ABq,J=13Hz,3-CH₂), 5.04(s,ClCH₂),5.16(d,J= 5Hz,6-H),5.81(dd,J=5 & 8Hz,7-H),7.76(q,,J=5Hz, CONHMe),9.58(d,J=8Hz,CONH). |
| I-7 | Cl | —CH₃ | (thiadiazole-S-CH₃) | IR(KBr,cm⁻¹): 1770 NMR(100MHz,d₆-DMSO,δ) 2.70(s,thiadiazole-CH₃),2.74 (d,J=5Hz,NCH₃),3.56 & 3.81 (ABq,J=18Hz,2-H),4.21 & 4.52(ABq,J=13Hz,3-CH₂), 5.02(s,ClCH₂),5.16(d,J=5Hz, 6-H),5.81(dd,J=5 & 8Hz, 7-H),7.75(q,J=5Hz,CONHMe), 9.57(d,J=8Hz,CONH) |
| I-8 | Cl | —CH₂CH₃ | —OAc | IR(KBr,cm⁻¹): 1780 NMR(100MHz,d₆-DMSO,δ): 1.12(t,J=7Hz,Et-CH₃),2.05 (s,OAc),3.17(dt,J=6 & 7Hz, Et-CH₂),3.43 & 3.68(ABq, J=18Hz,2-H),4.71 & 5.04 (ABq,J=13Hz,3-CH₂),5.04 (s,ClCH₂),5.17(d,J=5Hz,6-H), 5.81(dd,J=5 & 8Hz,7-H), 7.87(t,J=6Hz,CONHEt),9.55 (d,J=8Hz,CONH) |
| I-9 | Cl | —CH₂CH₃ | —H | IR(KBr,cm⁻¹): 1760 NMR(100MHz,d₆-DMSO,δ): 1.12(t,J=7Hz,Et-CH₃),2.04 (s,3-CH₃),3.17(dq,J=6 & 7 Hz,Et-CH₂),3.33 & 3.63 (ABq,J=18Hz,2-H),5.04(s, ClCH₂),5.12(d,J=5Hz,6-H), 5.74(dd,J=5 & 8Hz,7-H), 7.87(t,J=6Hz,CONHEt),9.52 (d,J=8Hz,CONH). |
| I-10 | Cl | —CH₂CH₃ | —OCONH₂ | IR(KBr,cm⁻¹): 1770 NMR(100MHz,d₆-DMSO,δ): 1.11(t,J=7Hz,Et-CH₃),3.18 (dq,J=6 & 7Hz,Et-CH₂),3.43 & 3.65(ABq,J=18Hz,2-H), 4.62 & 4.94(ABq,J=13Hz,3-CH₂),5.04(s,ClCH₂),5.17(d, J=5Hz,6-H),5.91(dd,J=5 & 8Hz,),6.54(b-s,OCONH₂),7.89 (t,J=6Hz,CONHEt),9.56(d, J=8Hz,CONH). |

-continued

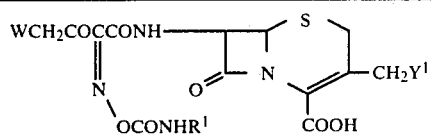

| Ex. No. | W | $R^1$ | $Y^1$ | Physical Data |
|---|---|---|---|---|
| I-11 | Cl | —CH$_2$CH$_3$ | ![tetrazole-SCH$_3$ with N-CH$_3$] | IR(KBr,cm$^{-1}$): 1780 NMR(100MHz,d$_6$-DMSO,δ): 1.12(t,J=7Hz,Et-CH$_3$),3.16 (dq,J=6 & 7Hz,Et-CH$_2$), 3.60 & 3.82(ABq,J=18Hz, 2-H),3.96(s,tetrazole-CH$_3$), 4.22 & 4.40(ABq,J=13Hz,3-CH$_2$),5.04(s,ClCH$_2$),5.15 (d,J=5Hz,6-H),5.80(dd,J=5 & 8Hz,7-H),7.88(t,J=6Hz, CONHEt),9.58(d,J=8Hz,CONH). |
| I-12 | Cl | —CH$_2$CH$_3$ | ![thiadiazole-S-CH$_3$] | IR(KBr,cm$^{-1}$): 1770 NMR(100MHz,d$_6$-DMSO,δ): 1.11(t,J=7Hz,Et-CH$_3$), 2.70(s,thiadiazole-CH$_3$), 3.17(dq,J=6 & 7Hz,Et-CH$_2$), 3.66 & 3.82(ABq,J=18Hz, 2-H),4.23 & 4.54(ABq,J=13 Hz,3-CH$_2$),5.03(s,ClCH$_2$), 5.17(d,J=5Hz,6-H),5.82(dd, J=5 & 8Hz,7-H),7.88(t,J= 6Hz,CONHEt),9.57(d,J=8Hz, CONH). |
| I-13 | Cl | —CH$_2$CH$_2$CH$_3$ | —OAc | IR(KBr,cm$^{-1}$): 1770 NMR(100MHz,d$_6$-DMSO,δ): 0.88(t,J=7Hz,Pr—CH$_3$),1.2-1.8(m,CH$_3$CH$_2$CH$_2$),2.05(s, OAc),3.10(dq,J=6 & 6Hz, NCH$_2$C$_2$H$_5$),3.43 & 3.69(ABq, J=18Hz,2-H),4.71 & 5.04 (ABq,J=13Hz,3-CH$_2$),5.03 (s,ClCH$_2$),5.17(d,J=5Hz, 6-H),5.82(dd,J=5 & 8Hz, 7-H),7.87(t,J=6Hz,CONHPr), 9.56(d,J=8Hz,CONH). |
| I-14 | Cl | —CH$_2$CH$_2$CH$_3$ | —H | IR(KBr,cm$^{-1}$): 1760 NMR(100MHz,d$_6$-DMSO,δ): 0.88(t,J=7Hz,Pr—CH$_3$),1.1-1.8(m,CH$_3$CH$_2$CH$_2$),2.04(s, 3-CH$_3$),3.10(dt,J=6 & 6Hz, NCH$_2$C$_2$H$_5$),3.33 & 3.63(ABq, J=18Hz,2-H),5.03(s,ClCH$_2$), 5.12(d,J=5Hz,6-H),5.74(dd, J=5 & 8Hz,7-H),7.86(t,J= 6Hz,CONHPr),9.52(d,J=8Hz, CONH). |
| I-15 | Cl | —CH$_2$CH$_2$CH$_3$ | —OCONH$_2$ | IR(KBr,cm$^{-1}$): 1770 NMR(100MHz,d$_6$-DMSO,δ): 0.88(t,J=7Hz,Pr—CH$_3$),1.1-1.8(m,CH$_3$CH$_2$CH$_2$),3.08(dt, J=6 & 6Hz,NCH$_2$C$_2$H$_5$),3.42 & 3.65(ABq,J=18Hz,2-H), 4.63 & 4.93(ABq,J=13Hz, 3-CH$_2$),5.03(s,ClCH$_2$),5.17 (d,J=5Hz,6-H),5.81(dd,J=5 & 8Hz,7-H),6.54(b-s,OCONH$_2$), 7.86(t,J=6Hz,CONHPr),9.56 (d,J=8Hz,CONH). |
| I-16 | Cl | —CH$_2$CH$_2$CH$_3$ | ![tetrazole-S with N-CH$_3$] | IR(KBr,cm$^{-1}$): 1780 NMR(100MHz,d$_6$-DMSO,δ): 0.88(t,J=7Hz,Pr—CH$_3$),1.1 to 1.8(m,CH$_3$CH$_2$CH$_2$),3.08 (dt,J=6 & 6Hz,NCH$_2$C$_2$H$_5$), 3.61 & 3.84(ABq,J=18Hz,2-H), 3.96(s,tetrazole-CH$_3$),4.23 & 4.41(ABq,J=13Hz,3-CH$_2$), 5.04(s,ClCH$_2$),5.16(d,J= 5Hz,6-H),5.82(dd,J=5 & 8Hz,7-H),7.88(t,J=6Hz, CONHPr),9.58(d,J=8Hz,CONH). |
| I-17 | Cl | —CH(CH$_3$)$_2$ | —OAc | IR(KBr,cm$^{-1}$): 1770 NMR(100MHz,d$_6$-DMSO,δ): |

-continued

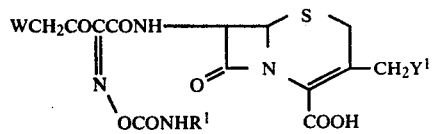

| Ex. No. | W | R¹ | Y¹ | Physical Data |
|---|---|---|---|---|
| I-18 | Cl | —CH(CH₃)₂ | —H | 1,18(d,J=6Hz,iso-Pr—CH₃), 2.05(s,OAc),3.42 & 3.68( ABq,J=18Hz,2-H),4.71 & 5.04(ABq,J=13Hz,3CH₂),5.01 (s,ClCH₂),5.16(d,J=5Hz,6-H),5.80(dd,J=5 & 8Hz,7-H), 7.66(d,J=8Hz,CONH-iso-Pr), 9.54(d,J=8Hz,CONH). IR(KBr,cm⁻¹): 1760 NMR(100MHz,d₆-DMSO,δ): 1.17(d,J=6Hz,iso-Pr—CH₃), 2.04(s,3-CH₃),3.33 & 3.63 (ABq,J=18Hz,2-H),5.00(s, ClCH₂),5.12(d,J=5Hz,6-H), 5.74(dd,J=5 & 8Hz,7-H), 7.66(d,J=8Hz,CONH-iso-Pr), 9.50(d,J=8Hz,CONH). |
| I-19 | Cl | —CH(CH₃)₂ | —OCONH₂ | IR(KBr,cm⁻¹): 1770 NMR(100MHz,d₆-DMSO,δ): 1.17(d,J=6Hz,iso-Pr—CH₃), 3.42 & 3.63(ABq,J=18Hz, 2H),4.64 & 4.94(ABq,J=13 Hz,3-CH₂),5.02(s,ClCH₂), 5.18(d,J=5Hz,6-H),5.80(dd, J=5 & 8Hz,7-H),6.54(b-s, OCONH₂),7.68(d,J=8Hz,CONH-iso-Pr),9.56(d,J=8Hz,CONH). |
| I-20 | Cl | —CH(CH₃)₂ | ![structure]-S-tetrazole-N-CH₃ | IR(KBr,cm⁻¹): 1780 NMR(100MHz,d₆-DMSO,δ): 1.16(d,J=6Hz,iso-Pr—CH₃), 3.68 & 3.81(ABq,J=18Hz, 2-H),3.96(s,tetrazole-CH₃), 4.23 & 4.40(ABq,J=13Hz,3-CH₂),5.01(s,ClCH₂),5.14 (d,J=5Hz,6-H),5.80(dd,J=6 & 8Hz,7-H),7.68(d,J=8Hz, CONH-iso-Pr), 9,56(d,J= 8Hz,CONH). |
| I-21 | Cl | —CH₂CH₂CH₂ . CH₃ | —OAc | IR(KBr,cm⁻¹): 1780 NMR(100MHz,d₆-DMSO,δ): 0.90(t,J=6Hz,Bu-CH₃),1.0 to 1.7(m,CH₃CH₂CH₂CH₂), 2.05(s,OAc),3.14(dt,J=6 & 6Hz,NCH₂C₃H₇),3.44 & 3.69( ABq,J=18Hz,2-H),4.71 & 5.04 (ABq,J=13Hz,3-CH₂),5.02 (s,ClCH₂),5.17(d,J=5Hz,6-H),5.82(dd,J=5 & 8Hz,7-H), 7.84(t,J=6Hz,CONHBu),9.54 (d,J=8Hz,CONH). |
| I-22 | Cl | —CH₂CH₂CH₂ . CH₃ | —H | IR(KBr,cm⁻¹): 1760 NMR(100MHz,d₆-DMSO,δ): 0.90(t,J=7Hz,Bu-CH₃),1.0 to 1.8(m,CH₃CH₂CH₂CH₂), 2.05(s,3-CH₃),3.13(dt,J=6 & 6Hz,NCH₂C₃H₇),3.22 & 3.63 (ABq,J=18Hz,2-H),5.03(s, ClCH₂),5.11(d,J=5Hz,6-H), 5.74(dd,J=5 & 8Hz,7-H), 7.84(t,J=6Hz,CONHBu),9.52 (d,J=8Hz,CONH). |
| I-23 | Cl | —CH₂CH₂CH₂ . CH₃ | —OCONH₂ | IR(KBr,cm⁻¹): 1770 NMR(100MHz,d₆-DMSO,δ): 0.90(t,J=6Hz,Bu-CH₃),1.0 to 1.8(m,CH₃CH₂CH₂CH₂), 3.13(dt,J=6 & 6Hz,NCH₂C₃H₇), 3.43 & 3.65(ABq,J=18Hz,2-H),4.63 & 4.92(ABq,J=13Hz, 3-CH₂),5.03(s,ClCH₂),5.17 (d,J=5Hz,6-H),5.81(dd,J=5 & 8Hz,7-H),6.54(b-s,OCONH₂), 7.86(t,J=6Hz,CONHBu),9.56(d, J=8Hz,CONH). |

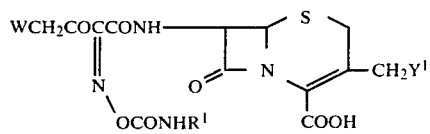

| Ex. No. | W | R¹ | Y¹ | Physical Data |
|---|---|---|---|---|
| 124 | Cl | —CH₂CH₂CH₂ . CH₃ | (tetrazole-SCH₃ group) | IR(KBr,cm⁻¹): 1780<br>NMR(100MHz,d₆-DMSO,δ):<br>0.90(t,J=6Hz,Bu-CH₃),1.0<br>to 1.8(m,CH₃CH₂CH₂CH₂),<br>3.12(dt,J=6 & 6Hz,NCH₂C₃H₇),<br>3.59 & 3.83(ABq,J=18Hz,2-H<br>),3.96(s,tetrazole-CH₃),<br>4.23 & 4.40(ABq,J=13Hz,3-<br>CH₂),5.03(s,ClCH₂),5.16<br>(d,J=5Hz,6-H),5.82(dd,J=<br>5 & 8Hz,7-H),7.86(t,J=6Hz,<br>CONHBu),9.58(d,J=8Hz,CONH). |

EXAMPLE I-25

Production of 7-(4-chloro-2-phenylcarbamoyloxyimino-3-oxobutrylamino)-3-acetoxymethyl-3-cephem-4-carboxylic acid (syn-isomer)

In 8 ml of acetonitrile was suspended 0.840 g (2 m moles) of 7-(4-chloro-2-hydroximino-3-oxobutrylamino)-3-acetoxymethyl-3-cephem-4-carboxylic acid (syn-isomer), followed by addition of 1.5 ml of phenyl isocyanate. The mixture was stirred at room temperature for 22 hours and, then, at 40° C. for 24 hours. The reaction mixture was concentrated under reduced pressure, the concentrate was treated with 30 ml of ether and the resultant powders were collected by filtration. By the above procedure there was obtained the above-indicated compound. Yield 0.904 g.

IR(KBr, cm⁻¹): 1780.

NMR(100 MHz, d₆-DMSO, δ);

2.05(s, OAc), 3.48 & 3.70 (ABq, J=18 Hz, 2-H), 4.70 & 5.04 (ABq, J=13 Hz, 3-CH₂), 5.02(s, ClCH₂), 5.20(d, J=5 Hz, 6-H), 5.90(dd, J=5 & 8 Hz, 7-H), 6.8 to 7.7 (m,phenyl), 10.20(b-s, CO-NH-phenyl), 9.62(d,J=8 Hz, CONH).

EXAMPLE II-1

Production of sodium 7-[2-(2-imino-4-thiazolin-4-yl)-2-methylcarbamoyloximinoacetamido]-3-acetoxymethyl-3-cephem-4-carboxylate (syn-isomer)

In 4 ml of dimethylacetamide, 0.941 g (1.97 m moles) of 7-(4-chloro-2-methylcarbamoyloximino-3-oxobutrylamino)-3-acetoxymethyl-3-cephem-4-carboxylic acid (syn-isomer) and 0.16 g (2.1 m moles) of thiourea were stirred at room temperature for 16 hours. The reaction mixture was then stirred with 10 ml of ether, the supernatant was removed by decanting, 10 ml of ether was added to the residue and the resultant precipitate was recovered by filtration. The precipitate was dissolved in 5 ml of water containing 0.36 g of sodium hydrogen carbonate and subjected to polystyrene column chromatography (Amberlite XAD-2, Rohm and Haas Co., trade name), elution being carried out with aqueous ethanol. The fractions containing the contemplated compound were pooled and lyophilized. By the above procedure there was obtained the above-indicated compound. Yield 0.573 g.

IR(KBr, cm⁻¹): 1750.

NMR(100 MHz, d₆-DMSO, δ): 2.03(s, OAc), 2.72(d, J=5 Hz, NCH₃), 3.24 & 3.53 (ABq, J=18 Hz, 2-H), 4.83 & 5.05(ABq, J=13 Hz, 3-CH₂), 5.06(d,J=5 Hz, 6-H), 5.64(dd, J=5 & 8 Hz, 7-H), 7.08(s, thiazoline 5-H), 7.19(q,J=5 Hz, CONHMe), 7.34

(b-s, NH=C—NH—), 9.74(d, J=8 Hz, CONH).

NMR(100 MHz, D₂O, δ): 2.13(s, OAc), 2.85(s, NCH₃), 3.40 & 3.72 (ABq, J=18 Hz, 2-H), 4.74 & 4.95(ABq, J=13 Hz, 3-CH₂), 5.24 (d, J=5 Hz, 6-H), 5.86(d, J=5 Hz, 7-H), 7.25(s, thiazoline 5-H).

Elemental analysis: C₁₇H₁₇N₆O₈S₂Na.1.5H₂O Calcd.; C, 37.29; H, 3.68; N, 15.39; ;L Found: C, 37.42; H, 4.26; N, 15.00.

EXAMPLE II-2

Production of sodium 7-[2-(2-imino-4-thiazolin-4-yl)-2-methylcarbamoyloximinoacetamido]-3-acetoxymethyl-3-cephem-4-carboxylate (syn-isomer)

In 0.5 ml of dimethylacetamide, 0.12 g of 7-(4-bromo-2-methylcarbamoyloximino-3-oxobutyrylamino)-3-acetoxymethyl-3-cephem-4-carboxylic acid (syn-isomer) and 0.02 g of thiourea were stirred at room temperature for 5 hours, at the end of which time 5 ml of ether was added. The supernatant was removed by decanting, 5 ml of ether was added to the residue and the resultant powders were collected by filtration. The powders were dissolved in 0.5 ml of a 1 M aqueous solution of sodium hydrogen carbonate and the solution was chromatographed on a column of polystyrene resin (Amberlite XAD-2, Rohm and Haas Co., trade name) and developed with water. The fractions containing the desired compound were pooled and lyophilized. By the above procedure there was obtained the above-indicated compound. Yield 0.05 g. In IR(KBr) and NMR (100 MHz, D₂O), this compound was indentical with the compound according to Example II-1.

EXAMPLE II-3 TO EXAMPLE II-25

In the same manner as Example II-1, compounds of the formula:

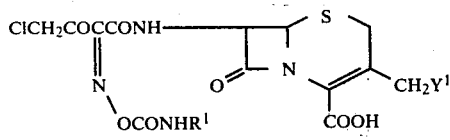

were respectively reacted with thiourea to produce the corresponding compounds having the formula;

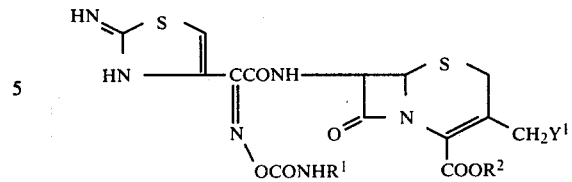

The physical data on these product compounds are given below. [Notes] In the following table,
"Anal." denotes "elemental analysis";
"Calcd. for" denote "theoretical values";
"Found" denotes "values found".
(The same definitions apply hereinafter.)

| Ex. No. | $R^1$ | $Y^1$ | $R^2$ | Physical Data |
|---|---|---|---|---|
| II-3 | —$CH_3$ | —$OCONH_2$ | Na | IR(KBr, cm$^{-1}$): 1760. NMR(100MHz,d$_6$-DMSO,δ): 2.70(d,J=5Hz,NCH$_3$),3.23 & 3.49(ABq,J=18Hz,2-H), 4.76 & 4.91(ABq,J=13Hz,3-CH$_2$),5.04(d,J=5Hz,6-H), 5.63(dd,J=5 & 8Hz,7-H), 6.48(b-s,OCONH$_2$),7.07(s, thiazoline 5-H),7.16(q,J= 5Hz,CONHMe),7.31(b-s,NH=C— NH—), 9.70(d,J=8Hz,CONH). |
| II-4 | —$CH_3$ | —S-(tetrazole-N-CH$_3$) | Na | IR(KBr,cm$^{-1}$): 1760 NMR(100MHz,d$_6$-DMSO,δ): 2.71(d,J=5Hz,NCH$_3$),3.40 & 3.68(ABq,J=18Hz,2-H),3.94 (s,tetrazole-CH$_3$),4.26 & 4.46(ABq,J=13Hz,3-CH$_2$), 5.05(d,J=5Hz,6-H),5.66(dd, J=5 & 8Hz,7-H), 7.07(s, thiazoline 5-H),7.20(q,J= 5Hz,CONHMe),7.31(b-s,NH=C— NH—),9.76(d,J=8Hz,CONH). Anal.Calcd.for C$_{17}$H$_{17}$N$_{10}$O$_6$ S$_3$Na . 2.5H$_2$O:C 32.85; H 3.57; N 22.53. Found: C 32.72; H 3.73; N 22.39. |
| II-5 | —$CH_3$ | —S-(thiadiazole-CH$_3$) | Na | IR(KBr, cm$^{-1}$): 1760 NMR(100MHz,d$_6$-DMSO, δ): 2.69(s, thiadiazole-CH$_3$), 2.71(d,J=5Hz,NCH$_3$),3.37 & 3.64(ABq,J=18Hz,2-H),4.34 & 4.56(ABq,J=13HZ,3-CH$_2$), 5.06(d,J=5Hz,6-H),5.64(dd, J=5 & 8Hz,7-H), 7.08(s, thiazoline 5-H),7.19(q,J= 5Hz,CONHMe),7.28(b-s,NH=C— NH—), 9.75(d,J=8Hz,CONH). Anal.Calcd. for C$_{18}$H$_{17}$N$_8$O$_6$ S$_4$Na . 2.5H$_2$O; C 33.90; H 3.48; N 17.57. Found: C 33.99; H 3.57; N 17.53. |
| II-6 | —$CH_3$ | —H | Na | IR(KBr,cm$^{-1}$): 1750 NMR(100MHz,d$_6$-DMSO,δ): 1.97(s,3-CH$_3$),2.71(d,J=5 Hz,NCH$_3$),3.11 & 3.45(ABq, J=18Hz,2-H),5.00(d,J=5Hz, |

-continued

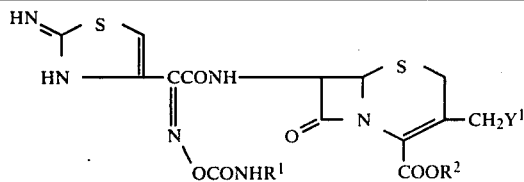

| Ex. No. | R[1] | Y[1] | R[2] | Physical Data |
|---|---|---|---|---|
| | | | | 6-H),5.57(dd,J=5 & 8Hs,7-H),7.07(s,thiazoline 5-H), 7.24(q,J=5Hz,CONHMe),7.33 (b-s,NH=C—NH—),9.74(d,J= 8Hz,CONH). Anal. Calcd. for $C_{15}H_{15}N_6O_6S_2Na \cdot 2H_2O$:C 36.14; H 3.84; N 16.86. Found: C 36.78; H 4.46; N 16.46. |
| II-7 | —CH$_2$CH$_3$ | —OAc | Na | IR(KBr,cm$^{-1}$):1750 NMR(100MHz,d$_6$-DMSO,δ): 1.08(t,J=7Hz,Et-CH$_3$),2.03 (s,OAc),3.14(dg,J=6 & 7Hz, Et-CH$_2$),3.22 & 3.52(ABq, J=18Hz,2-H),4.81 & 5.04 (ABq,J=13Hz,3-CH$_2$),5.05(d, J=5Hz,6-H),5.64(dd,J=5 & 8Hz,7-H),7.06(s,thiazoline 5-H),7.22(t,J=6Hz,CONHEt), 7.30(b-s,NH=C—NH—),9.74(d, J=8Hz,CONH). NMR(100MHz,D$_2$O,δ):1.18(t, J=7Hz,Et-CH$_3$),2.14(s,OAc), 3.28(q,J=7Hz,Et-CH$_2$),3.40 & 3.71(ABq,J=18Hz,2-H), 4.74 & 4.94(ABq,J=13Hz,3-CH$_2$),5.24(d,J=5Hz,6-H),5.86 (d,J=5Hz,7-H),7.26(s, thiazoline 5-H). Anal. Calcd. for $C_{18}H_{19}N_6O_8S_2Na \cdot 2.5H_2O$: O 37.89; H 4.06; N 14.73. Found: C 37.79; H 4.21; N 14.68. |
| II-8 | —CH$_2$CH$_3$ | —OCONH$_2$ | Na | IR(KBr,cm$^{-1}$): 1750. NMR(100MHz,d$_6$-DMSO,δ): 1.08(t,J=7Hz,Et-CH$_3$),3.13 (dt,J=6 & 7Hz,Et-CH$_2$),3.22 & 3.48(ABq,J=18Hz,2-H), 4.73 & 4.91(ABq,J=13Hz,3-CH$_2$),5.03(d,J=5Hz,6-H), 5.63(dd,J=5 & 8Hz,7-H), 6.48(b-s,OCONH$_2$),7.06(s, thiazoline 5-H),7.29(t, J=6Hz,CONHEt),7.30(b-s, NH=C—NH—),9.74(d,J=8Hz,CONH). |
| II-9 | —CH$_2$CH$_3$ | ![tetrazole-S-CH$_3$] | Na | IR(KBr,cm$^{-1}$): 1760 NMR(100MHz,d$_6$-DMSO,δ): 1.08(t,J=7Hz,Et-CH$_3$),3.14 (dq,J=6 & 7Hz,Et-CH$_2$),3.40 & 3.68(ABq,J=18Hz,2-H),3.94 (s,tetrazole -CH$_3$),4.26 & 4.45(ABq,J=13Hz,3-CH$_2$), 5.05(d,J=5Hz,6-H),5.65(dd, J=5 & 8Hz,7-H),7.06(s, thiazoline 5-H),7.28(t,J= 6Hz,CONHEt),7.32(b-s,NH=C— NH—),9.77(d,J=8Hz,CONH). Anal Calcd. for $C_{18}H_{19}N_{10}O_6S_3Na \cdot 2.5H_2O$: C 34.01; H 3.81; N 22.04. Found: C 34.13; H 3.96; N 21.89. |

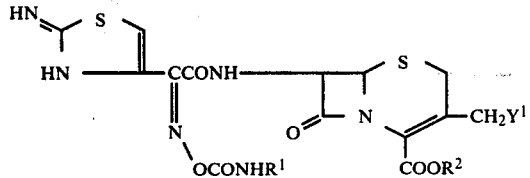

| Ex. No. | R¹ | Y¹ | R² | Physical Data |
|---|---|---|---|---|
| II-10 | —CH$_2$CH$_3$ | —S—(thiadiazole)—S—CH$_3$ (N=N) | Na | IR(KBr,cm$^{-1}$): 1760 NMR(100MHz,d$_6$-DMSO,δ): 1.09(t,J=7Hz,Et-CH$_3$),2.69 (s,thiadiazole-CH$_3$),3.14 (dq,J=6 & 7Hz,Et-CH$_2$),3.38 & 3.63(ABq,J=18Hz,2-H), 4.36 & 4.56(ABq,J=13Hz,3-CH$_2$),5.06(d,J=5Hz,6-H), 5.65(dd,J=5 & 8Hz,7-H), 7.06(s,thiazoline 5-H), 7.24(t,J=6Hz,CONHEt),7.30 (b-s,NH=C(—)—NH—),9.76(d,J=8Hz,CONH). Anal.Calcd. for C$_{19}$H$_{19}$N$_8$O$_6$S$_4$Na . 3H$_2$O: C 34.54; H 3.81; N 16.96. Found: C 34.42; H 3.80; N 16.98. |
| II-11 | —CH$_2$CH$_3$ | —H | Na | IR(KBr,cm$^{-1}$): 1750 NMR(100MHz,d$_6$-IMSO,δ): 1.08(t,J=7Hz,Et-CH$_3$),1.97 (s,3-CH$_3$),3.14(dq,J=6 & 7 Hz,NCH$_2$CH$_3$),3.10 & 3.44(ABq, J=18Hz,2-H),5.00(d,J=5Hz, 6-H),5.56(dd,J=5 & 8Hz,7-H),7.06(s,thiazoline 5-H), 7.30(t,J=6Hz,CONHEt),7.34 (b-s,NH=C(—)—NH—),9.74(d,J=8Hz,CONH). Anal.Calcd. for C$_{16}$H$_{17}$N$_6$O$_6$S$_2$Na . 2H$_2$O; C 37.50; H 4.13; N 16.40. Found: C 38.16; H 4.90; N 16.07. |
| II-12 | —CH$_2$CH$_2$CH$_3$ | —OAc | Na | IR(KBr,cm$^{-1}$): 1750 NMR(100MHz,d$_6$-DMSO,δ): 0.87(t,J=7Hz,Pr—CH$_3$),1.2 to 1.8(m,CH$_3$CH$_2$CH$_2$—),2.03 (s,OAc),3.07(dt,J=6 & 6Hz, NCH$_2$C$_2$H$_5$),3.21 & 3.52(ABq, J=18Hz,2-H),4.82 & 5.04( ABq,J=13Hz,3-CH$_2$),5.05(d, J=5Hz,6-H),5.64(dd,J=5 & 8Hz,7-H),7.06(s,thiazoline 5-H),7.22(t,J=6Hz,CONHPr), 7.32(b-s,NH=C(—)—NH—),9.75(d, J=8Hz,CONH). NMR(100MHz,D$_2$O,δ): 0.92(t, J=7Hz,Pr—CH$_3$),1.4 to 1.8(m, CH$_3$CH$_2$CH$_2$),2.13(s,OAc), 3.21(t,J=7Hz,NCH$_2$C$_2$H$_5$),3.40 & 3.62(ABq,J=18Hz,2-H),4.74 & 4.94(ABq,J=13Hz,3-CH$_2$), 5.25(d,J=5Hz,6-H),5.86(d, J=5Hz,7-H),7.27(s,thiazoline 5-H), Anal. Calcd. for C$_{19}$H$_{21}$N$_6$O$_8$S$_2$Na . 2.5H$_2$O: C 38.47; H 4.42 N 14.16. Found: C 38.55; H 4.37; N 14.16. |
| II-13 | —CH$_2$CH$_2$CH$_3$ | —OCONH$_2$ | Na | IR(KBr,cm$^{-1}$): 1750. NMR(100MHz,d$_6$-DMSO,δ): 0.87(t,J=7Hz,Pr—CH$_3$),1.2 to 1.7(m,CH$_3$CH$_2$CH$_2$),3.07(dd, J=6 & 6Hz,NCH$_2$C$_2$H$_5$),3.23 & 3.49(ABq,J=18Hz,2-H), 4.75 & 4.91(ABq,J=13Hz, 3-CH$_2$),5.04(d,J=5Hz,6-H), |

-continued

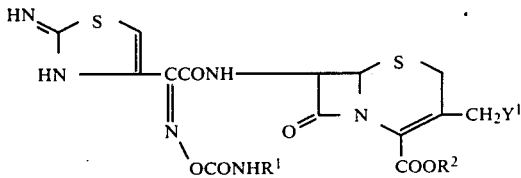

| Ex. No. | R¹ | Y¹ | R² | Physical Data |
|---|---|---|---|---|
| | | | | 5.64(dd,J=5 & 8Hz,7-H), 6.49(b-s,OCONH₂),7.06(s, thiazoline 5-H),7.28(t,J= 6Hz,CONHPr),7.30(b-s,NH=C(|)—NH-),9.75(d,J=8Hz,CONH). Anal. Calcd. for C₁₈H₂₀N₇O₈S₂Na . 2H₂O: C 36.92; H. 4.13; N 16.74. Found: C 37.22; H 4.41; N 16.30. |
| II-14 | —CH₂CH₂CH₃ | -S-$\underset{\underset{CH_3}{\|}}{\overset{N\text{———}N}{\underset{N}{\diagdown\diagup}}}$=N | Na | IR(KBr,cm⁻¹): 1760. NMR(100MHz,d₆-DMSO,δ): 0.86(t,J=7Hz,Pr—CH₂),1.2 to 1.7(m,CH₃CH₂CH₂),3.06 (dt,J=6 & 6Hz,NCH₂C₂H₅), 3.40 & 3.67(ABq,J=18Hz,2-H),3.93(s,tetrazole-CH₃), 4.26 & 4.44(ABq,J=18Hz,3-CH₂),5.04(d,J=5Hz,6-H), 5.65(dd,J=5 & 8Hz,7-H), 7.05(s,thiazoline 5-H), 7.26(t,J=6Hz,CONHPr),7.29 (b-s,NH=C(|)—NH—),9.77(d,J= 8Hz,CONH). Anal.Calcd. for C₁₉H₂₁N₁₀O₆S₃Na . 3H₂O: C 34.65; H 4.13; N 21.26. Found: C 34.37; H 3.99; N 21.28. |
| II-15 | —CH₂CH₂CH₃ | —H | Na | IR(KBr,cm⁻¹): 1750. NMR(100MHz,d₆-DMSO,δ): 0.86(t,J=7Hz,Pr—CH₃),1.2 to 1.7(m,CH₃CH₂CH₂),1.96 (s,3-CH₃),3.07(dt,J=6 & 6Hz,NCH₂C₂H₅),3.09 & 3.43 (ABq,J=18Hz,2-H),4.98(d,J= 5Hz,6-H),5.56(dd,J=5 & 8Hz, 7-H),7.06(s,thiazoline 5-H), 7.30(t,J=6Hz,CONHPr),7.32 (b-s,NH=C(|)—NH—),9.72(d,J= 8Hz,CONH). Anal.Calcd; for C₁₇H₁₉N₆O₆S₂Na . 2.5H₂O: C 38.13; H 4.52. N 15.69. Found: C 38.24; H 4.65; N 15.53. |
| II-16 | —CH(CH₃)₂ | —OAc | Na | IR(KBr,cm⁻¹): 1750. NMR(100MHz,d₆-DMSO,δ): 1.15(d,J=6Hz,iso-Pr—CH₃), 2.05(s,OAc),3.25 & 3.57(A Bq,J=18Hz,2-H),4.82 & 5.04 (ABq,J=13Hz,3-CH₂),5.08 (d,J=5Hz,6-H),5.66(dd,J=5 & 8Hz,7-H),7.04(s,thiazoline 5-H),7.08(d,J=8Hz,CONH-iso- Pr),7.36(b-s,NH=C(|)—NH—), 9.76(d,J=8Hz,CONH). NMR(100MHz,D₂O,δ): 1.24(d, J=6Hz,iso-Pr—CH₃),2.14(s, OAc),3.41 & 3.73(ABq,J=18 Hz,2-H),3.84(septet,J=6Hz, iso-Pr—CH),4.76 & 4.98(AB q,J=13Hz,3-CH₂),5.26(d,J= 5Hz,6-H),5.88(d,J=3Hz,7-H ),7.28(s,thiazoline 5-H). Anal. Calcd. for C₁₉H₂₁N₆O₈S₂Na . 3.5H₂O: C 37.31; H 4.61; |

-continued

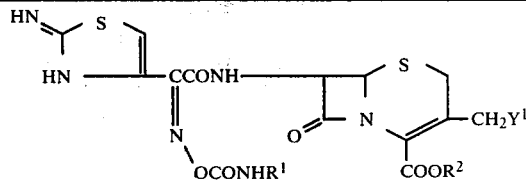

| Ex. No. | R¹ | Y¹ | R² | Physical Data |
|---|---|---|---|---|
| II-17 | —CH(CH₃)₂ | —OCONH₂ | Na | N 13.74. Found: C 37.53; H 4.32; N 13.78. IR(KBr,cm⁻¹): 1760. NMR(100MHz,d₆-DMSO,δ): 1.17(d,J=6Hz,iso-Pr—CH₃), 3.24 & 3.49(ABq,J=18Hz,2-H), 4.72 & 4.92(ABq,J=13Hz, 3-CH₂),5.06(d,J=5Hz,6-H), 5.65(dd,J=5 & 8Hz,7-H), 6.50(b-s,OCONH₂),7.04(s, thiazoline 5-H),7.11(d,J= 8Hz,CONHiso-Pr),7.34(b-s, NH=Ċ—NH—),9.77(d,J=8Hz, CONH). Anal.Calcd. for C₁₈H₂₀N₇O₈S₂Na . 2.5H₂O: C 36.36; H 4.24, N 16.49. Found: C 36.71; H 4.55; N 16.22. |
| II-18 | —CH(CH₃)₂ | -S-(tetrazole with N-CH₃) | Na | IR(KBr,cm⁻¹): 1760. NMR(100MHz,d₆-DMSO, δ): 1.14(d,J=6Hz,iso-Pr—CH₃), 3.40 & 3.67(ABq,J=18Hz,2-H ),3.93(s,tetrazole-CH₃), 4.26 & 4.44(ABq,J=13Hz,3-CH₂),5.05(d,J=5Hz,6-H), 5.66(dd,J=5 & 8Hz,7-H), 7.04(s,thiazoline 5-H), 7.09(d,J=8Hz,CONHiso-Pr), 7.30(b-s,NH=Ċ—NH—),9.78 (d,J=8Hz,CONH). Anal. Calcd. for C₁₉H₂₁N₁₀O₆S₃Na . 2.5H₂O:C 35.13; H 4.03; N 21.56. Found: C 35.16; H 4.23; N 21.37. |
| II-19 | —CH(CH₃)₂ | —H | Na | IR(KBr,cm⁻¹): 1750. NMR(100MHz,d₆-DMSO,δ): 1.16(d,J=6Hz,iso-Pr—CH₃), 1.97(s,3-CH₃),3.11 & 3.45 (ABq,J=18Hz,2-H),5.00(d, J=5Hz,6-H),5.57(dd,J=5 & 8Hz,7-H),7.04(s,thiazoline 5-H),7.13(d,J=8Hz,CONHiso-Pr),7.36(b-s,NH=Ċ—NH—), 9.73(d,J=8Hz,CONH). Anal. Calcd. for C₁₇H₁₉N₆O₆S₂Na . 3H₂O:C 37.50; H 4.63; N 15.43. Found: C 37.64; H 4.66; N 15.17 |
| II-20 | —CH₂CH₂CH₂ . CH₃ | —OAc | Na | IR(KBr,cm⁻¹): 17.50. NMR(100MHz,d₆-DMSO,δ): 0.89(t,J=6Hz,Bu-CH₃),1.0 to 1.7(m,CH₃CH₂CH₂CH₂), 2.03(s,OAc),3.11(dt,J=6 & 6Hz,NCH₂C₃H₇),3.23 & 3.53 (ABq,J=18Hz,2-H),4.83 & 5.04(ABq,J=13Hz,3-CH₂), 5.06(d,J=5Hz,6-H),5.66(dd, J=5 & 8Hz,7-H),7.06(s, thiazoline 5-H),7.24(t,J=6Hz, CONHBu),7.35(b-s,NH=Ċ—NH—), 9.78(d,J=8Hz,CONH). NMR(100MHz,D₂O,δ):0.92(t, J=6Hz,Bu-CH₃),1.1 to 1.8 (m,CH₃CH₂CH₂CH₂),2.15(s, |

-continued

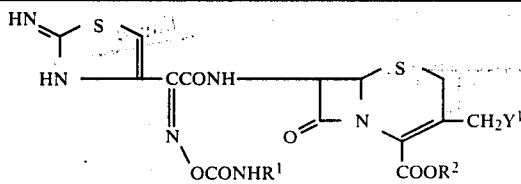

| Ex. No. | R¹ | Y¹ | R² | Physical Data |
|---|---|---|---|---|
| | | | | OAc),3.25(t,J=6Hz,NCH₂C₃H₇),3.39 & 3.73(ABq,J=18Hz,2-H),4.76 & 4.98(ABq,J=13Hz,3-CH₂),5.26(d,J=5Hz,6-H),5.88(d,J=5Hz,7-H),7.28(s,thiazoline 5-H). Anal. Calcd. for C₂₀H₂₃N₆O₈S₂Na . 2.5H₂O:C 39.53; H 4.65; N 13.83. Found: C 39.38; H 4.52; N 13.94 |
| II-21 | —CH₂CH₂CH₂.CH₃ | —OCONH₂ | Na | IR(KBr,cm⁻¹):1750. NMR(100MHz,d₆-DMSO,δ): 0.89(t,J=6Hz,Bu-CH₃)1.0 to 1.7(m,CH₃CH₂CH₂CH₂), 3.11(dt,J=6 & 6Hz,NCH₂C₃H₇), 3.23 & 3.48(ABq,J=18Hz,2-H), 4.75 & 4.91(ABq,J=13Hz,3-CH₂),5.04(d,J=5Hz,6-H), 5.64(dd,J=5 & 8Hz,7-H), 6.50(b-s,OCONH₂),7.06(s,thiazoline 5-H),7.28(t,J= 6Hz,CONHBu),7.32(b-s,NH=C—NH—),9.75(d,J=8Hz,CONH). Anal. Calcd. for C₁₉H₂₂N₇O₈S₂Na . 3H₂O:C 36.95; H 4.57; N 15.88. Found: C 37.04; H 4.46; N 15.92. |
| II-22 | —CH₂CH₂CH₂.CH₃ | (tetrazolylthio with N-CH₃) | Na | IR(KBr,cm⁻¹): 1760. NMR(100MHz,d₆-DMSO, δ): 0.87(t,J=6Hz,Bu-CH₃),1.0 to 1.7(m,CH₃CH₂CH₂CH₂), 3.10(dt,J=6 & 6Hz,NCH₂C₃H₇), 3.40 & 3.68(ABq,J=18Hz,2-H),3.93(s,tetrazole-CH₃), 4.26 & 4.44(ABq,J=13Hz,3-CH₂),5.05(d,J=5Hz,6-H), 5.66(dd,J=5 & 8Hz,7-H), 7.06(s,thiazoline 5-H), 7.23(t,J=6Hz,CONHBu),7.30 (b-s,NH=C—NH—),9.76(d,J=8Hz,CONH). Anal.Calcd. for C₂₀H₂₃N₁₀O₆S₃Na . 3.5H₂O:C 35.24; H 4.44; N 20.55. Found: C 35.05; H 4.26; N 20.43. |
| II-23 | —CH₂CH₂CH₂.CH₃ | —H | Na | IR(KBr,cm⁻¹): 1750. NMR(100MHZ,d₆-DMSO,δ): 0.89(t,J=6Hz,Bu-CH₃),1.0 to 1.8(m,CH₃CH₂CH₂CH₂), 1.97(s,3-CH₃),3.11(dt,J= 6 & 6Hz,NCH₂C₃H₇),3.09 & 3.43(ABq,J=18Hz,2-H),4.99 (d,J=5Hz,6-H),5.56(dd,J=5 & 8Hz,7-H),7.06(s,thiazoline 5-H),7.29(t,J=7Hz,CONHBu), 7.34(b-s,NH=C—NH—),9.72 (d,J=8Hz,CONH). Anal.Calcd.for C₁₈H₂₁N₆O₆S₃Na . 1.5H₂O:C 38.36; H 4.29; N 14.91. Found: C 38.47; H 4.76; N 15.09. |

-continued

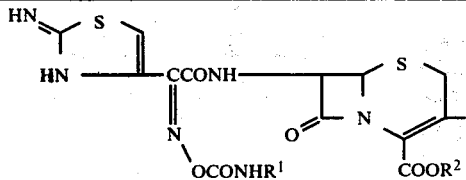

| Ex. No. | R¹ | Y¹ | R² | Physical Data |
|---------|----|----|-----|---------------|
| II-24 | cyclohexyl | —OAc | Na | IR(KBr,cm⁻¹): 1750. NMR(100MHz,d₆-DMSOδ): 1.0 to 2.0(m,Cyclohexyl-CH₂—),2.02(s,OAc),3.22 & 3.53(Abq,J=18Hz,2-H),4.82 & 5.04(ABq,J=13Hz,3-CH₂), 5.06(d,J=5Hz,6-H),5.65(dd, J=5 & 8Hz,7-H),7.00(d,J=8Hz,CONH-cyclohexyl),7.04 (s,thiazoline 5-H),7.36(<br>b-s,NH=C—NH—),9.76(d,J=8Hz,CONH). Anal.Calcd. for C₂₂H₂₅N₆O₈S₂Na . 3H₂O:C 41.12; H 4.86; N 13.08. Found: C 41.38; H 4.81; N 12.38. |
| II-25 | phenyl | —OAc | Na | IR(KBr.cm⁻¹): 1750. NMR(100MHz,d₆-DMSO,δ): 2.02(s,OAc),3.23 & 3.55 (ABq,J=18Hz,2-H),4.80 & 5.05(ABq,J=13Hz,3-CH₂), 5.09(d,J=5Hz,6-H),5.70(dd, J=5 & 8Hz,7-H),7.09(s, thiazoline 5-H),6.8–7.7 (m,phenyl), 9.65(s,CONH-phenyl),9.84(d,J=8Hz, CONH). Anal.Calcd. for C₂₂H₁₉N₆O₈S₂Na . 4H₂O:C 40.37; H 4.16; N 12.84. Found: C 40.37; H 3.69; N 13.47. |

EXAMPLE II-26

Production of 7-[2-(2-imino-4-thiazolin-4-yl)-2-methylcaarbamoyloximinoacetamido]-3-acetoxymethyl-3-cephem-4-carboxylic acid hydrochloride (syn-isomer)

In 25 ml of acetonitrile was suspended 4.20 g of 7-(4-chloro-2-hydroximino-3-oxobutyrylamino)-3-acetoxymethyl-3-cephem-4-carboxylic acid (syn-isomer), followed by addition of 4 ml of methyl isocyanate. The mixture was stirred at room temperature for 16 hours, at the end of which time it was concentrated under reduced pressure. To the residue was added 10 ml of acetonitrile and the mixture was concentrated under reduced pressure, whereby a glass-like solid residue was obtained. To this residue was added 0.761 g of thiourea and the mixture was stirred in 20 ml of dimethylacetamide at room temperature for 16 hours, at the end of which time 100 ml of ether was added. The mixture was stirred, the supernatant was discarded by decanting, 100 ml of ether was added to the residue. After stirring, the supernatant was discarded by decanting and the residue was dissolved in 20 ml of methanol. The solution was added to a mixture of 200 ml of ethyl acetate and 200 ml of ether with stirring. The resultant powders were collected by filtration, washed with 50 ml of ether twice and dried. By the above procedure was obtained 4.44 g of the above-indicated compound.

IR(KBr, cm⁻¹): 1770.

NMR(100 MHz, d₆-DMSO, δ): 2.06(s,OAc), 2.76(d, J=5 Hz, NCH₃), 3.47 & 3.71(ABq, J=18 Hz, 2-H), 4.73 & 5.04(ABq, J=13 Hz, 3-CH₂), 5.22(d, J=5 Hz, 6-H), 5.83(dd, J=5 & 8 Hz, 7-H), 7.24(s, thiazoline 5-H), 7.92(q, J=5 Hz, CONHMe), 10.06 (d, J=8 Hz, CONH).

EXAMPLE III-1

Production of pivaloyloxymethyl 7-[2-(2-imino-4-thiazolin-4-yl)-2-methylcarbamoyloximinoacetamido]-3-(2-methyl-1,3,4-thiadiazol-5-yl)thiomethyl-3-cephem-4-carboxylate(syn-isomer)

In 1 ml of dimethylformamide was dissolved 0.127 g of sodium 7-[2-(2-imino-4-thiazolin-4-yl)-2-methylcarbamoyloximinoacetamido]-3-(2-methyl-1,3,4-thiadiazol-5-yl)thiomethyl-3-cephem-4-carboxylate(-syn-isomer) and, under ice-cooling and stirring, 50 μl of iodomethyl pivalate was added dropwise over a period of 1 minute. The mixture was further stirred under ice-cooling for 10 minutes, after which 40 ml of ethyl acetate and 10 ml of saturated aqueous sodium chloride were added. The organic layer was further washed with 10 ml of saturated aqueous sodium chloride twice, dried over anhydrous magnesium sulfate and concentrated under reduced pressure. To the residue was added 50 ml of ether and the mixture was stirred. The resultant powders were collected by filtration and dried. By the above procedure was obtained the above-indicated compound. Yield 0.089 g.

IR(KBr, cm$^{-1}$): 1780.

NMR(100 MHz, d$_6$-DMSO, δ): 1.18(s,C(CH$_3$)$_3$), 2.70(s, thiadiazol-CH$_3$), 2.69(d,J=5 Hz, NCH$_3$), 3.60 & 3.84(ABq, J=18 Hz, 2-H), 4.17 & 4.57(ABq, J=13 Hz, 3-CH$_2$), 5.19(d,J=5 Hz, 6-H), 5.80 & 5.94 (ABq, J=6 Hz, COOCH$_2$O), 5.83(dd, J=5 & 8 Hz, 7-H), 7.08(s, thiazoline 5-H), 7.14(a, J=5 Hz, CONHMe), 9.79(d, J=8 Hz, CONH)

Elemental analysis: Calcd. for C$_{24}$H$_{28}$N$_8$O$_8$S$_4$.1.5-H$_2$O; C, 40.50; H, 4.39; N, 15.74; Found C, 40.78; H, 4.25; N, 15.50.

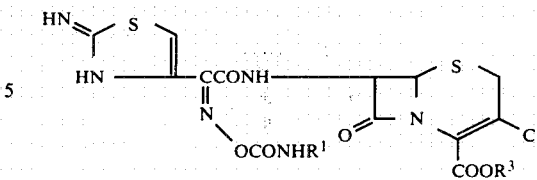

The physical data on the product compounds are given below.

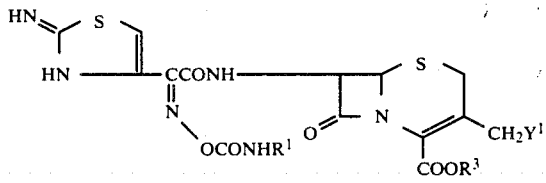

| Ex. No. | R$^1$ | Y$^1$ | R$^3$ | Physical Data |
|---|---|---|---|---|
| III-2 | —CH$_3$ | (tetrazole-S-N(CH$_3$)) | —CH$_2$OCOC(CH$_3$)$_3$ with CH$_3$ | IR(KBr, cm$^{-1}$): 1780 NMR(100MHz, d$_6$-DMSO, δ): 1.18(s, C(CH$_3$)$_3$), 2.70(d, J=3Hz, NCH$_3$), 3.62 & 3.85 (ABq, J=18Hz, 2-H), 3.94 (s, tetrazole-CH$_3$), 4.19 & 4.45(ABq, J=13Hz, 3-CH$_2$), 5.18(d, J=5Hz, 6-H), 5.79 & 5.93(ABq, J=6Hz, COOCH$_2$O), 5.82(dd, J=5 & 8Hz, 7-H), 7.10(s, thiazoline 5-H), 7.16(q, J=5Hz, CONHMe), 9.80 (d, J=8Hz, CONH). Anal. Calcd. for C$_{23}$H$_{28}$N$_{10}$O$_8$S$_3$ . 2H$_2$O:C 39.20; H 4.58; N 19.87. Found: C 39.94; H 4.24; N 19.22 |
| III-3 | —CH$_2$CH$_3$ | (tetrazole-S-N(CH$_3$)) | —CH$_2$OCOC(CH$_3$)$_3$ with CH$_3$ | IR(KBr, cm$^{-1}$): 1780 NMR(100MHz, d$_6$-DMSO, δ): 1.08(t, J=7Hz, Et-CH$_3$), 1.18 (s, C(CH$_3$)$_3$), 3.14(dq, J=6 & 7Hz, Et-CH$_2$), 3.63 & 3.85 (ABq, J=18Hz, 2-H), 3.94(s, tetrazole-CH$_3$), 4.20 & 4.46(ABq, J=13Hz, 3-CH$_2$), 5.18(d, J=5Hz, 6-H), 5.79 & 5.93(ABq, J=6Hz, COOCH$_2$O), 5.82(dd, J=5 & 8Hz, 7-H), 7.08(s, thiazoline 5-H), 7.18(t, J=6Hz, CONHMe), 9.80(d, J=8Hz, CONH). Anal. Calcd. for C$_{24}$H$_{30}$N$_{10}$O$_8$S$_3$ . 5H$_2$O:C 41.14; H 4.60; N 19.99. Found: C 40.97; H 4.51; N 19.73 |

EXAMPLE III-2 AND EXAMPLE III-3

In the same manner as Example III-1, compounds of the formula:

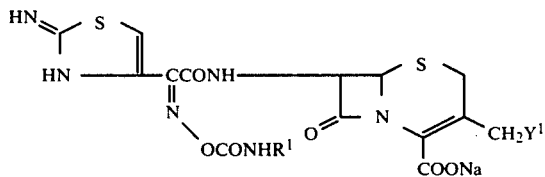

were respectively reacted with an esterifying agent and the products were similarly treated to obtain the corresponding compounds of the formula:

EXAMPLE IV-1

Production of sodium 7-[2-(2-imino-4-thiazolin-4-yl)-2-methylcarbamoyloximinoacetamido]-3-(2-methyl-1,3,4-thiadiazol-5-yl)thiomethyl-3-cephem-4-carboxylate (syn-isomer)

0.535 g (1 m mole) of 7-[2-(2-imino-4-thiazolin-4-yl)-2-methylcarbamoyloximinoacetamido]-3-acetoxymethyl-3-cephem-4-carboxylic acid.hydrochloride (syn-isomer), 0.150 g. (1.5 m moles) of 2-methyl-5-mercapto-1,3,4-thiadiazole and 2 ml of 1 M-sodium hydrogen carbonate solution were stirred in 20 ml of phosphate buffer (pH 6.4) at 50°–53° C. for 12 hours. After cooling to room temperature, 2 g of sodium hydrogen carbonate was added and the reaction mixture was chromatographed on a column of polystyrene resin (Amberlite XAD-2, Rohm and Haas Co., trade name), elution being carried out with aqueous ethanol. The corresponding fractions were pooled, concentrated and lyophilized. By the above procedure was obtained the above-indicated compound. Yield 0.180 g (Synthetic Procedure as an alternative of Example II-5)

IR(KBr,cm$^{-1}$): 1760.

NMR(100 MHz, d$_6$-DMSO, δ): 2.69(s, thiadiazole-CH$_3$), 2.72(d, J=5 Hz, NCH$_3$), 3.39 & 3.67(ABq, J=18 Hz, 2-H), 4.38 & 4.58(ABq, J=13 Hz, 3-CH$_2$), 5.06(d, J=5 Hz, 6-H), 5.64 (dd, J=5 & 8 Hz, 7-H), 7.07(s, thiazole 5-H), 7.20(q, J=5 Hz, CO<u>N</u>HMe), 7.30 (b-s, NH=C—NH—), 9.76(d,J=8 Hz, CONH).

Elemental analysis, for C$_{18}$H$_{17}$N$_8$O$_6$S$_4$Na.2.5H$_2$O: Calcd. C, 33.90; H, 3.48; N, 17.57; Found C, 34.00; H, 3.46; N, 17.74.

EXAMPLE IV-2

Production of 7-[2-(2-imino-4-thiazolin-4-yl)-2-methylcarbamoyloximinoacetamido]-3-(4-carbamoyl-pyridiniummethyl)-3-cephem-4-carboxylate (syn-isomer)

0.535 g (1 m mole) of 7-[2-(2-imino-4-thiazolin-4-yl)-2-methylcarbamoyloximinoacetamido]-3-acetoxymethyl-3-cephem-4-carboxylic acid.hydrochloride (syn-isomer), 0.500 g (4.1 m moles) of isonicotinamide and 1.0 ml of 1 M-sodium hydrogen carbonate solution were stirred in 20 ml of phosphate buffer (pH 6.4) at 70° C. for 4 hours. Thereafter, 4 ml of 1 M-sodium hydrogen carbonate solution was added and the mixture was chromatographed on a column of polystyrene resin (Amberlite XAD-2, Rohm and Haas Co., trade name), elution being carried out with aqueous ethanol. The corresponding fractions were pooled, concentrated and lyophilized. By the above procedure was obtained the above-indicated compound.

Yield 0.128 g.

IR(KBr, cm$^{-1}$): 1750.

NMR(100 MHz, d$_6$-DMSO, δ): 2.68(d, J=5 Hz, NCH$_3$), 3.13 & obscure (ABq, J=18 Hz, 2-H), 5.11(d, J=5 Hz, 6-H), 5.24 & 5.78 (ABq, J=13 Hz, 3-CH$_2$), 5.71(dd, J=5 & 8 Hz, 7-H), 7.05(s, thiazoline 5-H), 7.13(q, J=5 Hz, CO<u>N</u>HMe), 7.24(b-s, NH=C̵—NH—), 8.46 & 9.56

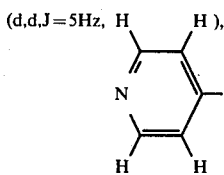
(d,d,J=5Hz, H   H )

9.76(d, J=8 Hz, CONH).

Elemental analysis: C$_{21}$H$_{20}$N$_8$O$_7$S$_2$.5H$_2$O: Calcd. C, 38.77; H, 4.65; N, 17.22; Found C, 38.54; H, 4.26; N, 17.32.

EXAMPLE IV-3

Production of 7-[2-(2-imino-4-thiazolin-4-yl)-2-methylcarbamoyloximinoacetamido]-3-[1-(2-dimethylammonium)ethyl-1H-tetrazol-5-yl]thiomethyl-3-cephem-4-carboxylate (syn-isomer)

0.535 g (1 m mole) of 7-[2-(2-imino-4-thiazolin-4-yl)-2-methylcarbamoyloximinoacetamido)-3-acetoxymethyl-3-cephem-4-carboxylic acid.hydrochloride (syn-isomer), 0.209 g (1.2 m moles) of 1-(2-dimethylamino)ethyl-5-mercapto-1H-tetrazole and 2 ml of 1 M-sodium hydrogen carbonate solution were stirred in 20 ml of phosphate buffer (pH 6.4) at 70° C. for 4 hours. After cooling to room temperature, the reaction mixture was adjusted to pH 3.5 with acetic acid and filtered to remove the insolubles. The filtrate was chromatographed on a column of polystyrene resin (Amberlite XAD-2, Rohm and Haas Co., trade name), elution being carried out with aqueous ethanol. The corresponding fractions are pooled, concentrated and lyophilized. By the above procedure there was obtained the above-indicated compound. Yield 0.171 g.

IR(KBr, cm$^{-1}$):1760.

NMR(100 MHz, D$_2$O+NaHCO$_3$, δ): 2.42(s, N(CH$_3$)$_2$), 2.88(s, NCH$_3$), 3.08(t,J=6 Hz, C<u>H$_2$</u>N(CH$_3$)$_2$), 3.51 & 3.84(ABq, J=18 Hz, 2-H), 4.20 & 4.41(ABq, J=13 Hz, 3-CH$_2$), 4.53(t, J=6 Hz, tetrazole-CH$_2$—), 5.25(d, J=5 Hz, 6H), 5.83(d, J=5 Hz, 7-H), 7.26(s, thiazoline 5-H).

Elemental analysis: C$_{20}$H$_{25}$N$_{11}$O$_6$S$_3$.3H$_2$O: Calcd. C, 36.08; H, 4.69; N, 23.14; Found C, 36.22; H, 4.57; N, 21.24.

EXAMPLE IV-4 TO EXAMPLE IV-11

Generally as in Example IV-1 to Example IV-3, compounds having the formula:

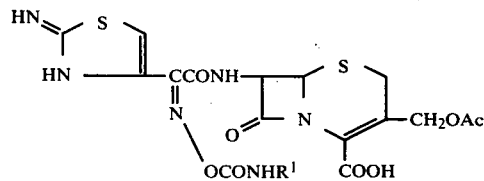

were respectively reacted with a nitrogen-containing heterocyclic thiol or a tertiary amine in the conventional manner and the reaction products were respectively treated in the conventional manner to obtain the corresponding compounds having the formula:

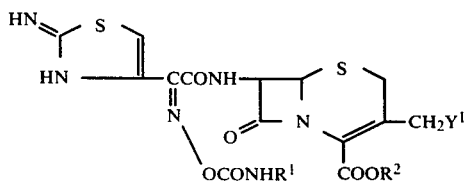

The physical data on the compounds these obtained are shown below.

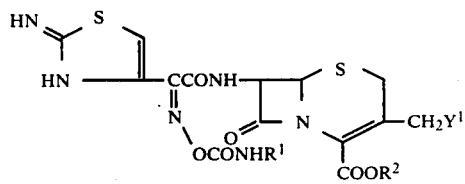

| Ex. No. | R¹ | Y¹ | R² | Physical Data |
|---|---|---|---|---|
| IV-4 | —CH₃ | -S-[tetrazole N=N / N-N]-CH₂CH₂OH | Na | IR(KBr,cm⁻¹): 1750. NMR(100MHz, D₂O,δ):2.86(s, NCH₃),3.47 & 3.81(ABq,J=18Hz,2-H),4.03(t,J=6Hz, CH₂CH₂OH),4.12 & 4.40(ABq, J=13Hz,3-CH₂),4.54(t,J=6 Hz,tetrazole-CH₂—),5.22(d, J=5Hz,6-H),5.82(d,J=5Hz, 7-H),7.26(s,thiazoline 5-H). Anal.Calcd.for C₁₈H₁₉N₁₀O₇S₃Na . 4H₂O:C 31.86; H 4.01;N 20.64. Found: C 32.18; H 3.81; H 19.04 |
| IV-5 | —CH₃ | -S-[triazole N=N / N-CH₃]-CH₂OH | Na | IR(KBr,cm⁻¹): 1750 NMR(100MHz,D₂O,δ):2.86(s, NCH₃),3.41 & 3.87(ABq,J=18Hz,2-H),3.73(s,triazole —CH₃),3.76 & 4.32(ABq,J=13Hz,3-CH₂—),4.81(s, triazole-CH₂—),5.19(d,J=5Hz,6-H),5.79(d,J=5Hz,7-H),7.27(s,thiazoline 5-H). Anal.Calcd.for C₁₉H₂₀N₉O₇S₃Na . 4.5H₂O:C 33.23; H 4.27, N 18.36. Found: C 33.56; H 4.20; N 17.52. |
| IV-6 | —CH₃ | -S-[thiadiazole N=N / S]-CH₂CONH₂ | Na | IR(KBr,cm⁻¹): 1760. NMR(100MHz,D₂O,δ):2.86(s, NCH₃),3.45 & 3.80(ABq,J=18Hz,2-H),4.08 & 4.48(ABq, J=13Hz,3-CH₂),5.22(d,J=5 Hz,6-H),5.84(d,J=5Hz,7-H), 7.26(s,thiazoline 5-H). Anal.Calcd. for C₁₉H₁₈N₉O₇S₄Na . 4.5H₂O:C 31.84; H 3.80; N 17.59. Found: C 31.80; H 3.56; N 17.22 |
| IV-7 | —CH₃ | -S-[thiazole N / S]-CH₂COONa | Na | IR(KBr,cm⁻¹): 1760 NMR(100MHz,D₂O,δ):2.86 (s,NCH₃),3.43 & 3.75 (ABq,J=18Hz,2-H),3.67(s, thiazole 4-CH₂),3.90 & 4.51(ABq,J=13Hz, 3-CH₂), 5.20(d,J=6Hz,6-H),5.82(d, J=5Hz,7-H),7.28(s,thiazole 5-H). Anal.Calcd. for C₂₀H₁₇N₇O₈S₄Na₂ . 4.5H₂O:C 32.52; H 3.55; N 13.27.Found: C 32.40; H 3.70; N 13.04. |

-continued

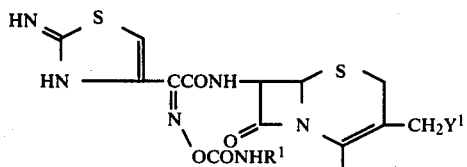

| Ex. No. | R¹ | Y¹ | R² | Physical Data |
|---|---|---|---|---|
| IV-8 | —CH₃ | -S-(thiadiazole with CH₃) | Na | IR(KBr,cm$^{-1}$): 1760 NMR(100MHz,D$_2$O,δ):2.56 (s,thiadiazole-CH$_3$),2.85(s, NCH$_3$),3.43 & 3.77(ABq,J= 18Hz,2-H),4.17 & 4.53( ABq,J=13Hz,3-CH$_2$),5.23(d, J=5Hz,6-H),5.84(d,J=5Hz, 7-H),7.23(s,thiazoline 5-H). Anal.Calcd. for C$_{18}$H$_{17}$N$_8$O$_6$ S$_4$Na . 4H$_2$O:C 32.53; H 3.79 ; N 16.86. Found: C 32.30; H 3.77; N 16.70. |
| IV-9 | —CH₃ | -S-(triazole NH) | Na | IR(KBr,cm$^{-1}$):1750 NMR(100MHz,D$_2$O,δ):2.85(s, NCH$_3$),3.39 & 3.81(ABq,J= 18Hz,2-H),3.65 & 4.23(ABq, J=13Hz,3-CH$_2$),5.18(d,J= 5Hz,6-H),5.77(d,J=5Hz,7-H ),7.26(s,thiazoline 5-H), 7.96(s,triazole-CH). Anal.Calcd. for C$_{17}$H$_{16}$N$_9$ C$_6$S$_3$Na . 3.8H$_2$O:C 32.41; H 3.78; N 20.00. Found: C 32.84; H 3.64; N 19.60. |
| IV-10 | —CH₃ | -S-(oxadiazole CH₃) | Na | IR(KBr,cm$^{-1}$): 1750. NMR(100MHz,D$_2$O,δ):2.56(s, oxadiazole-CH$_3$),2.86(s, NCH$_3$),3.44 & 3.85(ABq, J=18Hz,2-H),3.96 & 4.49 (ABq,J=13Hz,3-CH$_2$),5.21 (d,J=5Hz,6-H),5.82(d,J= 5Hz,7-H),7.27(s,thiazoline 5-H). Anal.Calcd. for C$_{18}$H$_{17}$N$_8$ O$_7$S$_3$Na . 3.5H$_2$O: C 33.80; H 3.78; N 17.52. Found: C 33.85; H 3.79; N 17.15. |
| IV-11 | —CH₃ | -S-(tetrazole N-CH₂CH₂SO₃Na) | Na | IR(KBr,cm$^{-1}$):1750 NRM(100MHz,D$_2$O,δ):2.87(s, NCH$_3$),3.51 & 3.86(ABq,J= 18Hz,2-H),3.54(t,J=5Hz, CH$_2$SO$_3$),4.12 & 4.41(ABq, J=13Hz,3-CH$_2$),4.82(t,J= 6Hz,tetrazole-CH$_2$),5.25( d,J=5Hz,6-H),5.84(d,J= 5Hz,7-H),7.32(s,thiazoline 5-H) |

What is claimed is:

1. A 2-(syn)-carbamoyloximinoacetamido cephalosporin of the formula:

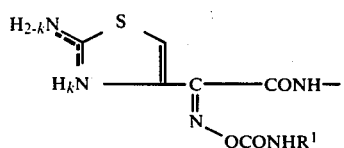

-continued

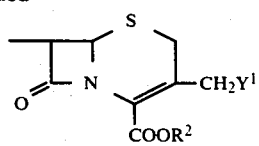

wherein Y¹ is (1) hydrogen, (2) hydroxyl, (3) carbamoyloxy, (4) acyloxy of the formula —OT where T is benzoyl or aliphatic carbonyl having 2 to 10 carbon atoms, (5) quaternary ammonium of the formula:

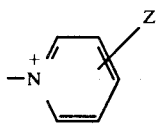

wherein Z is hydrogen, alkyl of 1 to 4 carbon atoms, carbamoyl, carboxyl, sulfo or alkoxy of 1 to 4 carbon atoms, (6) quinolinium, (7) picolinium, (8) lutidinium or (9) nitrogen-containing heterocyclic thio of the formula:

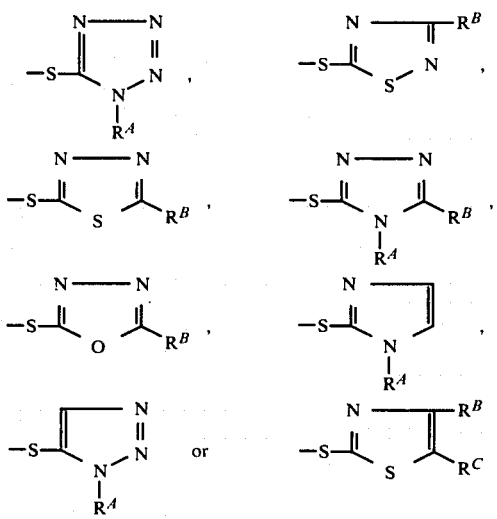

wherein $R^A$ is hydrogen or a group of the formula $-(CH_2)_nP$ where n is an integer of 1 to 3 and P is hydrogen, hydroxyl, alkoxy of 1 to 4 carbon atoms, alkylthio of 1 to 4 carbon atoms, a group of the formula $-COOR^4$ (where $R^4$ is hydrogen or alkyl of 1 to 4 carbon atoms), a group of the formula

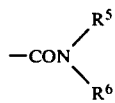

(where each of $R^5$ and $R^6$ is hydrogen or alkyl of 1 to 4 carbon atoms) or a group of the formula

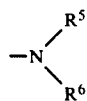

(where $R^5$ and $R^6$ are as defined above); and $R^B$ and $R^C$ may be the same or different and each represents hydrogen, amino, carbamoyl, a group of the formula $-NH-COOR^7$ (where $R^7$ is alkyl of 1 to 4 carbon atoms), a group of the formula $-S-(CH_2)_nQ$ (where n is an integer of 1 to 3 and Q is carboxyl, hydroxyl, hydrogen or sulfo) or a group of the formula $-(CH_2)_nP$ (where n and P are as defined above), $R^1$ is alkyl of one to six carbons, cycloalkyl of five to six carbons, phenyl, benzyl, phenethyl, phenylpropyl or phenylbutyl, $R^2$ is hydrogen, alkoxy-alkyl in which the alkoxy has 1 to 4 carbon atoms and the alkyl has 1 to 4 carbon atoms, alkylthiomethyl in which the alkyl has 1 to 4 carbon atoms, pivaloyloxymethyl, alkoxycarbonyloxymethyl in which the alkoxy has 1 to 4 carbon atoms, 2-n-propionyloxyethoxymethyl, α-n-butyryloxybenzyl or 3-methoxy-4-acetyloxybenzyl, and k is 0 or 1, or a pharmaceutically acceptable salt thereof.

2. A compound as claimed in claim 1, wherein $Y^1$ is hydrogen, carbamoyloxy, acetoxy, the quaternary ammonium, quinolinium, picolinium, lutidinium or the nitrogen-containing heterocyclic thio, $R^1$ is an alkyl of 1 to 6 carbon atoms and $R^2$ is hydrogen.

3. A compound as claimed in claim 1, wherein the acyloxy is acetoxy.

4. A compound as claimed in claim 1, wherein $Y^1$ is hydrogen, carbamoyloxy, acetoxy, the quaternary ammonium, quinolinium, picolinium, lutidinium or the nitrogen-containing heterocyclic thio, $R^1$ is methyl, and $R^2$ is hydrogen.

5. A compound as claimed in claim 1, namely 7-[2-(2-imino-4-thiazolin-4-yl)-2-methylcarbamoyloxyiminoacetamido]-3-acetoxymethyl-3-cephem-4-carboxylic acid (syn-isomer) or a pharmaceutically acceptable salt thereof.

6. A compound as claimed in claim 1, namely 7-[2-(2-imino-4-thiazolin-4-yl)-2-methylcarbamoyloxyiminoacetamido]-3-carbamoyloxymethyl-3-cephem-4-carboxylic acid (syn-isomer) or a pharmaceutically acceptable salt thereof.

7. A compound as claimed in claim 1, namely 7-[2-(2-imino-4-thiazolin-4-yl)-2-methylcarbamoyloxyiminoacetamido]-3-(1-methyl-1H-tetrazol-5-yl)thiomethyl-3-cephem-4-carboxylic acid (syn-isomer) or a pharmaceutically acceptable salt thereof.

8. A compound as claimed in claim 1, namely 7-[2-(2-imino-4-thiazolin-4-yl)-2-methylcarbamoyloxyiminoacetamido]-3-(2-methyl-1,3,4-thiadiazol-5-yl)thiomethyl-3-cephem-4-carboxylic acid (syn-isomer) or a pharmaceutically acceptable salt thereof.

9. A compound as claimed in claim 1, namely 7-[2-(2-imino-4-thiazolin-4-yl)-2-methylcarbamoyloxyiminoacetamido]-3-methyl-3-cephem-4-carboxylic acid (syn-isomer) or a pharmaceutically acceptable salt thereof.

10. A compound as claimed in claim 1, namely 7-[2-(2-imino-4-thiazolin-4-yl)-2-methylcarbamoyloxyiminoacetamido]-3-[1-(2-dimethylaminoethyl)-1H-tetrazol-5-yl]thiomethyl-3-cephem-4-carboxylic acid (syn-isomer) or a pharmaceutically acceptable salt thereof.

11. A compound as claimed in claim 1, namely 7-[2-(2-imino-4-thiazolin-4-yl)-2-methylcarbamoyloxyiminoacetamido]-3-[1-(2-hydroxyethyl)-1H-tetrazol-5-yl]thiomethyl-3-cephem-4-carboxylic acid (syn-isomer) or a pharmaceutically acceptable salt thereof.

12. A compound as claimed in claim 1, namely 7-[2-(2-imino-4-thiazolin-4-yl)-2-methylcarbamoyloxyiminoacetamido]-3-(3-hydroxymethyl-4-methyl-1,2,4-triazol-5-yl)thiomethyl-3-cephem-4-carboxylic acid (syn-isomer) or a pharmaceutically acceptable salt thereof.

13. A compound as claimed in claim 1, namely 7-[2-(2-imino-4-thiazolin-4-yl)-2-methylcarbamoyloxyiminoacetamido]-3-(2-carbamoylmethyl-1,3,4-thiadiazol-5-yl)thiomethyl-3-cephem-4-carboxylic acid (syn-isomer) or a pharmaceutically acceptable salt thereof.

14. A compound as claimed in claim 1, namely 7-[2-(2-imino-4-thiazolin-4-yl)-2-methylcarbamoyloxyiminoacetamido]-3-(4-carboxymethyl-1,3-thiazol-2-yl)thiomethyl-3-cephem-4-carboxylic acid (syn-isomer) or a pharmaceutically acceptable salt thereof.

15. A compound as claimed in claim 1, namely 7-[2-(2-imino-4-thiazolin-4-yl)-2-methylcarbamoyloxyiminoacetamido]-3-(3-methyl-1,2,4-thiadiazol-5-yl)thiomethyl-3-cephem-4-carboxylic acid (syn-isomer) or a pharmaceutically acceptable salt thereof.

16. A compound as claimed in claim 1, namely 7-[2-(2-imino-4-thiazolin-4-yl)-2-methylcarbamoyloxyiminoacetamido]-3-(1H-1,2,3-triazol-5-yl)thiomethyl-3-cephem-4-carboxylic acid (syn-isomer) or a pharmaceutically acceptable salt thereof.

17. A compound as claimed in claim 1, namely 7-[2-(2-imino-4-thiazolin-4-yl)-2-methylcarbamoyloxyiminoacetamido]-3-(2-methyl-1,3,4-oxadiazol-5-yl)thiomethyl-3-cephem-4-carboxylic acid (syn-isomer) or a pharmaceutically acceptable salt thereof.

18. A compound as claimed in claim 1, namely 7-[2-(2-imino-4-thiazolin-4-yl)-2-methylcarbamoyloxyiminoacetamido]-3-[1-(2-sulfoethyl)-1H-tetrazol-5-yl]thiomethyl-3-cephem-4-carboxylic acid (syn-isomer) or a pharmaceutically acceptable salt thereof.

19. A compound as claimed in claim 1, namely 7-[2-(2-imino-4-thiazolin-4-yl)-2-methylcarbamoyloxyiminoacetamido]-3-(4-carbamoylpyridiniummethyl)-3-cephem-4-carboxylic acid (syn-isomer) or a pharmaceutically acceptable salt thereof.

20. A compound as claimed in claim 1, namely 7-[2-(2-imino-4-thiazolin-4-yl)-2-ethylcarbamoyloxyiminoacetamido]-3-acetoxymethyl-3-cephem-4-carboxylic acid (syn-isomer) or a pharmaceutically acceptable salt thereof.

21. A compound as claimed in claim 1, namely 7-[2-(2-imino-4-thiazolin-4-yl)-2-ethylcarbamoyloxyiminoacetamido]-3-carbamoyloxymethyl-3-cephem-4-carboxylic acid (syn-isomer) or a pharmaceutically acceptable salt thereof.

22. A compound as claimed in claim 1, namely 7-[2-(2-imino-4-thiazolin-4-yl)-2-ethylcarbamoyloxyiminoacetamido]-3-(1-methyl-1H-tetrazol-5-yl)thiomethyl-3-cephem-4-carboxylic acid (syn-isomer) or a pharmaceutically acceptable salt thereof.

23. A compound as claimed in claim 1, namely 7-[2-(2-imino-4-thiazolin-4-yl)-2-ethylcarbamoyloxyiminoacetamido]-3-(2-methyl-1,3,4-thiadiazol-5-yl)thiomethyl-3-cephem-4-carboxylic acid (syn-isomer) or a pharmaceutically acceptable salt thereof.

24. A compound as claimed in claim 1, namely 7-[2-(2-imino-4-thiazolin-4-yl)-2-ethylcarbamoyloxyiminoacetamido]-3-methyl-3-cephem-4-carboxylic acid (syn-isomer) or a pharmaceutically acceptable salt thereof.

25. An antibacterial composition for the treatment of bacterial infections which contains
(A) a pharmaceutically effective amount of a 2-(syn)-carbamoyloximinoacetamido cephalosporin of the formula:

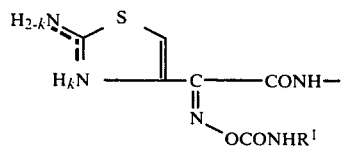

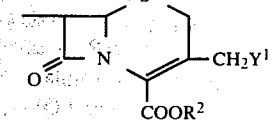

wherein $Y^1$ is (1) hydrogen, (2) hydroxyl, (3) carbamoyloxy, (4) acyloxy of the formula —OT where T is benzoyl or aliphatic carbonyl having 2 to 10 carbon atoms, (5) quaternary ammonium of the formula:

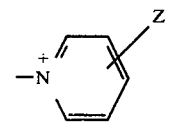

wherein Z is hydrogen, alkyl of 1 to 4 carbon atoms, carbamoyl, carboxyl, sulfo or alkoxy of 1 to 4 carbon atoms, (6) quinolinium, (7) picolinium, (8) lutidinium or (9) nitrogen-containing heterocyclic thio of the formula:

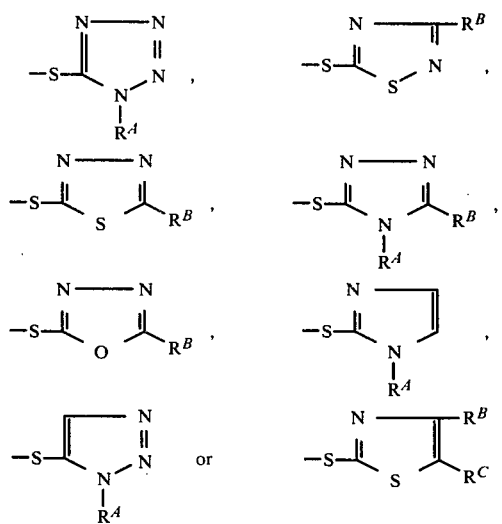

wherein $R^A$ is hydrogen or a group of the formula —$(CH_2)_nP$ where n is an integer of 1 to 3 and P is hydrogen, hydroxyl, alkoxy of 1 to 4 carbon atoms, alkylthio of 1 to 4 carbon atoms, a group of the formula —$COOR^4$ (where $R^4$ is hydrogen or alkyl of 1 to 4 carbon atoms), a group of the formula

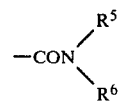

(where each of $R^5$ and $R^6$ is hydrogen or alkyl of 1 to 4 carbon atoms) or a group of the formula

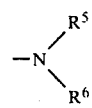

(where $R^5$ and $R^6$ are as defined above); and $R^B$ and $R^C$ may be the same or different and each represents hydrogen, amino, carbamoyl, a group of the formula —NHCOOR$^7$ (where $R^7$ is alkyl of 1 to 4 carbon atoms), a group of the formula —S—(CH$_2$)$_n$Q (where n is an integer of 1 to 3 and Q is carboxyl, hydroxyl, hydrogen or sulfo) or a group of the formula -(CH$_2$)$_n$P (where n and P are as defined above), $R^1$ is alkyl of one to six carbons, cycloalkyl of five to six carbons, phenyl, benzyl, phenethyl, phenylpropyl or phenylbutyl, $R^2$ is hydrogen, alkoxy-alkyl in which the alkoxy has 1 to 4 carbon atoms and the alkyl has 1 to 4 carbon atoms, alkylthiomethyl in which the alkyl has 1 to 4 carbon atoms, pivaloyloxymethyl, alkoxycarbonyloxymethyl in which the alkoxy has 1 to 4 carbon atoms, 2-n-propionyloxyethoxymethyl, α-n-butyryloxybenzyl or 3-methoxy-4-acetyloxybenzyl, and k is 0 or 1, or a pharmaceutically acceptable salt thereof, and (B) a pharmaceutically acceptable carrier therefor.

* * * * *